US011104942B2

(12) United States Patent
Moeller

(10) Patent No.: US 11,104,942 B2
(45) Date of Patent: Aug. 31, 2021

(54) METHOD FOR IDENTIFICATION OF THE MOST ABUNDANT OLIGONUCLEOTIDE SPECIES IN A LIBRARY OF OLIGONUCLEOTIDES

(71) Applicant: GUANGDONG MAIJINJIA BIOTECHNOLOGIES CO., LTD., Guangzhou (CN)

(72) Inventor: Thorleif Moeller, Arslev (DK)

(73) Assignee: Guangdong Maijinjia Biotechnologies, Co. Ltd., Guangzhou (CN)

(*) Notice: Subject to any disclaimer, the term of this patent is extended or adjusted under 35 U.S.C. 154(b) by 447 days.

(21) Appl. No.: 15/772,404

(22) PCT Filed: Oct. 28, 2016

(86) PCT No.: PCT/EP2016/076148
§ 371 (c)(1),
(2) Date: Apr. 30, 2018

(87) PCT Pub. No.: WO2017/072330
PCT Pub. Date: May 4, 2017

(65) Prior Publication Data
US 2019/0144918 A1  May 16, 2019

(30) Foreign Application Priority Data
Oct. 30, 2015 (DK) .................. PA 2015 0672 30

(51) Int. Cl.
| | |
|---|---|
| *C12P 19/34* | (2006.01) |
| *C12Q 1/686* | (2018.01) |
| *A61J 1/20* | (2006.01) |
| *C12Q 1/6832* | (2018.01) |
| *C12N 15/10* | (2006.01) |
| *A61J 1/10* | (2006.01) |
| *A61J 1/14* | (2006.01) |
| *C12Q 1/6811* | (2018.01) |
| *C12Q 1/6806* | (2018.01) |
| *C12Q 1/6853* | (2018.01) |
| *C12Q 1/6874* | (2018.01) |
| *C40B 20/02* | (2006.01) |
| *C40B 40/08* | (2006.01) |
| *C40B 50/14* | (2006.01) |

(52) U.S. Cl.
CPC .............. *C12Q 1/686* (2013.01); *A61J 1/10* (2013.01); *A61J 1/1475* (2013.01); *A61J 1/2024* (2015.05); *A61J 1/2031* (2015.05); *A61J 1/2093* (2013.01); *C12N 15/1068* (2013.01); *C12Q 1/6806* (2013.01); *C12Q 1/6811* (2013.01); *C12Q 1/6832* (2013.01); *C12Q 1/6853* (2013.01); *C12Q 1/6874* (2013.01); *C40B 20/02* (2013.01); *C40B 40/08* (2013.01); *C40B 50/14* (2013.01)

(58) Field of Classification Search
CPC .... C12Q 1/686; C12Q 1/6806; C12Q 1/6874; C12Q 1/6853
See application file for complete search history.

(56) References Cited

U.S. PATENT DOCUMENTS

2010/0240550 A1* 9/2010 Jackson .................. C07K 1/22
                                                           506/9

FOREIGN PATENT DOCUMENTS

| WO | WO-2004099441 A2 * | 11/2004 | ......... C12N 15/1058 |
|---|---|---|---|
| WO | 2005040396 A2 | 5/2005 | |
| WO | 2005078122 A2 | 8/2005 | |
| WO | 2012067901 A1 | 5/2012 | |

OTHER PUBLICATIONS

International Search Report for International Application No. PCT/EP2016/076148 dated May 18, 2017 (8 pages).

* cited by examiner

*Primary Examiner* — Kenneth R Horlick
(74) *Attorney, Agent, or Firm* — Merchant & Gould P.C.

(57) ABSTRACT

A method for identification of the most abundant oligonucleotide species in a library of oligonucleotides comprising more than $10^6$ oligonucleotide species, wherein the oligonucleotides of the library of oligonucleotides are not inherently capable of exponential amplification by PCR and include a coding sequence, which is characteristic of one oligonucleotide specie of the library of oligonucleotides and only one fixed sequence, which is present in a plurality of oligonucleotide species of the library of oligonucleotides, said fixed sequence being located on a 5' side of the coding sequence, and wherein the method comprises specifically amplifying the sequence of a hybridised oligonucleotide species using the steps of: incubating the library of oligonucleotides under conditions of hybridization such as to allow complementary coding sequences to hybridize and form hybridized oligonucleotide species; extending a 3' end of one or more of the hybridised oligonucleotide species, having only one fixed sequence, to provide extended sequences having an extended region, such that the extended region generates a second fixed sequence thereby forming extended sequences having two fixed sequences; amplifying extended sequences comprising two fixed sequences using PCR to provide amplified sequences, and optionally identifying an identity of the amplified sequences thereby revealing an identity of the hybridised oligonucleotide species in the step of incubating. The library of oligonucleotides is selected from the group of a library of encoded molecules, a library of aptamers, a library of reporter sequences derived from a library of encoded molecules, and a library of aptamers.

4 Claims, 24 Drawing Sheets

Specification includes a Sequence Listing.

A.

B.

A

B

A

B

A

B

A

B

A

B

A

B

A

B

A

B

A

B

A

B

A

B

A

B

SEQUENCE LISTING

<160> NUMBER OF SEQ ID NOS: 78

<210> SEQ ID NO 1
<211> LENGTH: 22
<212> TYPE: DNA
<213> ORGANISM: Artificial Sequence
<220> FEATURE:
<223> OTHER INFORMATION: Primary PCR primer, PCR-11

```
<400> SEQUENCE: 1
gggagacaag aataacctca gc                                              22

<210> SEQ ID NO 2
<211> LENGTH: 24
<212> TYPE: DNA
<213> ORGANISM: Artificial Sequence
<220> FEATURE:
<223> OTHER INFORMATION: Secondary PCR primer, PCR-12

<400> SEQUENCE: 2
gcctgttgtg agcctcctgt cgaa                                            24

<210> SEQ ID NO 3
<211> LENGTH: 7
<212> TYPE: DNA
<213> ORGANISM: Artificial Sequence
<220> FEATURE:
<223> OTHER INFORMATION: Restriction Enzyme N.BbvC IA Restriction Site

<400> SEQUENCE: 3 gctgagg                                                                7

<210> SEQ ID NO 4
<211> LENGTH: 58
<212> TYPE: DNA
<213> ORGANISM: Artificial Sequence
<220> FEATURE:
<223> OTHER INFORMATION: Primary signal oligo, PSO-NheI

<400> SEQUENCE: 4
gggagacaag aataacctca gcaaagactc gaagcgaaat atgggcgcca tgctagcg       58

<210> SEQ ID NO 5
<211> LENGTH: 58
<212> TYPE: DNA
<213> ORGANISM: Artificial Sequence
<220> FEATURE:
<223> OTHER INFORMATION: Primary noise oligo, PNO-10e7

<400> SEQUENCE: 5
gggagacaag aataacctca gcmrkkaaky mraayrymac myykgtryrm tcmykkca       58

<210> SEQ ID NO 6
<211> LENGTH: 6
<212> TYPE: DNA
<213> ORGANISM: Artificial Sequence
<220> FEATURE:
<223> OTHER INFORMATION: Restriction Ezyme NheI Restriction Site

<400> SEQUENCE: 6 gctagc                                                                 6

<210> SEQ ID NO 7
<211> LENGTH: 58
<212> TYPE: DNA
<213> ORGANISM: Artificial Sequence
<220> FEATURE:
<223> OTHER INFORMATION: Primary signal oligo, PSO-NheI

<400> SEQUENCE: 7
gggagacaag aataacctca gcaaagactc gaagcgaaat atgggcgcca tgctagcg       58
```

<210> SEQ ID NO 8
<211> LENGTH: 58
<212> TYPE: DNA
<213> ORGANISM: Artificial Sequence
<220> FEATURE:
<223> OTHER INFORMATION: Primary noise oilgo, PNO-10e8

<400> SEQUENCE: 8
gggagacaag aataacctca gcmrkkaaky mrmayrymat rrykytryrm tcmykkya    58

<210> SEQ ID NO 9
<211> LENGTH: 58
<212> TYPE: DNA
<213> ORGANISM: Artificial Sequence
<220> FEATURE:
<223> OTHER INFORMATION: Primary signal oligo, PSO-NheI

<400> SEQUENCE: 9
gggagacaag aataacctca gcaaagactc gaagcgaaat atgggcgcca tgctagcg    58

<210> SEQ ID NO 10
<211> LENGTH: 58
<212> TYPE: DNA
<213> ORGANISM: Artificial Sequence
<220> FEATURE:
<223> OTHER INFORMATION: Primary noise oligo, PNO-10e9

<400> SEQUENCE: 10
gggagacaag aataacctca gcmrkkmaky mrmayrymmt rrykytryrm kcmykkya    58

<210> SEQ ID NO 11
<211> LENGTH: 60
<212> TYPE: DNA
<213> ORGANISM: Artificial Sequence
<220> FEATURE:
<223> OTHER INFORMATION: Secondary signal oligo, SSO-NheI

<400> SEQUENCE: 11
gcctgttgtg agcctcctgt cgaacgctag catggcgccc atatttcgct tcgagtcttt    60

<210> SEQ ID NO 12
<211> LENGTH: 59
<212> TYPE: DNA
<213> ORGANISM: Artificial Sequence
<220> FEATURE:
<223> OTHER INFORMATION: Secondary noise oligo, SNO-10e7

<400> SEQUENCE: 12
gcctgttgtg agcctcctgt cgaatgmmrk gakyryamrr kgtkryrtty krmttmmyk    59

<210> SEQ ID NO 13
<211> LENGTH: 60
<212> TYPE: DNA
<213> ORGANISM: Artificial Sequence
<220> FEATURE:
<223> OTHER INFORMATION: Secondary signal oligo, SSO-NheI

<400> SEQUENCE: 13
gcctgttgtg agcctcctgt cgaacgctag catggcgccc atatttcgct tcgagtcttt    60

<210> SEQ ID NO 14
<211> LENGTH: 60
<212> TYPE: DNA
<213> ORGANISM: Artificial Sequence
<220> FEATURE:
<223> OTHER INFORMATION: Secondary noise oligo, SNO-10e8

```
<400> SEQUENCE: 14
gcctgttgtg agcctcctgt cgaatrmmrk gakyryarmr yyatkryrtk ykrmttmmyk    60

<210> SEQ ID NO 15
<211> LENGTH: 60
<212> TYPE: DNA
<213> ORGANISM: Artificial Sequence
<220> FEATURE:
<223> OTHER INFORMATION: Secondary signal oligo, SSO-NheI

<400> SEQUENCE: 15
gcctgttgtg agcctcctgt cgaacgctag catggcgccc atatttcgct tcgagtcttt    60

<210> SEQ ID NO 16
<211> LENGTH: 60
<212> TYPE: DNA
<213> ORGANISM: Artificial Sequence
<220> FEATURE:
<223> OTHER INFORMATION: Secondary noise oligo, SNO-10e9

<400> SEQUENCE: 16
gcctgttgtg agcctcctgt cgaatrmmrk gmkyryarmr yyakkryrtk ykrmtkmmyk    60

<210> SEQ ID NO 17
<211> LENGTH: 22
<212> TYPE: DNA
<213> ORGANISM: Artificial Sequence
<220> FEATURE:
<223> OTHER INFORMATION: Primary PCR primer, PCR-11

<400> SEQUENCE: 17
gggagacaag aataacctca gc                                              22

<210> SEQ ID NO 18
<211> LENGTH: 24
<212> TYPE: DNA
<213> ORGANISM: Artificial Sequence
<220> FEATURE:
<223> OTHER INFORMATION: Secondary PCR primer, PCR-12

<400> SEQUENCE: 18
gcctgttgtg agcctcctgt cgaa                                            24

<210> SEQ ID NO 19
<211> LENGTH: 40
<212> TYPE: DNA
<213> ORGANISM: Artificial Sequence
<220> FEATURE:
<223> OTHER INFORMATION: Primary PCR product extending primer, Ext1-
      PCR11

<400> SEQUENCE: 19
cacgacgttg taaaacgaca gggagacaag aataacctca                           40

<210> SEQ ID NO 20
<211> LENGTH: 40
<212> TYPE: DNA
<213> ORGANISM: Artificial Sequence
<220> FEATURE:
<223> OTHER INFORMATION: Secondary PCR product extending primer, Ext2-
      PCR12

<400> SEQUENCE: 20
ggataacaat ttcacacaga gcctgttgtg agcctcctgt                           40
```

```
<210> SEQ ID NO 21
<211> LENGTH: 58
<212> TYPE: DNA
<213> ORGANISM: Artificial Sequence
<220> FEATURE:
<223> OTHER INFORMATION: Primary signal ago, PSO-BamHI

<400> SEQUENCE: 21
gggagacaag aataacctca gcagagattt gaaccaaaag acggggatcc tgctatct      58

<210> SEQ ID NO 22
<211> LENGTH: 58
<212> TYPE: DNA
<213> ORGANISM: Artificial Sequence
<220> FEATURE:
<223> OTHER INFORMATION: Primary noise oligo, PNO-10e6

<400> SEQUENCE: 22
gggagacaag aataacctca gcmrdtaaky vgagyrhcac ymbtgtryvc tcmydgca      58

<210> SEQ ID NO 23
<211> LENGTH: 6
<212> TYPE: DNA
<213> ORGANISM: Artificial Sequence
<220> FEATURE:
<223> OTHER INFORMATION: Restriction Enzyme BamHI Restriction Site

<400> SEQUENCE: 23 ggatcc                                                               6

<210> SEQ ID NO 24
<211> LENGTH: 58
<212> TYPE: DNA
<213> ORGANISM: Artificial Sequence
<220> FEATURE:
<223> OTHER INFORMATION: Primary signal oligo, PSO-PacI

<400> SEQUENCE: 24
gggagacaag aataacctca gccgttaatt aaaacgccac ccttgtatgc tcatggca      58

<210> SEQ ID NO 25
<211> LENGTH: 58
<212> TYPE: DNA
<213> ORGANISM: Artificial Sequence
<220> FEATURE:
<223> OTHER INFORMATION: Primary noise oligo, PNO-10e7

<400> SEQUENCE: 25
gggagacaag aataacctca gcmrkkaaky mraayrymac myykgtryrm tcmykkca      58

<210> SEQ ID NO 26
<211> LENGTH: 58
<212> TYPE: DNA
<213> ORGANISM: Artificial Sequence
<220> FEATURE:
<223> OTHER INFORMATION: Primary signal oligo, PSO-BamHI

<400> SEQUENCE: 26
gggagacaag aataacctca gcagagattt gaaccaaaag acggggatcc tgctatct      58

<210> SEQ ID NO 27
<211> LENGTH: 58
<212> TYPE: DNA
<213> ORGANISM: Artificial Sequence
<220> FEATURE:
<223> OTHER INFORMATION: Primary noise oligo, PNO-10e8
```

<400> SEQUENCE: 27
gggagacaag aataacctca gcmrkkaaky mrmayrymat rrykytryrm tcmykkya        58

<210> SEQ ID NO 28
<211> LENGTH: 60
<212> TYPE: DNA
<213> ORGANISM: Artificial Sequence
<220> FEATURE:
<223> OTHER INFORMATION: Secondary signal oligo, SSO-BamHI

<400> SEQUENCE: 28
gcctgttgtg agcctcctgt cgaaagatag caggatcccc gtcttttggt tcaaatctct        60

<210> SEQ ID NO 29
<211> LENGTH: 60
<212> TYPE: DNA
<213> ORGANISM: Artificial Sequence
<220> FEATURE:
<223> OTHER INFORMATION: Secondary noise oligo, SNO-10e6

<400> SEQUENCE: 29
gcctgttgtg agcctcgtgt cgaatgchrk gagbryacav krgtgdyrct cbrmttahyk        60

<210> SEQ ID NO 30
<211> LENGTH: 60
<212> TYPE: DNA
<213> ORGANISM: Artificial Sequence
<220> FEATURE:
<223> OTHER INFORMATION: Secondary signal oligo, SS0-PacI

<400> SEQUENCE: 30
gcctgttgtg agcctcctgt cgaatgccat gagcatacaa gggtggcgtt ttaattaacg        60

<210> SEQ ID NO 31
<211> LENGTH: 58
<212> TYPE: DNA
<213> ORGANISM: Artificial Sequence
<220> FEATURE:
<223> OTHER INFORMATION: Secondary noise oligo, SNO-10e7

<400> SEQUENCE: 31
gcctgttgtg agcctcctgt cgaatgmmrk gakyryacmr rkgtkryrtt ykrmttmm        58

<210> SEQ ID NO 32
<211> LENGTH: 60
<212> TYPE: DNA
<213> ORGANISM: Artificial Sequence
<220> FEATURE:
<223> OTHER INFORMATION: Secondary signal oligo, SSO-BamHI

<400> SEQUENCE: 32
gcctgttgtg agcctcctgt cgaaagatag caggatcccc gtcttttggt tcaaatctct        60

<210> SEQ ID NO 33
<211> LENGTH: 60
<212> TYPE: DNA
<213> ORGANISM: Artificial Sequence
<220> FEATURE:
<223> OTHER INFORMATION: Secondary noise oligo, SNO-10e8

<400> SEQUENCE: 33
gcctgttgtg agcctcctgt cgaatrmmrk gakyryarmr yyatkryrtk ykrmttmmyk        60

```
<210> SEQ ID NO 34
<211> LENGTH: 20
<212> TYPE: DNA
<213> ORGANISM: Artificial Sequence
<220> FEATURE:
<223> OTHER INFORMATION: Primary PCR primer 1, PCR-BamHI-1

<400> SEQUENCE: 34
gggatatagc aatcctacgg                                              20

<210> SEQ ID NO 35
<211> LENGTH: 20
<212> TYPE: DNA
<213> ORGANISM: Artificial Sequence
<220> FEATURE:
<223> OTHER INFORMATION: Primary PCR primer biotin 1, PCR-BamHI-1-bt

<400> SEQUENCE: 35
gggatatagc aatcctacgg                                              20

<210> SEQ ID NO 36
<211> LENGTH: 20
<212> TYPE: DNA
<213> ORGANISM: Artificial Sequence
<220> FEATURE:
<223> OTHER INFORMATION: Secondary PCR primer 1, PCR-EcoRI-1

<400> SEQUENCE: 36
ggagtagcaa agtagcgtga                                              20

<210> SEQ ID NO 37
<211> LENGTH: 20
<212> TYPE: DNA
<213> ORGANISM: Artificial Sequence
<220> FEATURE:
<223> OTHER INFORMATION: Secondary PCR primer biotin 1, PCR-EcoRI-1-bt

<400> SEQUENCE: 37
ggagtagcaa agtagcgtga                                              20

<210> SEQ ID NO 38
<211> LENGTH: 20
<212> TYPE: DNA
<213> ORGANISM: Artificial Sequence
<220> FEATURE:
<223> OTHER INFORMATION: Primary PCR primer 2, PCR-BamHI-2

<400> SEQUENCE: 38
ggcgtttcta acaacgaagg                                              20

<210> SEQ ID NO 39
<211> LENGTH: 20
<212> TYPE: DNA
<213> ORGANISM: Artificial Sequence
<220> FEATURE:
<223> OTHER INFORMATION: Primary PCR primer biotin 2, PCR-BamHI-2-bt

<400> SEQUENCE: 39
ggcgtttcta acaacgaagg                                              20

<210> SEQ ID NO 40
<211> LENGTH: 20
<212> TYPE: DNA
<213> ORGANISM: Artificial Sequence
<220> FEATURE:
<223> OTHER INFORMATION: Secondary PCR primer 2, PCR-EcoRI-2
```

<210> SEQ ID NO 40
<211> LENGTH: 20
<212> TYPE: DNA
<213> ORGANISM: Artificial Sequence
<220> FEATURE:
<223> OTHER INFORMATION: Secondary PCR primer biotin 2, PCR-EcoRI-2-bt

<400> SEQUENCE: 40
ggcgtggaca ccatttatga                                        20

<210> SEQ ID NO 41
<211> LENGTH: 20
<212> TYPE: DNA
<213> ORGANISM: Artificial Sequence
<220> FEATURE:
<223> OTHER INFORMATION: Secondary PCR primer biotin 2, PCR-EcoRI-2-bt

<400> SEQUENCE: 41
ggcgtggaca ccatttatga                                        20

<210> SEQ ID NO 42
<211> LENGTH: 84
<212> TYPE: DNA
<213> ORGANISM: Artificial Sequence
<220> FEATURE:
<223> OTHER INFORMATION: Signal oligo 1, target-AvrII-1

<400> SEQUENCE: 42
gggatatagc aatcctacgg atccagccat tcgacctgac aaacgtccat cctaggagct    60
gaattcacgc tactttgcta ctcc                                          84

<210> SEQ ID NO 43
<211> LENGTH: 6
<212> TYPE: DNA
<213> ORGANISM: Artificial Sequence
<220> FEATURE:
<223> OTHER INFORMATION: Restriction Enzyme AvrII Restriction Site

<400> SEQUENCE: 43 cctagg                                                        6

<210> SEQ ID NO 44
<211> LENGTH: 6
<212> TYPE: DNA
<213> ORGANISM: Artificial Sequence
<220> FEATURE:
<223> OTHER INFORMATION: Restriction Enzyme EcoRI Restriction Site

<400> SEQUENCE: 44 gaattc                                                        6

<210> SEQ ID NO 45
<211> LENGTH: 84
<212> TYPE: DNA
<213> ORGANISM: Artificial Sequence
<220> FEATURE:
<223> OTHER INFORMATION: Noise oligo 1, library-e8-1

<400> SEQUENCE: 45
gggatatagc aatcctacgc atccmrkyaa kymrmayrym atrmykytry rmtckrkkya    60
gaattcacgc tactttgcta ctcc                                          84

<210> SEQ ID NO 46
<211> LENGTH: 84
<212> TYPE: DNA
<213> ORGANISM: Artificial Sequence
<220> FEATURE:
<223> OTHER INFORMATION: Signal oligo 2, target-AvII-2

<400> SEQUENCE: 46
ggcgtttcta acaacgaagg atccagccat tcgacctgac aaacgtccat cctaggagct     60
gaattcataa atggtgtcca cgcc                                            84

<210> SEQ ID NO 47
<211> LENGTH: 84
<212> TYPE: DNA
<213> ORGANISM: Artificial Sequence
<220> FEATURE:
<223> OTHER INFORMATION: Noise oligo 2, library-e8-2

<400> SEQUENCE: 47
ggcgtttcta acaacgaagg atccmrkyaa kymrmayrym atrmykytry rmtckrkkya     60
gaattcataa atggtgtcca cgcc                                            84

<210> SEQ ID NO 48
<211> LENGTH: 22
<212> TYPE: DNA
<213> ORGANISM: Artificial Sequence
<220> FEATURE:
<223> OTHER INFORMATION: HD1-PCR-1; oligo

<400> SEQUENCE: 48
gatgatagta gttcgtcgtc ac                                              22

<210> SEQ ID NO 49
<211> LENGTH: 22
<212> TYPE: DNA
<213> ORGANISM: Artificial Sequence
<220> FEATURE:
<223> OTHER INFORMATION: HD1-PCR-2; oligo

<400> SEQUENCE: 49
gcagcaacta ctcatcatga ct                                              22

<210> SEQ ID NO 50
<211> LENGTH: 81
<212> TYPE: DNA
<213> ORGANISM: Artificial Sequence
<220> FEATURE:
<223> OTHER INFORMATION: StuI -template, oligo

<400> SEQUENCE: 50
gatgatagta gttcgtcgtc accgaggtta tagcaggcct cgtttcgctc cgactagcta     60
gtcatgatga gtagttgctg c                                               81

<210> SEQ ID NO 51
<211> LENGTH: 20
<212> TYPE: DNA
<213> ORGANISM: Artificial Sequence
<220> FEATURE:
<223> OTHER INFORMATION: Primary PCR primer 1, PCR-BamHI-1

<400> SEQUENCE: 51
gggatatagc aatcctacgg                                                 20

<210> SEQ ID NO 52
<211> LENGTH: 20
<212> TYPE: DNA
<213> ORGANISM: Artificial Sequence
<220> FEATURE:
<223> OTHER INFORMATION: Primary PCR primer biotin 1, PCR-BamHI-1-bt

<400> SEQUENCE: 52
gggatatagc aatcctacgg                                                20

<210> SEQ ID NO 53
<211> LENGTH: 20
<212> TYPE: DNA
<213> ORGANISM: Artificial Sequence
<220> FEATURE:
<223> OTHER INFORMATION: Secondary PCR primer 1, PCR-EcoRI-1

<400> SEQUENCE: 53
ggagtagcaa agtagcgtga                                                20

<210> SEQ ID NO 54
<211> LENGTH: 20
<212> TYPE: DNA
<213> ORGANISM: Artificial Sequence
<220> FEATURE:
<223> OTHER INFORMATION: Secondary PCR primer biotin 1, PCR-EcoRI-1-bt

<400> SEQUENCE: 54
ggagtagcaa agtagcgtga                                                20

<210> SEQ ID NO 55
<211> LENGTH: 20
<212> TYPE: DNA
<213> ORGANISM: Artificial Sequence
<220> FEATURE:
<223> OTHER INFORMATION: Primary PCR primer 2, PCR-BamHI-2

<400> SEQUENCE: 55
ggcgtttcta acaacgaagg                                                20

<210> SEQ ID NO 56
<211> LENGTH: 20
<212> TYPE: DNA
<213> ORGANISM: Artificial Sequence
<220> FEATURE:
<223> OTHER INFORMATION: Primary PCR primer biotin 2, PCR-BamHI-2-bt

<400> SEQUENCE: 56
ggcgtttcta acaacgaagg                                                20

<210> SEQ ID NO 57
<211> LENGTH: 20
<212> TYPE: DNA
<213> ORGANISM: Artificial Sequence
<220> FEATURE:
<223> OTHER INFORMATION: Secondary PCR primer 2, PCR-EcoRI-2

<400> SEQUENCE: 57
ggcgtggaca ccatttatga                                                20

<210> SEQ ID NO 58
<211> LENGTH: 20
<212> TYPE: DNA
<213> ORGANISM: Artificial Sequence
<220> FEATURE:
<223> OTHER INFORMATION: Secondary PCR primer biotin 2, PCR-EcoRI-2-bt

<400> SEQUENCE: 58
ggcgtggaca ccatttatga                                                20

```
<210> SEQ ID NO 59
<211> LENGTH: 84
<212> TYPE: DNA
<213> ORGANISM: Artificial Sequence
<220> FEATURE:
<223> OTHER INFORMATION: Signal oligo 1, target-StuI-1

<400> SEQUENCE: 59
gggatatagc aatcctacgg atccacctag ttggagcgaa caggccttgc tataaccttg    60
gaattcacgc tactttgcta ctcc                                          84

<210> SEQ ID NO 60
<211> LENGTH: 6
<212> TYPE: DNA
<213> ORGANISM: Artificial Sequence
<220> FEATURE:
<223> OTHER INFORMATION: Restriction Enzyme StuI Restriction Site

<400> SEQUENCE: 60 aggcct                                                               6

<210> SEQ ID NO 61
<211> LENGTH: 84
<212> TYPE: DNA
<213> ORGANISM: Artificial Sequence
<220> FEATURE:
<223> OTHER INFORMATION: Noise oligo 1, library-e10-1

<400> SEQUENCE: 61
gggatatagc aatcctacgg atccmydkmc kyhrmayrbm mtrrdmyary vmkcmydkya    60
gaattcacgc tactttgcta ctcc                                          84

<210> SEQ ID NO 62
<211> LENGTH: 84
<212> TYPE: DNA
<213> ORGANISM: Artificial Sequence
<220> FEATURE:
<223> OTHER INFORMATION: Signal oligo 2, target-StuI-2

<400> SEQUENCE: 62
ggcgtttcta acaacgaagg atccacctag ttggagcgaa caggccttgc tataaccttg    60
gaattcataa atggtgtcca cgcc                                          84

<210> SEQ ID NO 63
<211> LENGTH: 84
<212> TYPE: DNA
<213> ORGANISM: Artificial Sequence
<220> FEATURE:
<223> OTHER INFORMATION: Noise oligo 2, library-e10-2

<400> SEQUENCE: 63
ggcgtttcta acaacgaagg atccmydkmc kyhrmayrbm mtrrdmyary vmkcmydkya    60
gaattcataa atggtgtcca cgcc                                          84

<210> SEQ ID NO 64
<211> LENGTH: 22
<212> TYPE: DNA
<213> ORGANISM: Artificial Sequence
<220> FEATURE:
<223> OTHER INFORMATION: HD1-PCR-1, oligo

<400> SEQUENCE: 64
gatgatagta gttcgtcgtc ac                                            22
```

```
<210> SEQ ID NO 65
<211> LENGTH: 22
<212> TYPE: DNA
<213> ORGANISM: Artificial Sequence
<220> FEATURE:
<223> OTHER INFORMATION: HD1-PCR-2, oligo

<400> SEQUENCE: 65
gcagcaacta ctcatcatga ct                                              22

<210> SEQ ID NO 66
<211> LENGTH: 81
<212> TYPE: DNA
<213> ORGANISM: Artificial Sequence
<220> FEATURE:
<223> OTHER INFORMATION: StuI -template, oligo

<400> SEQUENCE: 66
gatgatagta gttcgtcgtc accgaggtta tagcaggcct cgtttccctc cgactagcta     60
gtcatgatga gtagttgctg c                                               81

<210> SEQ ID NO 67
<211> LENGTH: 20
<212> TYPE: DNA
<213> ORGANISM: Artificial Sequence
<220> FEATURE:
<223> OTHER INFORMATION: Primary PCR primer 1, PCR-BamHI-1

<400> SEQUENCE: 67
gggatatagc aatcctacgg                                                 20

<210> SEQ ID NO 68
<211> LENGTH: 20
<212> TYPE: DNA
<213> ORGANISM: Artificial Sequence
<220> FEATURE:
<223> OTHER INFORMATION: Primary PCR primer biotin 1, PCR-BamHI-1-bt

<400> SEQUENCE: 68
gggatatagc aatcctacgg                                                 20

<210> SEQ ID NO 69
<211> LENGTH: 20
<212> TYPE: DNA
<213> ORGANISM: Artificial Sequence
<220> FEATURE:
<223> OTHER INFORMATION: Secondary PCR primer 1, PCR-EcoRI-1

<400> SEQUENCE: 69
ggagtagcaa agtagcgtga                                                 20

<210> SEQ ID NO 70
<211> LENGTH: 20
<212> TYPE: DNA
<213> ORGANISM: Artificial Sequence
<220> FEATURE:
<223> OTHER INFORMATION: Secondary PCR primer biotin 1, PCR-EcoRI-1-bt

<400> SEQUENCE: 70
ggagtagcaa agtagcgtga                                                 20

<210> SEQ ID NO 71
<211> LENGTH: 20
<212> TYPE: DNA
<213> ORGANISM: Artificial Sequence
```

```
<220> FEATURE:
<223> OTHER INFORMATION: Primary PCR primer 2, PCR-BamHI-2

<400> SEQUENCE: 71
ggcgtttcta acaacgaagg                                                  20

<210> SEQ ID NO 72
<211> LENGTH: 20
<212> TYPE: DNA
<213> ORGANISM: Artificial Sequence
<220> FEATURE:
<223> OTHER INFORMATION: Primary PCR primer biotin 2, PCR-BamHI-2-bt

<400> SEQUENCE: 72
ggcgtttcta acaacgaagg                                                  20

<210> SEQ ID NO 73
<211> LENGTH: 20
<212> TYPE: DNA
<213> ORGANISM: Artificial Sequence
<220> FEATURE:
<223> OTHER INFORMATION: Secondary PCR primer 2, PCR-EcoRI-2

<400> SEQUENCE: 73
ggcgtggaca ccatttatga                                                  20

<210> SEQ ID NO 74
<211> LENGTH: 20
<212> TYPE: DNA
<213> ORGANISM: Artificial Sequence
<220> FEATURE:
<223> OTHER INFORMATION: Secondary PCR primer biotin 2, PCR-EcoRI-2-bt

<400> SEQUENCE: 74
ggcgtggaca ccatttatga                                                  20

<210> SEQ ID NO 75
<211> LENGTH: 84
<212> TYPE: DNA
<213> ORGANISM: Artificial Sequence
<220> FEATURE:
<223> OTHER INFORMATION: Signal oligo 1, target-StuI-1

<400> SEQUENCE: 75
gggatatagc aatcctacgg atccacctag ttggagcgaa caggccttgc tataaccttg      60
gaattcacgc tactttgcta ctcc                                             84

<210> SEQ ID NO 76
<211> LENGTH: 60
<212> TYPE: DNA
<213> ORGANISM: Artificial Sequence
<220> FEATURE:
<223> OTHER INFORMATION: Noise oligo 1, library-e10-1

<400> SEQUENCE: 76
gggatatagc aatcctacgg atccmydkmc kyhrmayrbm mtrrdmyary vmkcmydkya      60

<210> SEQ ID NO 77
<211> LENGTH: 84
<212> TYPE: DNA
<213> ORGANISM: Artificial Sequence
<220> FEATURE:
<223> OTHER INFORMATION: Signal oligo 2, target-StuI-2
```

```
<400> SEQUENCE: 77
ggcgtttcta acaacgaagg atccacctag ttggagcgaa caggccttgc tataaccttg      60
gaattcataa atggtgtcca cgcc                                            84

<210> SEQ ID NO 78
<211> LENGTH: 84
<212> TYPE: DNA
<213> ORGANISM: Artificial Sequence
<220> FEATURE:
<223> OTHER INFORMATION: Noise oligo 2, library-e10-2

<400> SEQUENCE: 78
ggcgtttcta acaacgaagg atccmydkmc kyhrmayrbm mtrrdmyary vmkcmydkya      60
gaattcataa atggtgtcca cgcc                                            84
```

METHOD FOR IDENTIFICATION OF THE MOST ABUNDANT OLIGONUCLEOTIDE SPECIES IN A LIBRARY OF OLIGONUCLEOTIDES

FIELD OF THE INVENTION

The present invention relates to manipulation of the information content of a plurality of oligonucleotides and to identification of new molecular activity. The disclosed methods are related to in vitro evolution methods such as SELEX, phage display, mRNA display, DNA-directed synthesis and to combinatorically prepared libraries of encoded compounds that cannot be evolved in the traditional sense.

BACKGROUND

There is a widespread interest in efficient screening of large numbers of compounds to identify candidate compounds with a given desired activity. In particular, the pharmaceutical industry invests massive efforts into the screening of large libraries of potential drug compounds to find compounds that affect, the activity of pharmaceutically relevant targets. Screened compounds include both natural and synthetic compounds. Natural compounds originate from plants, microorganisms or other sources. Synthetic compounds are the result of tedious, organic chemical synthesis. Either way, it is not trivial to build and screen large collections of compounds.

Traditionally, libraries are screened in physically separate assays, which mean that there are limitations as to the number of compounds that can be tested within reasonable time and cost limits, even using automated high throughput screens. It is evident that performing e.g. 1 million assays is a cumbersome task that requires numerous manipulations. To rationalise the screening process, assay volumes are reduced to a minimum with the risk of jeopardising the robustness of the process.

Aiming to reduce the number of manipulations in the generation and screening of libraries, there has been great interest in the synthesis and screening of mixtures of compounds and within the last decade, a relatively simple way of generating very large libraries has been developed. Thus, using combinatorial chemistry, i.e. by synthesising all possible combinations of a set of smaller chemical structures, one-pot libraries of vast size can be generated. However, the screening of these large combinatorial libraries poses significant challenges, as the selection of the specific binders of a library against a particular target is usually accompanied by selection of non-specific binders, i.e. molecules that stick non-specifically the target, stick to the solid support on which the target is immobilised, stick to the tubes etc. This problem may be described as a signal-noise problem. Thus, the term signal-noise problem in the present context refers to the problem of identifying active compounds (the signal) among an excess of inactive compounds (the noise).

One way of circumventing the signal-noise problem is based on genetic methods. The advantage of the genetic methods is that libraries can be evolved through iterated cycles of diversification (mutation), selection and amplification. Hence, the initial library needs only contain very tiny amounts of the individual library members, which in turn allow very large numbers of different library species, i.e. very large libraries. Moreover, the structure of active compounds can be decoded with little effort by DNA sequencing. The power of genetic methods for the screening of large libraries is now generally appreciated and has on numerous occasions been used to find new ligands. The major limitation is that only biological molecules can be screened, i.e. peptides that can be synthesised by the translational apparatus or oligonucleotides that can be copied by polymerases. Therefore various approaches have been suggested for the application of genetic screening methods for libraries composed of non-biological molecules.

Liu et al. have suggested using DNA-templated synthesis as a means of evolving non-natural small molecules, and they are developing methods that can translate the amplifiable information in DNA into synthetic molecules (US 20030113738). Likewise WO 02/103008 describes methods to translate information in DNA into synthetic molecules.

WO 00/23458 describes an approach to indirect DNA template synthesis, wherein the template (DNA-tag) is used for physical separating library members according to the sequence of the DNA-tag.

An early attempt to combine the genetic screening methods with chemically synthesised molecules was put forward in WO93/20242 by Lerner et al. They performed two alternating parallel syntheses such that a DNA tag is chemically linked to the structure being synthesised. In their method, each chemical step is encoded by the addition of an identifier codon, which means that individual steps of the synthesis can be decoded by sequencing the DNA tag. Using a split-mix protocol, a one-pot library of two-piece bifunctional molecules (also termed encoded molecules) can be build. However, a library of this type is not evolvable in the traditional sense because the tag does not specify the synthesis of the compounds, rather the tag only reports the synthesis.

However, in WO93/20242 it is suggested that affinity selected library members have their retrogenetic tag amplified by PCR. DNA strands that are amplified can then be used to enrich for a subset of the library by hybridization with matching tags. The enriched library subset may then be affinity selected against the target and retrogenic tags again PCR amplified for another round of enrichment of a subset of the library. In this method the number of active library members does not increase during the rounds, because active library molecules cannot be amplified/synthesised by way of their tags. Instead it is attempted to remove the non-specific binders from the library as the process proceeds. For very large libraries, though, the amounts of active library members are very tiny, and extra manipulations needed to enrich a library subset before affinity selection seems unfavourable.

In more recent publications (PCT/US2004/042964 and PCT/DK2005/000199), alternative approaches to the generation of libraries of encoded molecules have been described, which differ from WO 93/20242 in that ligation is used for synthesis of the DNA-tag instead of chemical synthesis.

US25135474 describes a method of identifying molecular activity residing in aptamers (oligonucleotides). The object of the method is to identify aptamers, wherein fixed sequences for PCR do not contribute to the activity of the aptamer. Thus, a library of RNA molecules without fixed sequences is selected against a target, where after the selected RNA molecules are used to select complementary DNA strands by hybridization. The complementary DNA strands contain two fixed sequences of which one harbor a T7 promoter. The selected DNA strand is then PCR amplified where after the resulting serve as template in a T7 transcription reaction. During transcription the fixed sequence harboring the T7 promoter is lost. After transcription, the second fixed sequence is removed using RNase H digestion and a DNA primer complementary to the sequence that has to be removed. The resulting library of RNA molecules (devoid of fixed sequences) can then again be fractionated against the target.

US23228619 describes a method, wherein PNA-tags are used as identifier for libraries of encoded molecules. The object of the method is to provide a method of identifying the sequence of PNA-tags corresponding to active encoded molecules. Thus, selected PNA-tags are used to select complementary DNA using hybridization. The selected DNA can then be further manipulated using standard molecular techniques such as DNA sequencing not available to PNA. Thus, the genetic information in PNA in transferred into a more useful form in DNA.

None of the aforementioned references seem to have recognized that hybridization steps may be used in itself for evolving a library of oligonucleotides, preferably a library of oligonucleotides which are derived from a library of modified oligonucleotides that have been fractionated against a molecular target.

The use of hybridization for evolution of a library of oligonucleotides derived from a library of modified oligonucleotides (in the present context also termed a reporter library) was outlined in PCT/DK/000325. When using hybridization as a driver for evolving a library of reporter sequences, it is important that means are provided which allow specific selection of hybridized sequences, as will be apparent from the specification of the present invention.

SUMMARY OF THE INVENTION

The present invention provides methods for identifying oligonucleotides by manipulating the information content of a plurality of oligonucleotides. E.g. methods are provided that allow identification of the most abundant oligonucleotides among a plurality of oligonucleotides. Moreover, the invention provides methods of identifying new molecular activity that may be of relevance for the development of new therapeutics or for the field of nanotechnology.

The presented methods are particular useful in connection with libraries of oligonucleotides such as libraries of encoded molecules and libraries of non-natural oligonucleotides. In this connection, the presented methods can be used to identify active library members. Thus, in a preferred embodiment, a library of oligonucleotides is fractionated (selected) against a molecular target, where after the methods of the invention are used to identify the library members that have a affinity for the target.

DETAILED DESCRIPTION OF THE INVENTION

Figure Legends

FIGS. 17-23 are meant to be non-limiting on the present invention and serve mainly to aid the understanding of the description.

OLIGONUCLEOTIDES OF THE INVENTION

Figure 1:
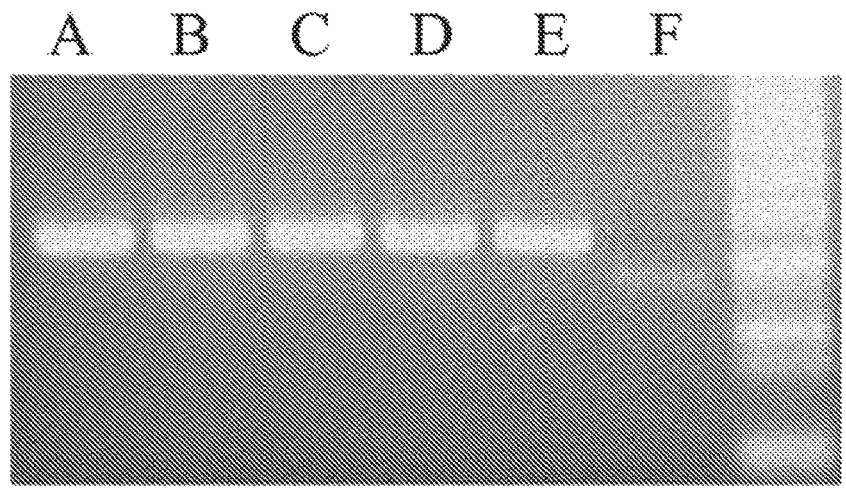
FIGS. 1-16 show experimental results and are commented in the examples section.
Figure 1:
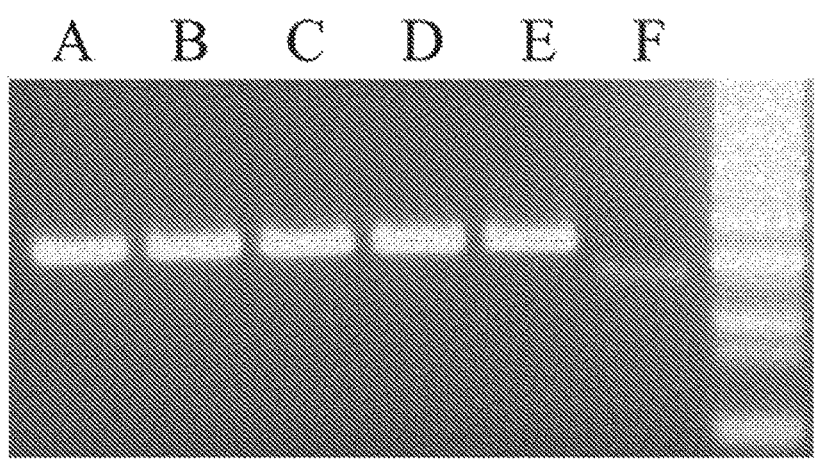

Genetic information in the present context is the information that is carried in DNA, RNA and other oligonucleotides.

The term "plurality" as used in the present context, indicates a multitude of molecules. Thus a plurality of oligonucleotides is a multitude of oligonucleotides. The number of oligonucleotides may be anything from 2 to $10^{15}$. The oligonucleotides may all be identical or they may be different among each other.

In preferred embodiments, a plurality refers to $10^1$-$10^2$, $10^2$-$10^3$, $10^3$-$10^4$, $10^4$-$10^5$, $10^5$-$10^6$, $10^6$-$10^7$, $10^7$-$10^8$, $10^8$-$10^9$, $10^9$-$10^{10}$, $10^{10}$-$10^{11}$, $10^{11}$-$10^{12}$, $10^{12}$-$10^{13}$, $10^{13}$-$10^{14}$, $10^{14}$-$10^{15}$, $10^{15}$-$10^{16}$, $10^{16}$-$10^{17}$, $10^{17}$-$10^{18}$, $10^{18}$-$10^{19}$ and $10^{19}$-$10^{20}$ molecules, respectively.

In it broadest aspect, the plurality of oligonucleotides may be of any origin. They may for example be genomic DNA or RNA purified from cells.

A preferred plurality of oligonucleotides of the invention is a library of oligonucleotides. The various embodiments of such a library are described in the following section. Note, that all the embodiments of a library of oligonucleotides are meant to be combined with all other aspects and embodiments of the invention. However, for practical reasons, all embodiments of a library will not be mentioned for every other aspect and embodiment of the invention.

In its broadest aspect, a library of oligonucleotides is a collection of oligonucleotides collected with the purpose of identifying candidate compounds with a particular activity or function.

Candidate compounds may be an oligonucleotide (an aptamer) or it may be a compound identified by an oligonucleotide (an encoded compound). In one embodiment, the candidate compound may be the compound identified by the oligonucleotide and the encoded compound that together then forms a candidate compound.

The terms "candidate" and "compound" are in the used interchangeably herein with the term "candidate compounds".

When referring to one particular compound in the library, the term "specie" or "library member" may be used interchangeably. E.g. when referring to a library of oligonucleotides, a "specie" of the library or a "library member" is any oligonucleotide with a particular sequence. In other words, the lowest taxonomic class of the library is specie, which is also referred to as a library member.

The terms do not imply anything with regards to number or concentration of the species or library members.

In a preferred embodiment, the term specie refers to a particular encoded compound in a library of encoded compounds.

In another preferred embodiment; the term specie refers to a particular aptamer in a library of aptamers.

In preferred embodiments, the number of different species in a library is $10^1$-$10^2$, $10^2$-$10^3$, $10^3$-$10^4$, $10^4$-$10^5$, $10^5$-$10^6$, $10^6$-$10^7$, $10^7$-$10^8$, $10^8$-$10^9$, $10^9$-$10^{10}$, $10^{10}$-$10^{11}$, $10^{11}$-$10^{12}$, $10^{12}$-$10^{13}$, $10^{13}$-$10^{14}$, $10^{14}$-$10^{15}$, $10^{15}$-$10^{16}$, $10^{16}$-$10^{17}$, $10^{17}$-$10^{18}$, $10^{18}$-$10^{19}$, and $10^{19}$-$10^{20}$ molecules, respectively The term "genetic information of a library of oligonucleotides" refers to both the information carried by individual oligonucleotide species, in addition to the relative abundance of individual oligonucleotide species relatively to other oligonucleotide species and/or to the overall concentration of oligonucleotide species.

In a preferred embodiment, oligonucleotides of a library of oligonucleotides have a defined length.

Thus, in one embodiment, the length of the oligonucleotides is less than 1000 nucleotides.

In other embodiments, the length of the oligonucleotides is less than 900, 800, 700, 600, 500, 400, 300, 250, 200, 180, 160, 140, 130, 120, 120, 110, 100, 90, 80, 70, 60, 50 and 40 nucleotides, respectively In one embodiment, the oligonucleotides of a library have the same length.

In a preferred embodiment, oligonucleotides of the invention are single-stranded.

In another preferred embodiment, oligonucleotides of the invention are double-stranded.

In a preferred embodiment, the oligonucleotides of a library of oligonucleotides comprise a coding region.

In a preferred embodiment, the oligonucleotides of a library of oligonucleotides comprise a coding region and a first fixed sequence.

In another preferred embodiment, the oligonucleotides of a library of oligonucleotides comprise a coding region and a first and a second fixed sequence.

In still another preferred embodiment, the oligonucleotides of a library of oligonucleotides comprise a first and a second fixed sequence, and means for removing at least one of the fixed sequences.

In a preferred embodiment, the means for removing a fixed sequence is a restriction site.

In another embodiment, the fixed sequence comprises uracil nucleotides, which can be used to remove the fixed sequence by employing the active of uracil DNA glycosidase.

When referring to a library of oligonucleotides, a fixed sequence is a sequence, which is present in a plurality of oligonucleotide species of the library.

When referring to a library of oligonucleotides, a coding sequence is a sequence, which is characteristic of one particular oligonucleotide specie of the library. Thus in a preferred embodiment relating to encoded compounds, the coding sequence comprises information that identifies the candidate compound attached to the identifier sequence.

In some embodiments of the invention, the oligonucleotides comprise one or more non-natural nucleotides Libraries of Aptamers In a preferred embodiment, the library of oligonucleotides is a library of aptamers (also herein referred to as aptamer sequences). Aptamers as referred to in the present context are oligonucleotides that are candidate compounds in addition to being carriers of genetic information. Aptamers may be double-stranded, but they are preferably single-stranded such that they can fold into a three-dimensional structure.

In a preferred embodiment, the aptamers comprises non-natural nucleotides.

Typically in the art, aptamers are identified using iterated rounds of selection and amplification. However, functional aptamers comprising non-natural nucleotides cannot be identified in this way, because they are non-amplifiable, i.e. they cannot be replicated by a polymerase because of the presence of non-natural nucleotides. One advantage of the present invention is the possibility of identifying functional aptamers comprising non-natural nucleotides.

Examples of non-natural nucleotides are LNA (locked oligonucleotides) monomers, PNA (peptide oligonucleotides) monomers, INA monomers (intercalating oligonucleotides), backbone modified monomers, etc. Preferred modifications are substitutions with amino acid side chains such as to create an oligonucleotide with the functional groups of a protein.

Aptamers comprising non-natural nucleotides are of interest as they may be better candidate compounds, than aptamers of natural nucleotides. With respect to development of therapeutics, one advantage of may be better bio-stability. Another advantage may be more functional groups, i.e. instead of only four building blocks with their limited amount of functional groups; a wide array may be used. Preferred non-natural oligonucleotides of the present invention include any oligonucleotides modified or changed in any position, as long as they are still capable of specific hybridization.

Libraries of Identifier Sequences

In another preferred embodiment, the library of oligonucleotides is a library of identifier sequences. An identifier sequence is an oligonucleotide that identifies a candidate compound to which it is attached. Such bifunctional compounds comprising both an identifier sequence and a candidate compound are in the present context interchangeably termed encoded compounds and encoded molecules. Thus, a library of identifier sequences is also a library of encoded compounds.

Non-Natural Identifier Sequences

Identifier sequences may comprise non-natural nucleotides and hence not be capable of replication by a polymerase. The use of non-natural nucleotides may be desirable and advantageous for synthetic reasons such as compatibility between synthesis of identifier sequence and encoded candidate compound.

Director-Encoded Libraries

Preferred libraries of encoded compounds are director-encoded libraries, wherein the identifier sequence carried by the encoded compound is both descriptive and directive, such that the identifier sequence can direct the synthesis of the compound.

In a preferred embodiment, the director sequence is replicable by a polymerase, and hence the instructor-encoded library can undergo iterated rounds of selection and amplification and optionally also diversification.

Director-Encoded Peptide Libraries

An example of a director-encoded library is a library of proteins or peptides that have been fused to the genetic information (the gene sequence) specifying the synthesis of the protein or peptide. Such libraries have been described as mRNA display libraries, ribosome display libraries and covalent display libraries and have in common that the genetic information in the identifier (director) is translated into a candidate compound by a process involving ribosomes, i.e. the class of candidate compounds is limited to peptides and proteins.

Director-Encoded Synthetic Libraries

Still another preferred kind of director-encoded library is a library of synthetic compounds prepared by DNA-templated chemistry. In DNA-templated synthesis, the genetic information in DNA is translated into synthetic compounds. Translation may occur in a process where genetic information is directly translated into synthetic compounds as has been outlined in patent applications by Nuevolution A/S and Ensemble Discovery Inc (WO 02/103008 and US 20030113738). Also a number of publications from the group of David Liu, Harvard, have outlined such techniques. Alternatively, hybridization may be used to separate the genetic information (identifier sequences) physically, thus directing an indirect DNA-templated synthesis, as has been outlined on a patent application from Pehr Harbury and coworkers (WO 00/23458). Either way, the result is a candidate compound attached to the genetic information (identifier sequence) that directed its synthesis. A potential advantage of instructor-encoded synthetic libraries is that they are not limited to peptides and proteins, as compared to libraries prepared using ribosomes for translation. However, the process of translating genetic information into synthetic compounds is still in its infancy and it may be difficult to actually access a chemical space, which is expanded and more useful as compared to the chemical space provided by peptides and proteins.

Descriptor-Encoded Libraries

Still another preferred kind of encoded library is a library of synthetic compounds, wherein the identifier sequence carried by the encoded compound is only descriptive, such that the identifier sequence only identifies the compound. Such libraries are herein termed descriptor-encoded libraries.

They may be synthesized using a split-mix protocol as has been outlined for example by Lerner & Brenner (WO 93/20242). More recently, also Praecis Pharmaceuticals Inc. (PCT/US2004/042964) and Nuevolution A/S (PCT/DK2005/000199) have described such techniques in patent applications.

Alternatively, the descriptor-encoded libraries may be synthesized using a convergent strategy, wherein the identifier sequence and candidate compound is synthesized separately and then linked. Obviously, the candidate compound need not necessarily be synthetic. It could also be purified from a natural source.

Currently, libraries of descriptor-encoded libraries may have access to a wider chemical space of than what is presently possible for director-encoded libraries of synthetic compounds. The downside of libraries of descriptor-encoded libraries is that they cannot undergo iterated rounds of selection and amplification and optionally also diversification, because the identifier sequence cannot direct synthesis of the encoded compound. Thus, it may be difficult to identify active library members, because of a signal-noise problem. One advantage of the present invention is the improved possibility of identifying active library members in a descriptor-encoded library.

Libraries of Reporter Sequences

In still another preferred embodiment, the library of oligonucleotides is a library of reporter sequences.

In one embodiment, the library of reporter sequences is derived from a library of aptamers.

In another embodiment, the library of reporter sequences is derived from a library of encoded compounds.

In further embodiments, the library of reporter sequences is derived from a descriptor any of the above described sub-categories of libraries of encoded compounds.

In further embodiments, the library of reporter sequences is derived from another reporter library.

Derived Sequences

The term "derive" should be interpreted broadly as providing a plurality of oligonucleotides with the same or similar information contents as the original plurality of oligonucleotides.

Thus, an original oligonucleotide may be manipulated in any desirable ways such that the resulting oligonucleotide is derived from the original oligonucleotides. Likewise a plurality of oligonucleotides may be manipulated in any desirable ways such that the resulting plurality of oligonucleotides is derived from the original plurality of oligonucleotides.

The derived plurality of oligonucleotides may be the PCR-product of the original plurality of oligonucleotides. It may also be the ligation product or restriction product of the original plurality of oligonucleotides. It may also be the product of other enzymatic and chemical reactions. Moreover, a single-stranded oligonucleotide may be converted to a double-stranded oligonucleotide and a double-stranded oligonucleotide may be converted to a single-stranded oligonucleotide. Furthermore, a first single-stranded oligonucleotide may be converted to a second single-stranded oligonucleotide complementary to the first oligonucleotide.

Deriving may also mean providing a plurality of oligonucleotides with the same or similar information contents as the top 50% of the oligonucleotide species of highest concentration and/or weight % in the starting material, such as the top 40%, 30%, 20%, 10%, 5%, 3%, 2%, 1%, 0.1%, 0.01%, 0.001%, 0.0001% or 0.00001%, such as the top 0.000001% of the oligonucleotide species of highest concentration and/or weight % in the starting material.

Deriving may comprise processes such as amplification and dilution. Moreover, deriving may comprise analysing the contents of the starting material and e.g. synthesising or mixing a library with the same or similar composition.

When the original plurality of oligonucleotides is a plurality of non-natural oligonucleotides that are resistant to enzymatic manipulation such as e.g. amplification by a polymerase, a plurality of amplifiable oligonucleotides derived from said original non-amplifiable plurality of oligonucleotides may be prepared by hybridizing a plurality of oligonucleotides to the original plurality of oligonucleotides and selecting hybridized oligonucleotides are amplifiable.

In this way, the information content of a plurality of non-natural oligonucleotides is transferred to another plurality oligonucleotide species which can be manipulated further using molecular biology techniques such as DNA sequencing, DNA amplification, cloning etc. The derived plurality of oligonucleotides, i.e. reporter sequences, can be evolved as will be apparent from the specification of the present invention.

Thus, in one embodiment, a library of reporter sequences is a copy of the genetic information of an original library of oligonucleotides. The copy may be prepared enzymatically by using a polymerase. The copy may also be prepared by hybridisation of a plurality of oligonucleotides and selection of those oligonucleotides that have hybridised to the original library of oligonucleotides. As outlined above, this method of preparing a library of reporter sequences is preferred when the original library of oligonucleotides is resistant to enzymatic manipulation. This is e.g. the case the oligonucleotides of the original plurality of oligonucleotides comprises non-natural oligonucleotides that cannot be copied or amplified enzymatically.

Fractionations

In a preferred embodiment, the library of oligonucleotides has been fractionated according to activity. A preferred activity is affinity toward a molecular target, i.e. the method is used to identify ligands.

Thus, in one embodiment of the method of specifically amplifying the sequence of a hybridized oligonucleotide specie, the library of oligonucleotide species has been fractionated against a target. Preferred targets are biological molecules of therapeutic relevance, such that identified ligands are of potential therapeutic interest e.g. as drugs or lead compounds. Preferred targets are e.g. proteins such as receptors, interleukins, cytokines, antibodies etc. Also cellular nucleic acids such as microRNAs, rRNAs, tRNAs, mRNAs etc. may be used as target. If the target is a cellular nucleic acid, and the library is a library of encoded compounds, it is preferred that oligonucleotides of the library are double stranded, such that the oligonucleotides will not base pair with the target nucleic acid.

Preferably, the target has been or can be immobilized.

In the present context, the term fractionation and selection are used interchangeably.

A preferred fractionation method comprises the steps of contacting the library with an immobilised target (or a target that can subsequently be immobilised) and one or more washing steps.

In a fractionated library, library species having a particular activity are overrepresented or have been enriched relatively to library species without the particular activity.

Preferred reporter libraries of the invention, have been derived from libraries of oligonucleotides that have been fractionated.

Selections and in particular those based on affinity, are well known to the skilled person. One advantage of such selections is that a library can be counter selected against other targets. Thus, if the desired candidate compounds should bind to target 1, but not target 2, the library would be selected against target 2 in a first selection. Then the eluate of that selection (the non-bound library species) would be selected against target 1 in a second selection. The library species binding to target 1 in the second selection would then be negative for binding activity against target 2. Hence, such selections allow selection for sub-type specificity, which is often desired for therapeutic lead compounds. I.e. the lead compounds should bind e.g. to one receptor, but not to another related receptor.

Selections against non-biological targets are also contemplated. It is e.g. presumed that new high-affinity ligands identified by the presented methods will be of value in the field of nanotechnology.

Highly specific selections (or fractionations) in which a high fold of enrichment is achieved can be done in various ways. Suitable conditions for contacting the library with the target vary and depend on the particular target and the particular library. Optimization of such conditions is well known to the skilled man.

In addition to optimizing the conditions of contacting the library with the target, several other methods may be employed for improving the fold of enrichment (increasing the signal-noise ratio). One method is by specific elution. Thus, soluble target can be used for elution, which has the advantage that library species bound non-specifically to the solid support or the test tube is not eluted. Also, a known ligand of the target may be used for specific elution. This is particular favorable if candidate compounds is sought, which binds to the same pocket on the target as the known ligand.

Still another method includes elution of the target from the solid support, thereby eluting candidate compounds bound to the target.

Another preferred method relates to fractionation of libraries of encoded compounds. In this embodiment, the identifier sequence and the candidate compound is connected by a linker, said linker comprising a release group. The release group may be restriction site cleavable by a restriction enzyme. Another preferred release group is a photocleavable bond. In this embodiment, the library is fractionated against the target and after a number of washing steps; identifier sequences are eluted using the release group.

Thus, sequences selected because of activity in the identifier sequence are not eluted. On the other hand, encoded compounds selected because of activity residing in the candidate compound will release the identifier sequence from the solid support if the release group is used. This will give an improved fold of selection.

Still another method of improving the selection is by use of iterated selections of the same library. Thus, a first selection results in an enriched library. Then the enriched library is again selected against the target to give a further enriched library and so forth. A potential problem with these iterated selections is obviously that each selection round will be accompanied by a certain loss, which will limit the number of rounds applicable. In other words, this strategy requires a copy number of library species that will ensure the survival of the library species with specific activity.

The Signal-Noise Problem

Regardless of the selection method used, a signal-noise problem may still be present, i.e. there will be too many library members who are not active or functional with regards to the desired activity, e.g. affinity against a particular target. The signal-noise problem will be especially prominent for large libraries with a low number of individual library members. Consider a theoretical example where a library comprising 10.000 copies of each of $10^{12}$ library members. This library may be selected such that only $10^8$ molecules remains, in which active library members are buried. I.e. the total number has gone from $10^{16}$ to $10^8$, which is a dramatic selection of $10^8$. Even so, the task of identifying active library is still immense, as the library will roughly contain 10.000 non-active library members for each active library member. In other words, if identification is done by cloning, 10.000 clones will have to be sequenced to identify the active library members. And still it will not be possible to deduce that the particular sequence actually corresponds to an active library member, as it is still not known that the particular sequence is overrepresented among the clones.

Consider further an example of a library comprising 100.000 copies of each of $10^{10}$ library members. This library may be selected such that only $10^7$ molecules remains, in which active library members are buried. I.e. the total number has gone from $10^{15}$ to $10^7$, which again is a dramatic selection of $10^8$. Even so, the task of identifying active library is still cumbersome, as the library will roughly contain 100 non-active library members for each active library member. As outlined above, sequencing of 100 clones will identify the active library, but will not be possible to deduce that the particular sequence actually corresponds to an active library member, as it is still not known that the particular sequence is overrepresented among the clones. To get this information, 500 or 1000 clones will have to be sequenced.

It is an object of the methods of the present invention to allow identification of active library members, even if non-active library members outnumber them, i.e. the signal-noise does not allow facile identification as outlined above.

Method of Amplifying Hybridized Sequences

The present invention provides methods of manipulating the information content of a plurality of oligonucleotides. E.g. methods are provided that allow identification of the most abundant oligonucleotides among a plurality of oligonucleotides. Moreover, the invention provides methods of identifying new molecular activity that may be of relevance for the development of new therapeutics or for the field of nanotechnology.

In one aspect, the present invention provides a method of specifically amplifying the sequence of a hybridized oligonucleotide specie comprising the steps:

a. Incubating a plurality of oligonucleotides under conditions of hybridisation
b. Extending the 3' end of one or more hybridised oligonucleotide species, such that the extended region generate a new primer binding site
c. Amplifying extended sequences using said new primer binding site
d. Optionally identifying the identity of amplified sequences thereby revealing the identity of hybridised oligonucleotide species in step a It is to be understood that the oligonucleotide specie of the above method is not a PCR primer. Note, that the sequence of a PCR primer is not amplified during PCR. This may be better understood by considering a typical PCR, where 20-pmol primer is used and hence 20 pmol of the primer sequence is present. This number will stay constant during PCR, as the number of primer sequences is the sum of free primers and extended primers (PCR-product).

Figure 17:
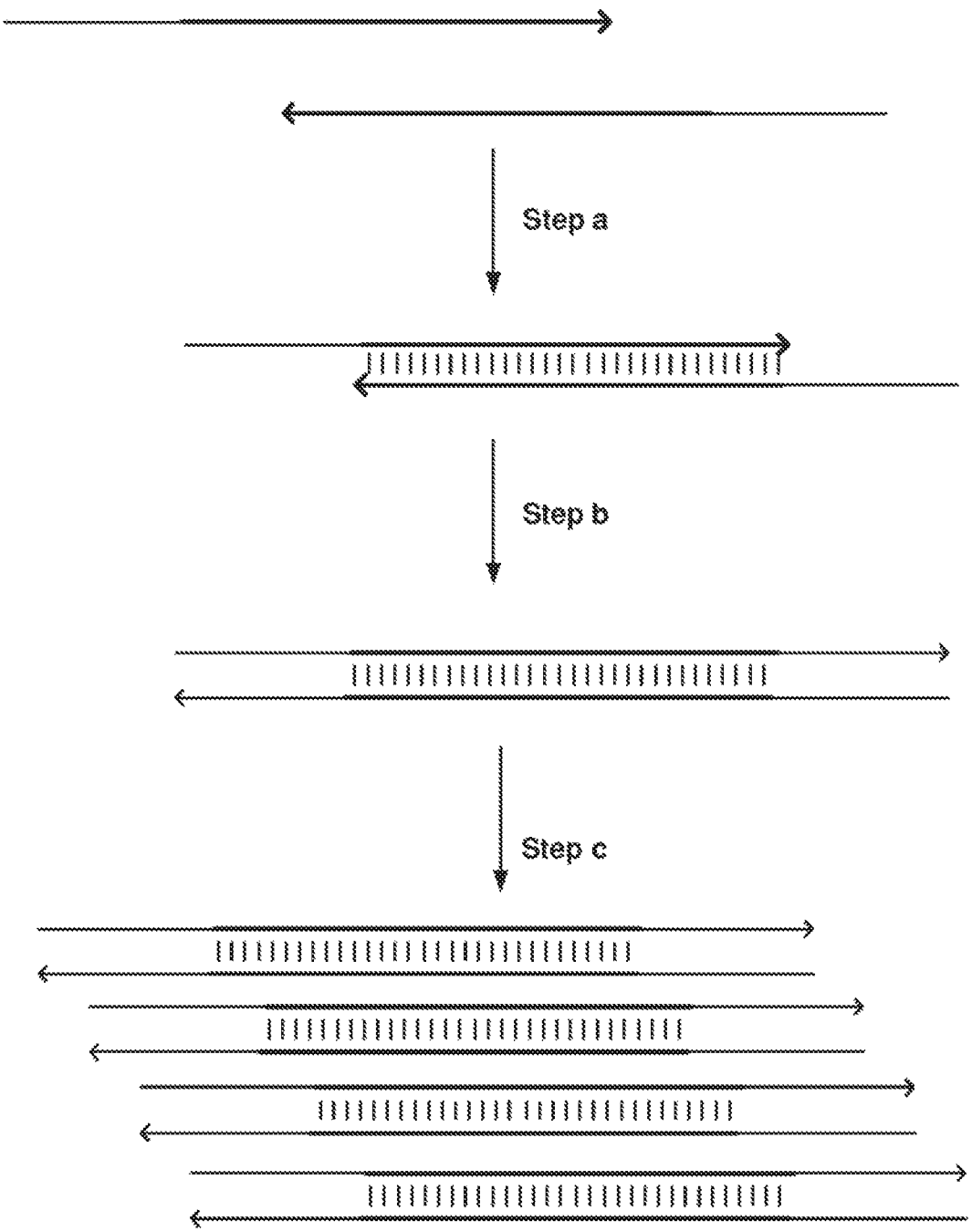
FIG. 17 illustrate the principle of the method of amplifying hybridised sequences.

The Principle of the Method is Shown in FIG. 17

In a preferred embodiment, the plurality of oligonucleotides comprises a library of oligonucleotides.

In a preferred embodiment, the library of oligonucleotides is a library of aptamers.

In another preferred embodiment, the library of oligonucleotides is a library of encoded compounds.

In still another embodiment, the library of oligonucleotides is a library of reporter sequences.

Step d of the method can be done by cloning of the sequences of step c and DNA-sequencing of individual clones. The skilled man knows such methods.

In one embodiment of the method of specifically amplifying hybridised sequences, step b is followed by a step of denaturation.

In one embodiment, extension of the 3' end of a hybridised oligonucleotide is done by a heat stable polymerase, which is also used for PCR. In another embodiment, extension is done by a heat sensitive polymerase such as the Klenow fragment. The polymerase may have proofreading or may not have proofreading. A polymerase with proofreading may favour extension and amplification of hybridised sequences without mismatches.

In another embodiment, one or more of the oligonucleotide species are RNA molecules and the polymerase used for extension of the 3' end is a primer dependent RNA polymerase or a reverse transcriptase.

In one embodiment of the method of specifically amplifying the sequence of a hybridised oligonucleotide specie, step c is followed by separation of extended oligonucleotide species from non extended oligonucleotide species. One preferred method for separation of extended oligonucleotide species from non-extended oligonucleotide species is digestion of single stranded DNA. Another preferred method is primer extension with a biotin containing primer hybridising to the newly formed primer binding site followed by purification using binding to streptavidin.

In still another embodiment, step b is followed by a denaturation step before step c.

In another embodiment of the method of specifically amplifying the sequence of a hybridised oligonucleotide specie, step a is followed by a fractionations step to fractionate hybridized oligonucleotides from non-hybridized oligonucleotides. Preferably, the fractionations step is performed before step c.

Amplification

The basic idea of the method is that only oligonucleotides that have hybridised are capable of amplification.

Amplification as used in the present context generally refers to any method of increasing the copy-number of the sequence of one or a plurality of oligonucleotides. When referring to an encoded compound, only the sequence of the identifier sequence is amplified and not the encoded compound.

A preferred amplification method of the invention is the polymerase chain reaction (PCR).

Thus, in a preferred embodiment, the amplification of step c is done by PCR.

In another embodiment, the product of step b is amplified by cloning into a host. More specifically, the plurality of oligonucleotides may be cloned in e.g. pUC18 or pUC19, where the copy number will go from 1 to 3-500 as the recombinant plasmid is propagated in the bacteria. Growing the bacteria to obtain many bacteria of each clone can increase the copy number further. In this embodiment, the extended 3' end generates a double-stranded restriction site, which is used for cloning. Preferably, the hybridizing oligonucleotides each have its 3' end extended to generate a first and a second restriction site for directional cloning. It will be apparent to the skilled man that a single stranded restriction site will not be a substrate for most restriction enzymes, and that single-stranded oligonucleotides will be poor substrates for ligation. Therefore, the generation of double-stranded restriction sites can be used for amplification of hybridised oligonucleotides.

In still another embodiment, transcription is used for amplification. In this embodiment, the product of step b generates a double-stranded RNA polymerase promoter. In this method, one of the fixed sequences harbours a promoter for a RNA polymerase such as T7 or SP6 RNA polymerase, such that the sequences of hybridised oligonucleotides can be amplified by transcription. If desired, the resulting library of RNA molecules can subsequently be reverse transcribed into DNA and one or more fixed sequences can be added by ligation.

To be amplifiable by exponential PCR, an oligonucleotide needs two fixed sequences that can be used as primer binding sites. In a preferred embodiment of the method, a second fixed sequence can only be formed if the oligonucleotide has hybridised to a complementary oligonucleotide.

The Principle is Illustrated in FIG. 17

The term PCR amplification as used in the present context generally refers to exponential PCR amplification. If the reaction is carried out to amplify sequences linearly, it will be specifically mentioned as linear PCR amplification.

In linear PCR amplification, the same primer-binding site is repeatedly used for the generation of a copy, i.e. a primer is annealed into the primer-binding site, the primer is extended, where after a new primer is annealed in to the same primer binding site for a next round of linear amplification.

Hybridisation

In one embodiment of the method of specifically amplifying the sequence of a hybridised oligonucleotide specie, hybridisation and PCR is carried out in situ. One such example is detection of hybridisation to a microarray. Thus hybridisation of one oligonucleotide specie or a plurality of oligonucleotide species to complementary counterparts on a microarray is followed by in-situ PCR.

In one such embodiment, not all oligonucleotides species of the plurality of oligonucleotides species are represented on the microarray, as the goal of the method may be to confirm the presence of particular oligonucleotides species among the plurality of oligonucleotide species.

In another embodiment of the method, hybridisation is carried out in solution. Thus, a plurality of oligonucleotides is present in solution and incubated under conditions of hybridisation. After hybridisation, the 3' end of hybridised oligonucleotides are extended to generate a second fixed sequence (i.e. a new primer binding site) in the same oligonucleotide species, where after these sequences are exponentially amplified, preferably by PCR. In this way, hybridised sequences are enriched relatively to non-hybridised sequences.

Step a) of the method of specifically amplifying hybridised oligonucleotides is typically done such as to optimize specific hybridisation. Appropriate conditions depend on the type of oligonucleotides that are to hybridise and generally longer oligonucleotides will require higher temperature and/or lower salt concentration. Also formamide is often used to decrease the melting temperature of oligonucleotides. Generally a temperature around the melting temperature is desired for specific hybridisation. Conditions for specific hybridisation are well known in the art. In the method, conditions need not necessary be optimised for specific hybridisation. In fact, the method can also be employ conditions where a significant degree of faulty hybridisation occurs, as will be evident from the examples.

Also the time for hybridisation is a parameter adjustable to fulfil different needs. If e.g. it is desired to favour high abundant oligonucleotide species, the hybridisation time can be relatively short, i.e. such that only the most abundant oligonucleotide species will hybridise, whereas low abundant oligonucleotide species will not find complementary low abundant counterparts. In this case, the hybridisation reaction is kinetically controlled.

On the other hand, the hybridisation reaction can be done to completion, such that all oligonucleotide species have hybridised to a complementary counterpart if a complementary counterpart is present.

In one embodiment, the hybridisation reaction may be done immediately before PCR. In this embodiment, the hybridisation reaction may be done in the PCR reaction mix such that PCR is performed immediately following hybridisation. In fact, a typical PCR can be performed on the plurality of oligonucleotides, which will then hybridise during PCR.

In another embodiment, a prolonged hybridisation time is used, Such prolonged hybridisation time may be 12 hours, 18 hours, 24 hours, 30 hours, 36 hours, and 42 hours such as 48 hours or 72 hours.

Evolution of a Reporter Library

In a preferred embodiment of the method of specifically amplifying the sequence of a hybridised oligonucleotide specie, the amplified extended sequences of step c, or oligonucleotide species derived thereof, is comprised in a plurality of oligonucleotides used in a next round of steps a-c, such that an iterative process is initiated, wherein each repetition of steps a, b and c is optionally followed by step d.

Figure 8A:
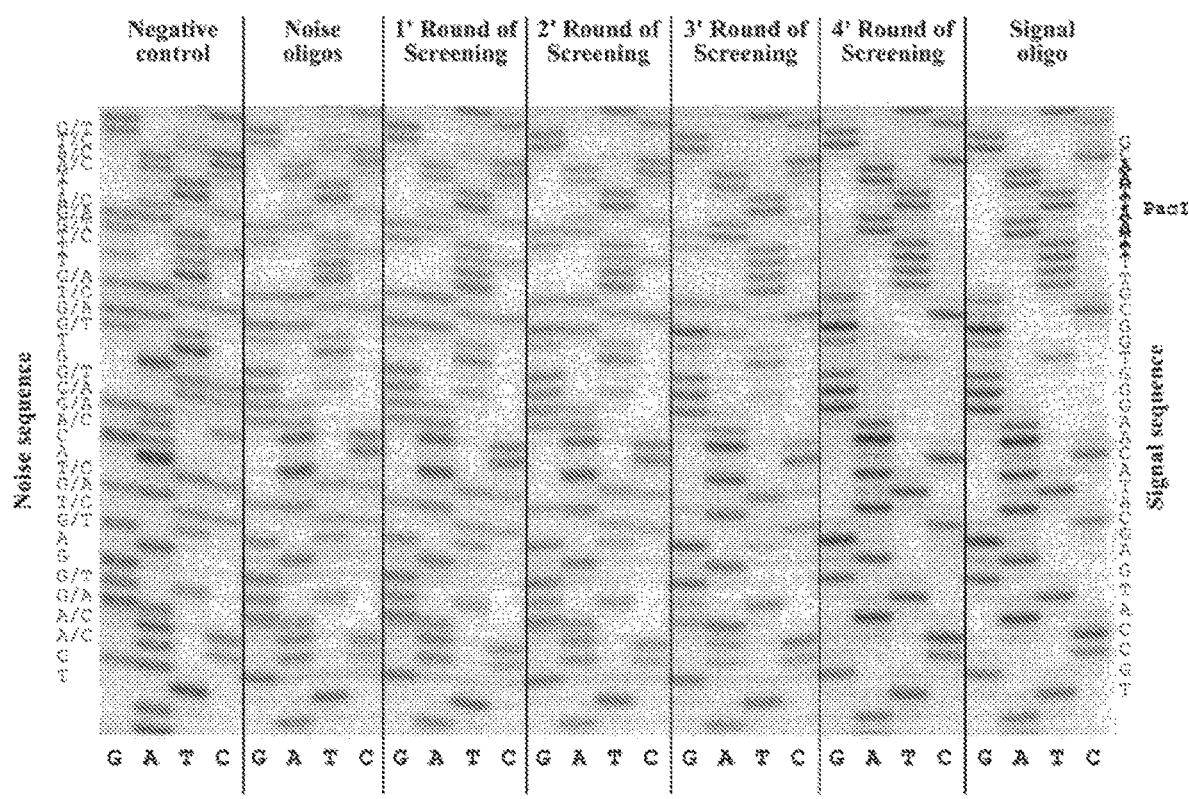
Figure 8B:
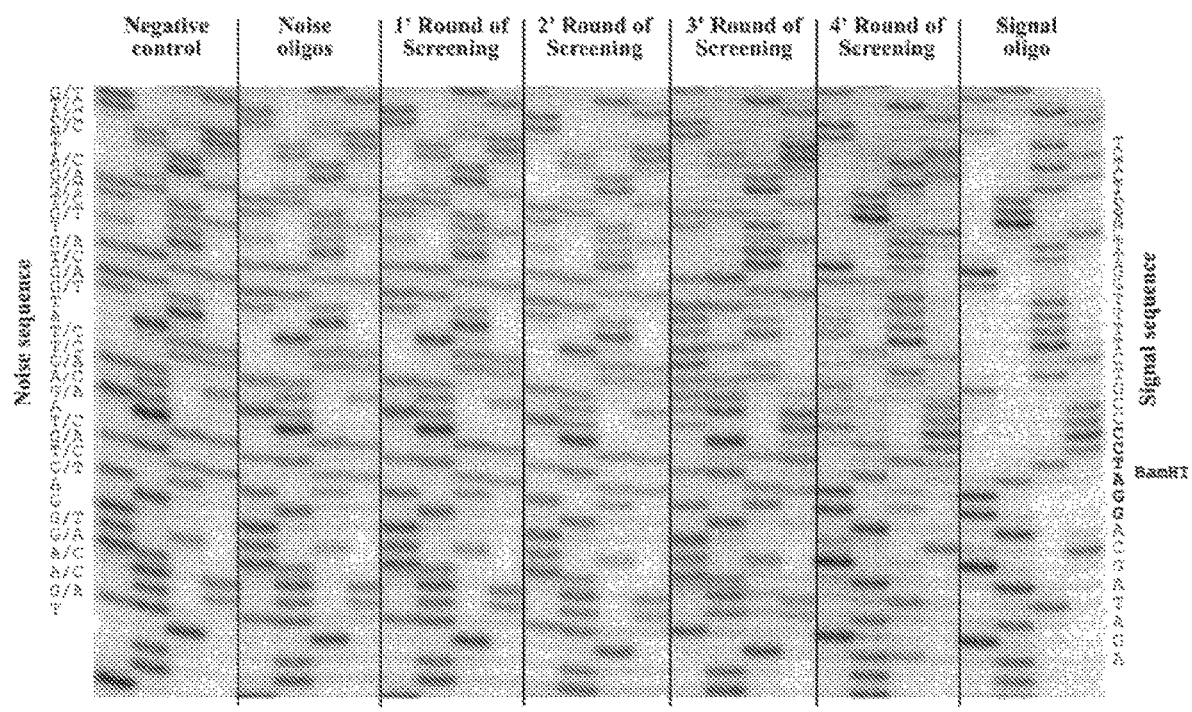

FIGS. 8A and 8B relating to example 2 shows how the sequence of a reporter library evolves for each round.

By repetition of the steps a, b, and c, the plurality of oligonucleotide species or nucleic species derived thereof, may start to evolve. That is to mean that the information content of the plurality of oligonucleotide will change. E.g. some oligonucleotides species will increase in abundance relatively to others, whereas other oligonucleotide species will decrease relatively to others. The abundance may also be expressed relatively to the total abundance of oligonucleotide species. Thus, the information content, as used in relation to a plurality of oligonucleotides, contains not only the genetic information of individual oligonucleotide species, but also the abundance of individual oligonucleotide species relatively to the rest of the oligonucleotides species.

The plurality of oligonucleotides that is evolving will in the present context also be termed a reporter library, as will be apparent from the description of reporter sequences earlier in the specification.

While the information content of the reporter library changes as the rounds proceed, the last generation reporter library is still derived from the previous generation reporter libraries Evolution of a reporter library has been described in patent application PCT/DK2004/000325 (Selection and evolution of chemical libraries). A critical point of the technology described in the aforementioned application is the specific amplification of only hybridized sequences. If also non-hybridised oligonucleotides are amplified, the so-called information transfer will be blurred. In other words, 99% of the amplified information may stem from non-hybridised sequences, wherefore the resulting library will not reflect what happened in the hybridization reaction. It is an object of the method of specifically amplifying the sequence of a hybridised oligonucleotide specie to solve this problem.

In a preferred embodiment of the method of specifically amplifying the sequence of a hybridised oligonucleotide specie, the iterative process comprise at least two repetitions of steps a, b and c and optionally step d. In other embodiments, the iterative process comprise respectively 3, 4, 5, 6, 7, 8, 9, 10, 11, 12, 13, 14, 15, 16, 17, 18, 19, 20, 25, 30 repetitions. The number of repetitions may depend on the how much it intended to evolve the plurality of oligonucleotides.

In one embodiment, it is desirable to continue evolution of the reporter library until only 10 species remains. In other embodiments, it is desirable to continue evolution until the number of oligonucleotide species remaining is less than respectively 20, 30, 40, 50, 60, 70, 80, 90, 100, 110, 120, 130, 140, 150, 175, 200, 250 and 300.

In another embodiment, is it is desirable to continue evolution of the reporter library until sequencing of 100 clones in step d) identifies less than 100 species. In other embodiments, it is desirable to continue evolution until the number of oligonucleotide species identified when sequencing 100 clones in step d) remaining is less than respectively 90, 80, 70, 60, 50, 40, 30, 25, 20, 15, 14, 13, 12, 11, 10, 9, 8, 7, 6, 5, 4, 3, 2 and 1 specie.

In still another embodiment, is it is desirable to continue evolution of the reporter library until sequencing of a number clones in step d) identifies less species than the number of clones sequenced. Thus, the number of species identified may be smaller by a factor of 100 as compared to the number of clones sequenced in step d), and in other embodiments smaller by a factor of respectively 90, 80, 70, 60, 50, 40, 30, 25, 20, 15, 14, 13, 12, 11, 10, 9, 8, 7, 6, 5, 4, 3 and 2.

Preferably, the remaining species is reporter sequences of the most abundant library members of the original library of oligonucleotides.

Thus, if the original library of oligonucleotides had been fractionated for affinity against a molecular target, the remaining reporter sequences will identify the original oligonucleotides that bound specifically to the target.

In one embodiment of the method, the library of reporter sequences is evolved, i.e. the relative ratios of the oligonucleotide species change for each repetition of the steps a, b and c, because kinetics of hybridisation will favour high-abundant oligonucleotide species in the hybridisation reaction, i.e. the hybridisation reaction is kinetically controlled.

In another embodiment, the relative ratios of the most abundant oligonucleotide remains essentially unchanged, because the most abundant oligonucleotide species are hybridised to completion, i.e. the hybridisation reaction is not kinetically controlled for the most abundant oligonucleotides species. In this embodiment, the most abundant oligonucleotide species are defined by the hybridisation reaction and the time of hybridisation. Thus, in this embodiment, the most abundant oligonucleotide species are those, which are not kinetically controlled in their hybridisation reaction. This is contrary to the situation where the most abundant oligonucleotide species are predetermined and the hybridisation reaction and the time of the hybridisation reaction adjusted accordingly. This latter described situation is difficult, because the actual abundance (or concentration) of library species is most often unknown.

Estimating Complexity

The complexity of a plurality of oligonucleotides may be estimated e.g. by measurements of renaturation time. When referring to the complexity of a plurality of oligonucleotides, what is meant is the number of oligonucleotides species, the amount (or copynumber) of each oligonucleotide specie and in some embodiments, also the sequence similarity between the oligonucleotide species. An assessment of the complexity is useful for adjustments of hybridizations times and in determining whether a reporter library evolves and whether the process should be stopped.

Thus, in one embodiment, the complexity of a plurality of oligonucleotides is estimated by renaturation measurements. In one such embodiment, the plurality of oligonucleotides is a reporter library, which is denatured, where after the denatured reporter library is incubated under conditions of hybridization. Measuring the change in absorption at 260 nm can then be used to follow renaturation. Such renaturation experiments are well known to the skilled man and has been used extensively e.g. in connection to estimating the complexity of the human genom.

The complexity of the plurality of oligonucleotide species may also be measured drawing advantage of the method of specifically amplifying the sequence of a hybridised oligonucleotide specie.

In one embodiment, the plurality of oligonucleotide species is a reporter library in the form of a PCR product. The reporter library is manipulated such that only hybridized sequences can be amplified by PCR. Such manipulation is typically done by removing primer binding sites from the reporter library. In one embodiment, the reporter library is split into two, where after the upstream primer binding site is removed from one subset of the library and the downstream primer binding site is removed from the other subset of the library. Restriction digestion is used for removing the primer binding site. After removing the primer binding sites, single-stranded oligonucleotides may be purified, where after the subsets are combined again. Alternatively, the double-stranded subsets are combined. Either way, only hybridized oligonucleotide species will be exponentially amplifiable by PCR. Thus, the plurality of oligonucleotide species is now incubated under conditions of hybridization and a quantitative PCR (qPCR) reaction is performed. Since the number of hybridized oligonucleotide species is a function of the time of hybridization and the complexity of the plurality of oligonucleotides, qPCR actually gives an estimate of the complexity of the plurality of oligonucleotides.

Thus, in one embodiment of the method of specifically amplifying the sequence of a hybridised oligonucleotide specie comprising, a qPCR is performed on at least a subset of the extended sequences of step to estimate the complexity of the plurality of oligonucleotide species.

The qPCR may be the PCR of step c, or it may be a PCR performed in parallel.

Removing a Fixed Sequence

In a preferred embodiment of the method, the plurality of oligonucleotides comprise oligonucleotide species that are characterised by having only one fixed sequence, and thus are not inherently capable of exponential amplification by PCR. As the skilled man will appreciate, exponential amplification by PCR requires two fixed sequences.

In another embodiment, the amplification product of step a, is enzymatically digested to remove a fixed sequence site before continuing with the next round. Such enzymatic digestion requires the presence of a restriction site between the fixed sequence and the hybridizing region. The purpose of removing the fixed sequence is to generate an oligonucleotide specie, which is only capable of amplification by exponential PCR if it is or has been hybridized to a complementary sequence.

After digestion, the resulting oligonucleotide specie may be purified e.g. using HPLC or other means e.g. polyacrylamide gel electrophoresis (PAGE) followed by elution from the gel. Still other means involve the use of biotin containing primers in the PCR. If one of the primers used for PCR contains a biotin in its 5' end, the resulting PCR product can be immobilized on streptavidin beads. Digestion of the PCR product on beads will then release oligonucleotide species with only one fixed sequence, as the other fixed sequence will be attached to the streptavidin beads. In another embodiment, a photocleavable biotin group is used. In this embodiment, the PCR product is immobilized on streptavidin beads. Then one fixed sequence is released from the streptavidin beads by restriction digestion. The resulting double-stranded oligonucleotide is then denatured to separate the non-biotin containing strand from the biotin containing strand. After washing off the non-biotin containing strand, the remaining strand can be eluted by photocleavage.

A fixed sequence site may also be removed by other means, e.g. by incorporating uracil into fixed sequences, where after the uracil containing fixed sequence can be removed with Uracil DNA glycosidase. Incorporation of uracil may be done by using uracil containing primers in PCR. This method is particular suited in the embodiment with a preceding linear amplification phase.

In one embodiment, a double-stranded oligonucleotide specie is used for the next round of hybridization.

In another embodiment, a single-stranded oligonucleotide is used for the next round of hybridization.

In one embodiment, the fixed sequence is located on the 5' side of the coding sequence of the oligonucleotide specie.

In another embodiment, the fixed sequence is located on the 3' side of the coding sequence of the oligonucleotide specie.

In a preferred embodiment, the fixed sequence does not engage in hybridization. In this embodiment, the plurality of oligonucleotides preferably does not contain sequences complementary to the fixed sequence.

In still another preferred embodiment, the plurality of oligonucleotides is a mixture of oligonucleotide species with the fixed sequence on the 5' side of the coding region and on the 3' side of the coding region, respectively.

Preceding Linear Amplification Phase

In another preferred embodiment of the method of specifically amplifying the sequence of a hybridised oligonucleotide specie, step b is preceded by a phase of linear amplification.

Figure 18:
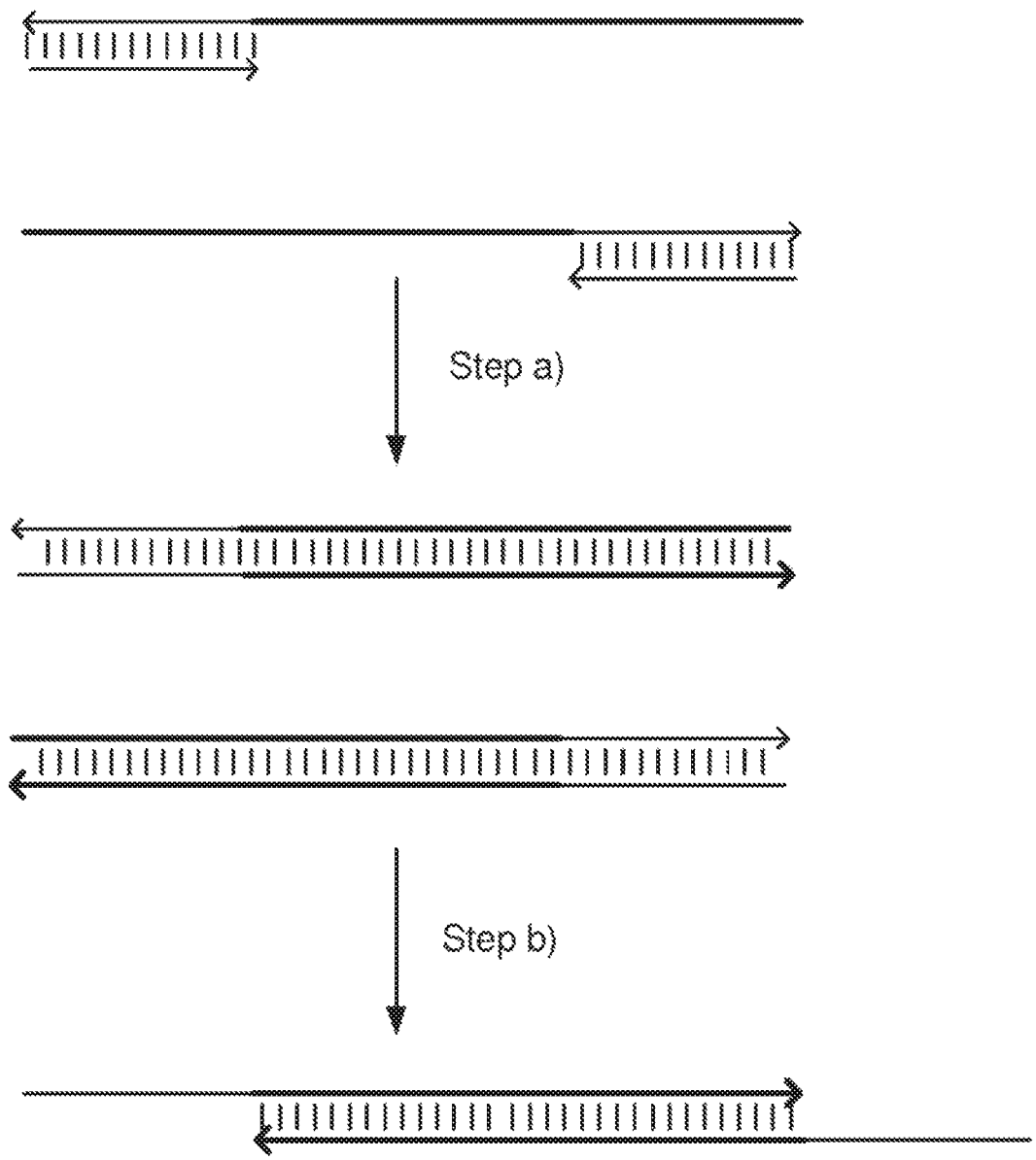
FIG. 18 illustrate the principle of a linear amplification phase.

In this embodiment, the plurality of oligonucleotides comprise oligonucleotide species with the fixed sequence on the 3' side of the coding region. Linear amplification of these oligonucleotide species result in oligonucleotide species that have a fixed sequence on the 5' side of the coding region. This principle is illustrated in FIG. 18.

Targeted Amplification

In another embodiment of the method of specifically amplifying the sequence of a hybridised oligonucleotide specie, the plurality of oligonucleotides comprise a mixture of oligonucleotide species that are inherently amplifiable by exponential PCR and oligonucleotide species that are not inherently amplifiable by exponentially PCR. In this embodiment, PCR primers can be chosen such that only a subset of the oligonucleotides can be amplified. Thus, a first strand of a hybridised complex may be amplified, whereas the second strand is not. In this embodiment, the second strand may indeed contain two fixed sequences, but they are not used in PCR because the used primers do not fit both fixed sequences (the fixed sequences are not target for amplification). Preferably, the oligonucleotide species that are inherently non-amplifiable by exponential PCR are oligonucleotides species with only one fixed sequence. Preferably, exponential amplification is performed with primers chosen such as to only amplify hybridised oligonucleotides species that are not inherently exponentially amplifiable by PCR.

Dilution

In one particular embodiment of method of specifically amplifying the sequence of a hybridised oligonucleotide specie, the amplification product of step c is diluted such as to lose sequences (oligonucleotide species) corresponding to non-hybridised oligonucleotides. Not to be bound by theory, this may be better understood with a theoretical example; consider a situation where 1 in 1.000 oligonucleotide species have hybridised. Hybridised sequences have then been amplified $10^6$ fold, where after the ratio of hybridised sequences (or copies thereof) to non-hybridised sequences are 1000 to 1 (or $10^6$ to 1000). Note that non-hybridised sequences have not been physically separated from hybridised sequences. If this plurality of sequences is now diluted e.g. 100 fold, 99 of 100 non-hybridised sequences are lost, without losing the hybridised sequences. Note that 99 of 100 of the hybridised sequences are of course lost, but since there is 1000 of each species, the specie will survive. Obviously, amplification before dilution may be omitted.

In one embodiment, the ratio of hybridised sequences to non-hybridised sequences is assessed using quantitative PCR (qPCR), as outlined above for measurements of complexity of a plurality of oligonucleotides. Thus using qPCR the amount or number of template sequences (i.e. hybridised sequences) can be determined and this number can be held up against the total number of oligonucleotides present in the plurality of oligonucleotides to assess the fold of dilution that is to be used.

Thus, the eliminating non-hybridised sequences can be done using the steps of:
 a) qPCR of hybridised sequences
 b) Assessing the ratio of hybridised sequences to non-hybridised sequences
 c) Using the information of step b to determine a fold of dilution
 d) Diluting the amplification product of qPCR
 e) Optionally amplifying the diluted amplification product of step d In one embodiment, a range of different dilutions of the plurality of oligonucleotides is used in step a).

In another embodiment, dilution is used to secure that the hybridisation reaction is kinetically controlled. Thus, a series of dilutions may be prepared, and the lowest concentration resulting in amplification product in step c may be used for further steps.

A First and a Second Library of Oligonucleotides

In a preferred embodiment, the plurality of oligonucleotides comprises a first library of oligonucleotides and a second library of oligonucleotides.

In one such embodiment, the first library of oligonucleotides is a library of reporter sequences and the second library is a library of aptamers.

In another such embodiment, the first library of oligonucleotides is a library of reporter sequences and the second library is a library of encoded compounds.

In another such embodiment, the first library of oligonucleotides is a library of reporter sequences and the second library is a library of reporter sequences.

In another embodiment, the first library of reporter sequences are derived from a first library of oligonucleotides and the second library of reporter sequences are derived from a second library of oligonucleotides.

The use of a first and a second library of oligonucleotides or a library of reporter sequences derived thereof may have several advantages. Consider e.g. a first and a second library that is fractionated against a biological target in separate fractionations. Not to be bound by theory, the principle may be illustrated with a theoretical example: Assume the libraries have a diversity of e.g. $10^{10}$, that the copy number of each library specie is $10^4$ and that the library is enriched $10^5$ fold. In other words a $10^5$-fold selection is performed. Thus, 9 in 10 of the library species that is not positively selected (because they do not have any affinity against the target) will be lost from the fractionated library, i.e. 1 in 10 library members with non-specific affinity are lost. This will be true for both the first and the second library. If the sequences of the first library and the sequences of the second library is then hybridised against each other, chances are that library species with non-specific activity will be lost. More specifically, if a particular library species survives fractionation of the first library, chances are 1 in 10 that the same library specie has also survived the fractionation of the second library. Consequently, by cross-hybridising a fractionated first and second library, only library species that have been fractionated in both fractionations will have a chance of finding a complementary sequence and hence stay in the reporter library. In addition to this stochastic principle of losing low abundant library members, also the kinetics of hybridisation may be used to disfavour low abundant library species (reporter sequences).

A preferred embodiment draws use of a first and a second library for identification of aptamers that are typically identified by SELEX. In this embodiment, the first and the second library each comprise e.g. $10^{14}$ or $10^{15}$ species. The first and the second library are then selected separately against a molecular target, whereafter selected sequences are amplified by PCR to e.g. a copy number of $10^6$. In the cross-hybridisation reaction, only aptamers that bound specifically to the target will be able to find a counterpart and hence be comprised in the reporter library derived from the hybridised species of the cross-hybridisation reaction. In a preferred embodiment, only one copy of each specie is present in the first and the second library. The library size may be anything normally used for SELEX. In a preferred embodiment, the libraries only differ from a typical library used for SELEX in that they contain means for removing one fixed sequence.

In another embodiment of the method of specifically amplifying hybridised oligonucleotide species, the first and second library of reporter sequences are derived from the two complementary strands of a PCR product, said PCR product being derived from a library of oligonucleotides. In this way, a first and a second library of reporter sequences can easily be prepared.

Libraries of the Invention

Another aspect of present invention is a library of oligonucleotides adapted for use in the method of specifically amplifying the sequence of a hybridized oligonucleotide specie. Particular embodiments of such a library have been described above in relation to the method of specifically amplifying the sequence of a hybridized oligonucleotide specie In one embodiment, the library of oligonucleotides species is characterized by having only one primer binding site, and thus are not inherently capable of exponential amplification by PCR.

In another embodiment, the library of oligonucleotides species is characterized in that the coding sequence is flanked by one primer binding site at its 3' end one primer binding site at its 5' end and wherein a restriction site is located between the primer binding site at the 5' end and the coding region.

In the context of the present invention, the coding sequence is the sequence, which carries the genetic information characteristic of the particular library specie. Thus, the coding sequence may identify the candidate compound of an encoded compound, it may identify an aptamer or it may be a sequence derived thereof as present in a library of reporter sequences In another embodiment, the coding sequence is flanked by one primer binding site at its 3' end one primer binding site at its 5' end and wherein a restriction site is located between the primer binding site the 5' end and the coding region.

In another embodiment, the coding sequence is flanked by one primer binding site at its 3' end one primer binding site at its 5' end and wherein a restriction site is located between the primer binding site at the 5' end and the coding region and another restriction site is located between the primer binding site at the 3' end and the coding region.

In another embodiment, the coding sequence or the encoded molecules is flanked by a uracil containing region, said uracil containing region facilitating removal of said region from the oligonucleotide specie from the coding sequence.

Subtractive Hybridizations

Third Aspect

A third aspect of the present invention employs hybridization to a library of standard sequences.

In a first embodiment of this aspect, a method for removing non-active library members from a fractionated library of oligonucleotides is provided. Non-active library members may be oligonucleotides that do not have affinity toward a particular target or reporter sequences derived thereof (also referred to as "corresponding to"). As outlined earlier, non-specific binders will typically accompany specific binders in a fractionated library (causing the "signal-noise problem").

In a second embodiment of this aspect, a method for decreasing the concentration range of a reporter library is provided.

In a third embodiment of this aspect, a method of decreasing the concentration range of a library of aptamers or a library of encoded compounds is provided.

Generally, third aspect of the invention comprises the steps of:
a) Providing a first library of oligonucleotides
b) Providing a second library of standard oligonucleotides
c) Incubating the library of step a with the library of step b under conditions of hybridization
d) Selecting the oligonucleotide species of the first library of oligonucleotides that have hybridized with complementary oligonucleotide species of second library or selecting the oligonucleotide species of the second library sequences that have hybridized with complementary oligonucleotide species of the first library.

In preferred embodiments, the selection of step d is done by the method comprising the steps of:
a. Incubating a plurality of oligonucleotides under conditions of hybridisation
b. Extending the 3' end of one or more hybridised oligonucleotide species, such that the extended region generate a new primer binding site
c. Amplifying extended sequences by PCR using said new primer binding site Third Aspect, First Embodiment: Removing Reporter Sequences Corresponding to Non-Binders In the first embodiment of this aspect, a method for removing non-active library members from a fractionated library of oligonucleotides is provided. Thus, the first library is a library of reporter sequences derived from the non-binding fraction of a library of oligonucleotides and the second library is derived from the binding fraction of a library of oligonucleotides, wherein the library of oligonucleotides is a library of aptamers or a library of encoded compounds.

Figure 19:
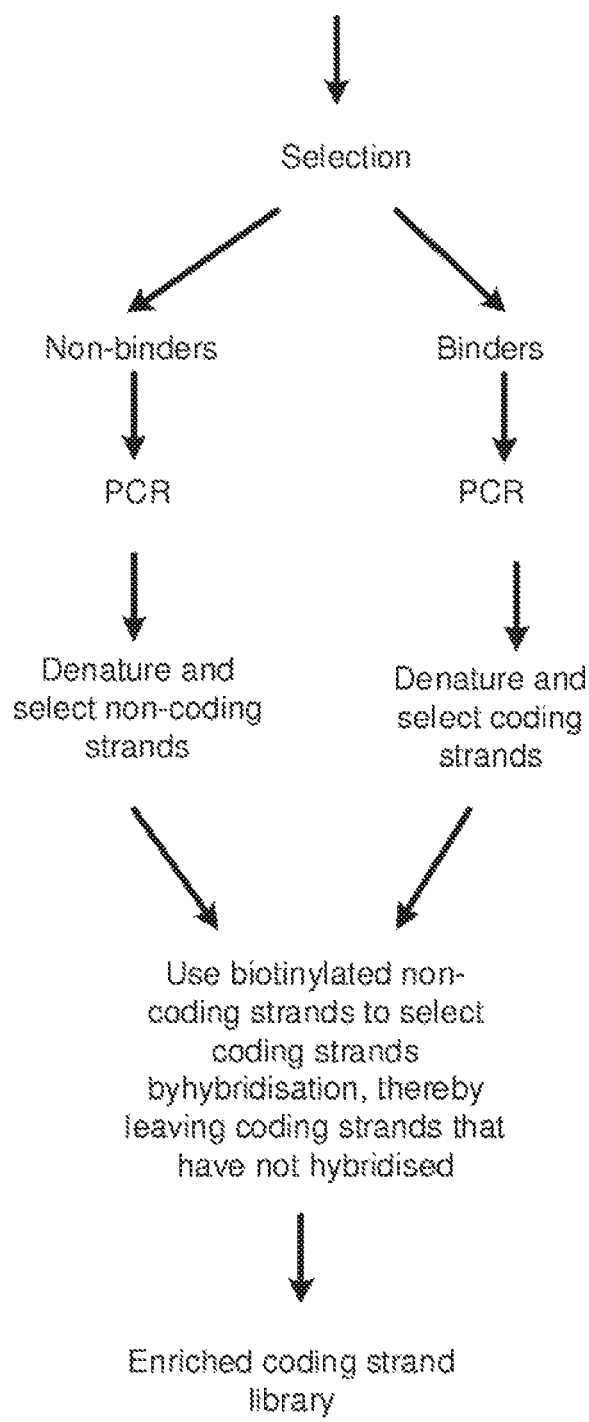
FIG. 19 illustrate the principle of the method of removing reporter sequences from a library of reporter sequences.

The Principle is Illustrated in FIG. 19

As used herein, non-specific binders are library member that do not have significant affinity for the target and a therefore selected primarily because of non-specific interactions for example to the solid support and also to the target. In the present context, they are also referred to as "noise". As used herein, specific binders are library members, which have affinity for the target molecule and are therefore selected primarily because of affinity for the target. Also in the present context referred to as the "signal".

Thus, specific binders will be overrepresented in the binding fraction of a fractionated library. On the other hand, non-specific binders will be overrepresented in the non-binding fraction of a fractionated library. There may e.g. be 1000 copies of each specie corresponding to a non-specific binder in the non-binding fraction, for each 1 copy of the same specie in the binding fraction. Therefore, non-binders of the non-binding fraction may be used to select non-binders of the binding fraction. In doing so, the non-specific binders of the binding fraction can be eliminated.

The first embodiment of the third aspect of the invention may be described as a method of removing sequences corresponding to non-binders in a reporter library comprising the steps:
a. Fractionating a library of oligonucleotides against a molecular target into an binding fraction and a non-binding fraction, wherein the binding fraction contains non-specific binders
b. Generating a library of reporter sequences corresponding to the oligonucleotide species of the binding fraction
c. Generating a library of reporter sequences corresponding to the oligonucleotide species of the non-binding fraction
d. Incubating the library of step b with the library of step c under conditions of hybridization
e. Selecting the oligonucleotide species of the library of step b that have not hybridized with complementary oligonucleotide species of the library of standard sequences Thereby generating a library of reporter sequences corresponding to the oligonucleotide species of the active fraction that has been further enriched in sequences corresponding to specific binders.

Step e) of the method can be done e.g. using a capture group such as biotin on the library of step c. A biotin group can be incorporated using a biotin-containing primer in PCR. Hence, the library of step c can be immobilized on streptavidin, whereby sequences hybridized to the library of step c can also be immobilized, thus allowing selection/purification of sequences that have not hybridized.

Third Aspect, Second Embodiment; Decreasing the Concentration Range

In the second embodiment of the third aspect, the first library of oligonucleotides is a library of reporter sequences that has gone through at least one cycle of selection such that the relative concentration range of at least a fraction the oligonucleotide species of the library has increased.

Figure 20:
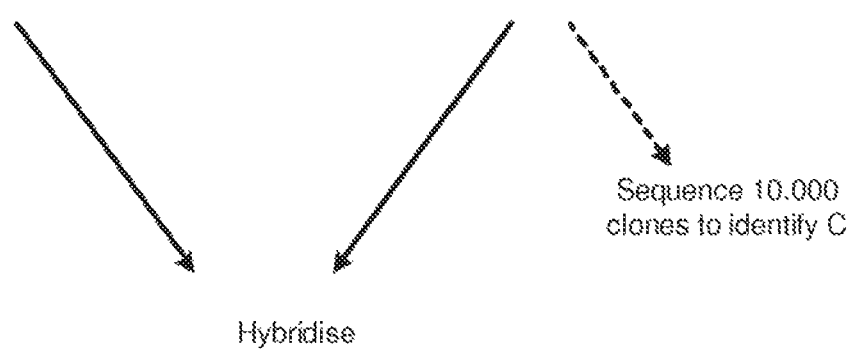
FIG. 20 illustrate the principle of the method of decreasing the concentration range of a reporter library.

The Principle of this Aspect is Outlined in FIG. 20

As described earlier in the specification, evolution of a library of reporter sequence by iterated selections can be performed to increase the "signal-noise" ratio of a plurality of oligonucleotides. At some point during the evolutionary process, all the oligonucleotides in the library may actually represent a signal, i.e. be derived from an encoded compound or aptamer that binds specifically to a target molecule. However, the concentration range of reporter sequences may have expanded during evolution of the reporter library to a degree, where some sequences are in huge excess over others, even though both sequences actually were derived form active library members (e.g. specific binders in an library of encoded compounds or library of aptamers). E.g. a slight excess of 1:2 may have expanded to 1:1000 by evolution of the reporter library. If the concentration range has expanded too much, it will be difficult to identify all sequences corresponding to active library members. In line with earlier explanations in the specification, it will take the sequencing of too many clones. Therefore, it may be desirable to decrease the concentration range.

Thus, a method is provided for decreasing the concentration range of a reporter library comprising the steps of:
a. Providing a library of reporter sequences, wherein said library of reporter sequences has gone through at least one cycle of selection such that the relative concentration range of at least a fraction the oligonucleotide species of the library has increased
b. Providing a library of standard sequences.
c. Incubating the library of step a with the library of step b under conditions of hybridization
d. Selecting the oligonucleotide species of the library of reporter sequences that have hybridized with complementary oligonucleotide species of the library of standard sequences or selecting the oligonucleotide species of the library of standard sequences that have hybridized with complementary oligonucleotide species of the library of reporter sequences.

In another embodiment, the library of reporter sequences has been through at least 2, 3, 4, 5, 6, 7, 8, 9, 10 or 15 cycles of selection.

In another embodiment, the library of standard sequences of step b) is a library of reporter sequences that has gone through less cycles of selection than the library of reporter sequences of step a)

In yet another embodiment, the library of standard sequences is a reporter library directly derived from a library of oligonucleotides selected from the group of a library of encoded compounds and a library of aptamers, i.e. it reflects the initial concentration range of library members.

In another embodiment, the library of standard sequences is a library of oligonucleotide species at equimolar concentrations; they are all present in the same concentration.

In another embodiment, the library of standard sequences is a library of oligonucleotide species with a concentration range of 1:2. That is to mean that the difference in concentration between the specie of highest concentration and the specie of lowest concentration is two-fold. In other embodiments, the concentration range are 1:3, 1:4, 1:5, 1:6, 1:7, 1:8, 1:9, 1:10, 1:20, 1:30, 1:40, 1:50 and 1:100 respectively. A library of standard sequences may be prepared by standard oligonucleotide synthesis. If the coding region of oligonucleotide comprises codons of more than one nucleotide, it may be favorable to use codons as building blocks instead of nucleotides (phosphoramidites)

Third Aspect, Third Embodiment: Balancing a Library of Oligonucleotides

In the third embodiment of the third aspect if the invention, the first library of step a) is a library of aptamers or a library of encoded compounds. Thus, in this embodiment, the method comprises the steps of:
a. Providing a non-fractionated library of aptamers or encoded compounds
b. Providing a library of standard sequences
c. Incubating the library of step a with the library of step b under conditions of hybridization
d. Selecting the oligonucleotide species of the library of step a that have hybridized with complementary oligonucleotide species of the library of standard sequences
e. Thereby generating a library of oligonucleotides that has been reset against the standard library of step b)

Figure 21:
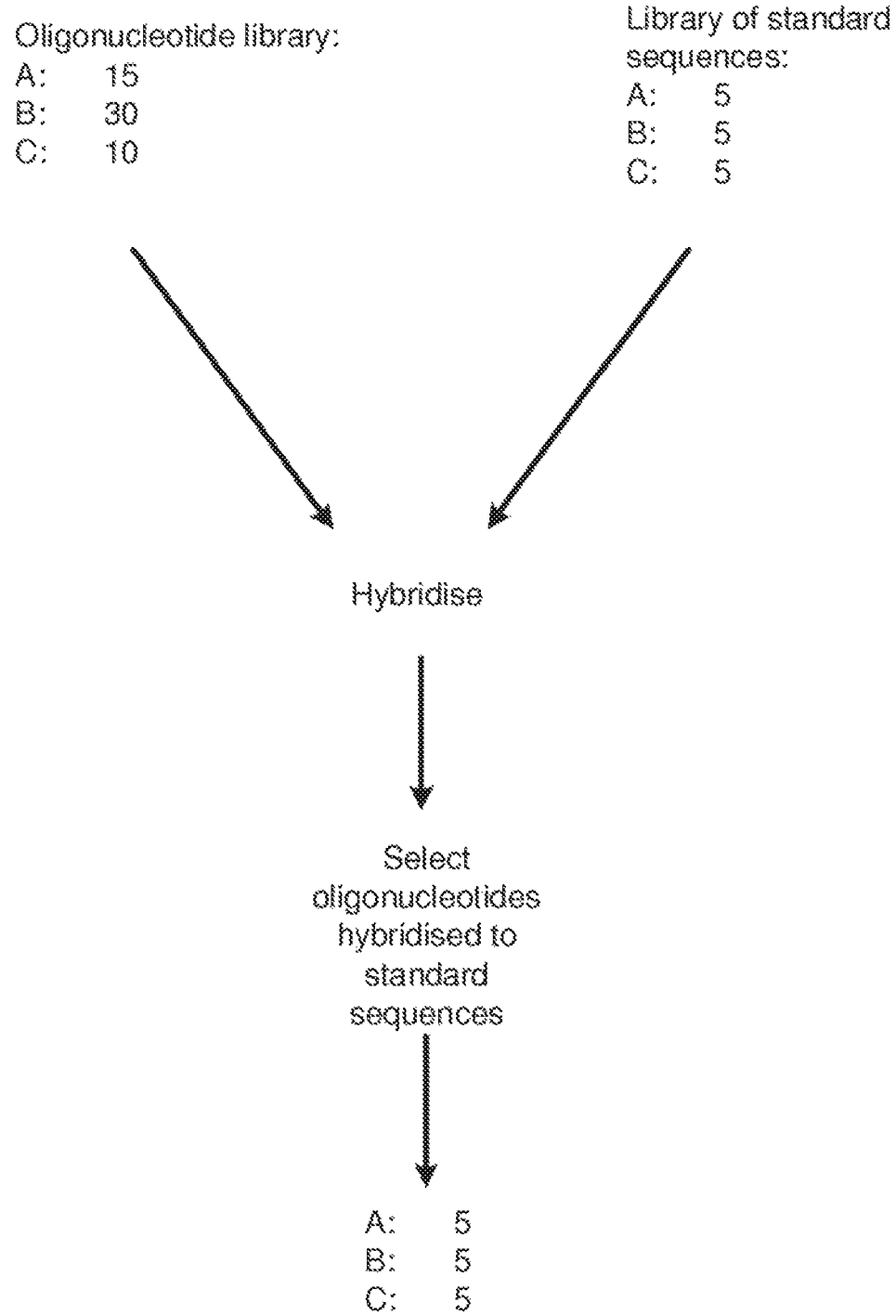
FIG. 21 illustrate the principle of the method of balancing a library of oligonucleotides.

The Principle is Illustrated in FIG. 21

Preferred libraries of aptamers and encoded compounds of the invention have a modest concentration range. Thus, when fractionating the library against a target, the copy number of selected species is preferentially determined by the affinity of the species against the target and not the concentration of the species in the non-fractionated library. Ideally, the concentration of all library members of the original library should be the same, in which case the copy number of selected species will only be determined by affinity. However, for synthetic reasons fluctuations of the copy number of species of the original non-fractionated library will most often vary. Therefore, the concentration range of such a library may be decreased by hybridization to a library of standard sequences. The library of standard sequences can e.g. be prepared using double coupling steps to ensure that a high and reproducible coupling efficiency, which in turn results in a library with only minor fluctuations in concentration.

Specific Amplification Inhibitors

Figure 22:
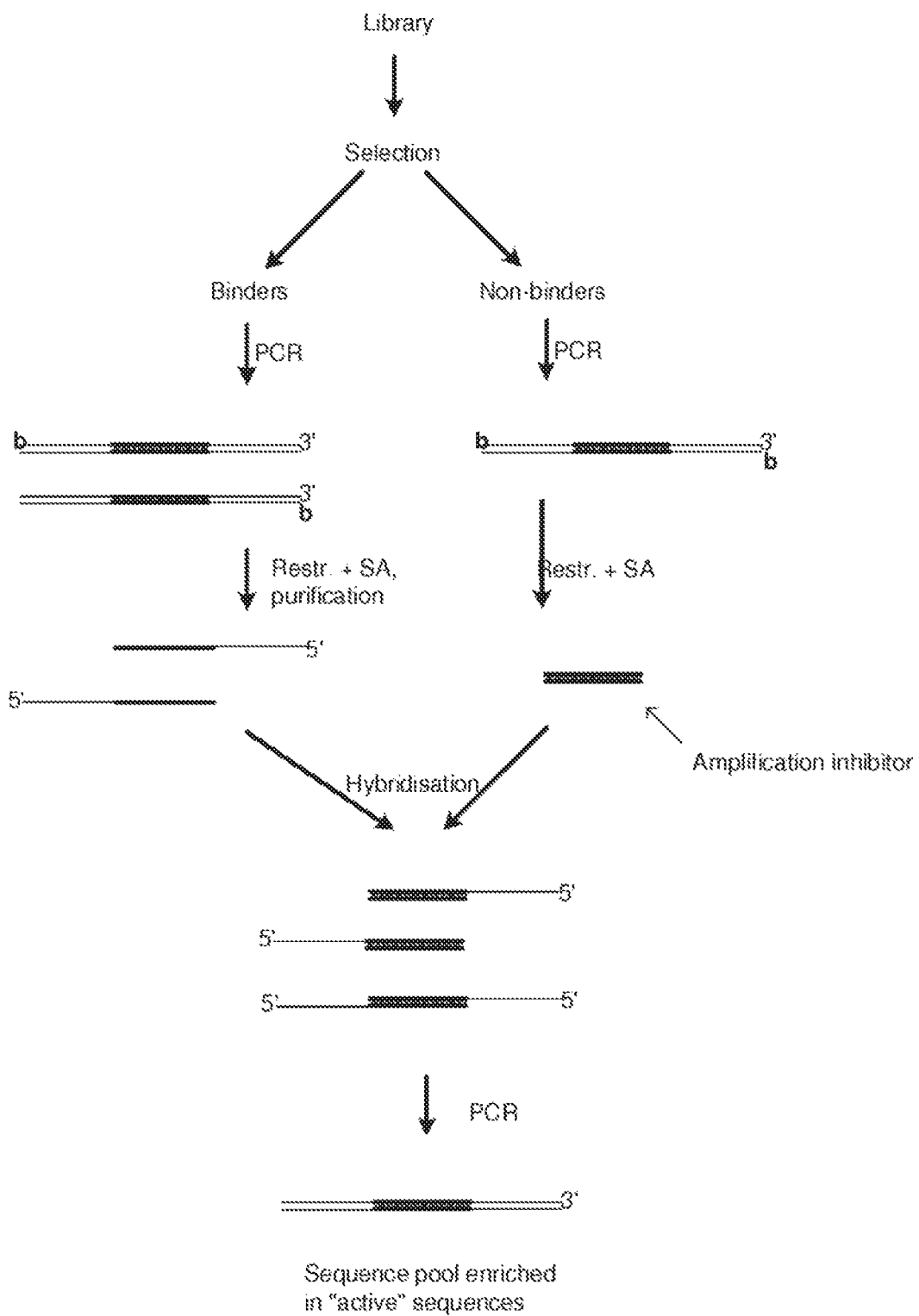
FIG. 22 illustrate the principle of the method for enriching a library of reporter sequences for sequences corresponding to active molecules using specific amplification inhibitors.

A fourth aspect of the invention is a method for enriching a library of reporter sequences for sequences corresponding to active molecules comprising the steps of:
a. Providing a library of oligonucleotides
b. Fractionating said library of oligonucleotides against a molecular target into an binding fraction and a non-binding fraction, wherein the binding fraction contains non-binders
c. Generating a library of reporter sequences corresponding to the oligonucleotide species of the binding fraction
d. Generating a library of reporter sequences corresponding to the oligonucleotide species of the non-binding fraction
e. Modifying the reporter sequences of step d, such that they will inhibit amplification of their complementary counterparts in the library of step c
f. Incubating the library of step c with the library of step e under conditions of hybridization
g. Performing a PCR reaction on the hybridization reaction of step f.
h. Thereby generating a library of reporter sequences corresponding to the oligonucleotide species of the active fraction that has been further enriched in sequences corresponding to specific binders The Principle is Illustrated in FIG. 22

In a preferred embodiment, the reporter sequences of the binding fraction has been manipulated such as to only contain one fixed sequence, wherefore selection of hybridized oligonucleotides is done by a method comprising the steps of:
a. Incubating a plurality of oligonucleotides under conditions of hybridisation
b. Extending the 3' end of one or more hybridised oligonucleotide species, such that the extended region generate a new primer binding site
c. Amplifying extended sequences by PCR using said new primer binding site In another preferred embodiment, the reporter sequences of the non-binding fraction have had both fixed regions removed. Thus, if they hybridise to their complementary counterparts in the library of reporter sequences from the binding fraction, they will actually inhibit amplification of those sequences. In other words, they reporter sequences devoid of fixed regions can specifically inhibit amplification of their complementary counterpart, i.e. they have become specific amplification inhibitors. In yet another embodiment, the reporter sequences of the non-binding fraction that have had both fixed regions removed has been further "inactivated" such that their 3' end cannot be extended by a polymerase. A preferred method of inactivation is by ligation of a dideoxy-nucleotide to the 3' end.

In another preferred embodiment, the reporter sequences of the binding fraction are converted to RNA sequences. This can easily be done if one the fixed sequences harbour a RNA polymerase promoter, e.g. T7 or SP6. The RNA sequences can then be hybridised to their complementary counterparts in the library of reporter sequences from the non-binding fraction, i.e. forming RNA-DNA hybrids. As the skilled man will appreciate, the RNA part of RNA-DNA hybrids can be degraded using RNase H. Thus, again reporter sequences corresponding to non-binders can be removed from a reporter library. Preferably, if the RNA sequences are of one polarity, e.g. coding strand, then the reporter sequences of the binding fraction should have the opposite polarity, i.e. be anticoding. One strand of a double stranded oligonucleotide can easily be purified using a capture group as outlined elsewhere in the specification.

Removing the Most Abundant Sequences of a Library of Reporter Sequences

In yet another embodiment, RNA sequences are used to remove the oligonucleotides of high abundance in a library of oligonucleotides. In this embodiment, a reporter library is spilt into two, where the coding strand of the first subset is purified. The second subset is converted into RNA complementary to the coding strand of the first subset, i.e. the RNA is the anticoding strand. Then the sequences are incubated under conditions of hybridization. As discussed earlier, high abundant sequences will hybridize more quickly than low abundant sequences. Thus, at some point RNase H may be added to degrade the RNA part of RNA-DNA hybrids, i.e. the most abundant oligonucleotides. RNase H may then be inactivated e.g. by heat and one or more non-specific DNases (e.g. a single strand specific DNase and a double strand specific DNase) may be added. The result is a library of (RNA) reporter sequences that has been depleted of the most abundant sequences. This may be of interest to facilitate identification of sequences otherwise buried in the most abundant sequences, a problem also described elsewhere in the specification.

Method of Identifying All Active Library Members by Sequential Selections

Identification of all active library members may be a problem for several reasons. As outlined above, even slight differences in concentration range may be expanded too much for identification. Therefore, the evolution of several parallel reporter libraries may be used.

Thus, another aspect of the invention is a method of identifying all active molecules in a library of oligonucleotides by sequential selections of the library of oligonucleotides against constant or increasing amounts of molecular targets such as to fractionate active compounds according to their affinity for the target.

In a preferred embodiment, the method comprises the steps of:
  a. Fractionating a library of oligonucleotides against a target into to a fraction containing binders and another fraction containing non-binders
  b. Fractionating the fraction containing non-binders of step a) against a target present in the same or in a higher concentration than in step a into to a fraction containing binders and another fraction containing non-binders
  c. Fractionating the fraction containing non-binders of step b) against a target present in the same or in a higher concentration than in step b into to a fraction containing binders and another fraction containing non-binders
  d. Fractionating the fraction containing non-binders of step c) against a target present in the same or in a higher concentration than in step c into to a fraction containing binders and another fraction containing non-binders
    wherein further repetitions may be performed and wherein the fraction containing binders of each step is subsequently analyzed to determine the identity of binders.

Figure 23:
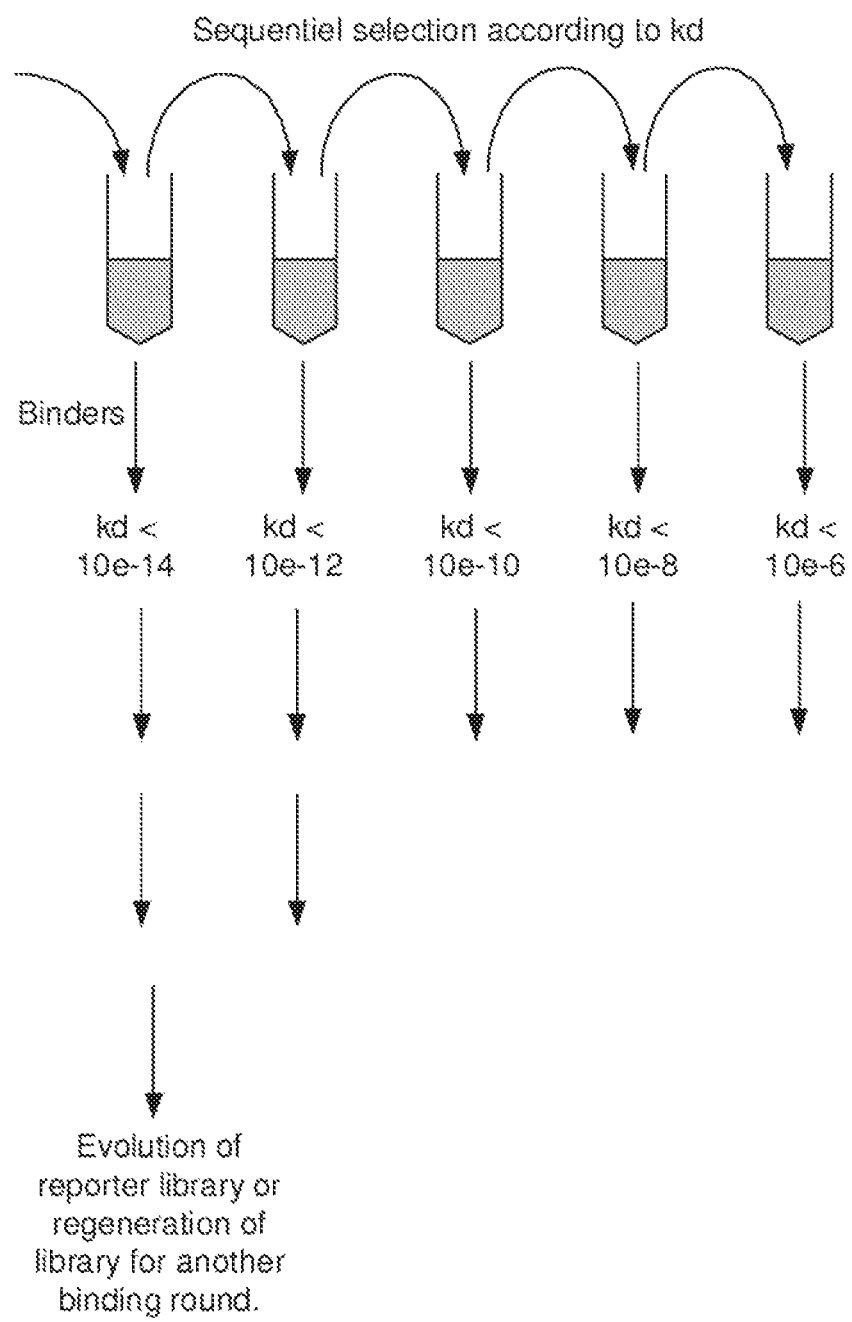
FIG. 23 illustrate the principle of the method of identifying all active library members by sequential selections.

By these separate successive fractionations, library members will be selected according to affinity. The principle is shown in FIG. 23. For each fraction, a reporter library may then be evolved such as to allow identification of the most abundant library members in each fraction. In consequence, all library members having affinity for the target may be identified and additionally, during the process a preliminary ranking according to affinity of the library members will be obtained.

Thus, in one embodiment, the fractions containing binders is subjected to further manipulations before identification of binders.

In a preferred embodiment, further manipulations involve a library of reporter sequences In still another preferred embodiment, the library of reporter sequences is subjected to at least one hybridization reaction.

In a preferred embodiments of the method of identifying all active library members by separate successive selections, the oligonucleotides are selected from the group of aptamers and encoded molecules.

A Method of Avoiding Identification of False Positives

Another aspect of the invention is a method of avoiding identification of false positives from a library of encoded molecules that has been selected against a molecular target, comprising the steps:
  a. Providing a first encoded library
  b. Providing a second encoded library, wherein the encoded molecules are the same as in the first encoded library, wherein the coding sequence of each encoded molecule is the complementary sequence of the coding sequence for the same encoded molecule in the first encoded library.
  c. Performing at least one fractionation of the first encoded library against a molecular target
  d. Performing at least one fractionation of the second encoded library against a molecular target
  e. Incubating the enriched libraries of step c and d or reporter libraries derived thereof under conditions of hybridization
  f. Selecting the oligonucleotide species of step e) that has hybridized.
  g. Thereby generating a library of reporter sequences, wherein the sequences selected in step a) and step b) because of activity in the identifier sequence have been eliminated.

A potential problem when performing fractionation with encoded libraries is that the identifier sequence may contribute to the fractionation. In other words, the identifier sequence may have affinity for the target. One way of minimizing this problem is to use double stranded identifier sequences that cannot from 3 dimensional structures to the same extent as single stranded identifier sequences. Another solution is to use the method outlined above, which is based on the postulation that two complementary oligonucleotides will very seldom have affinity for the same target molecule.

A Codon Specifying the Omission of a Synthesis Step

The identifier sequence of an encoded compound typically comprises a coding region and optionally one or two fixed sequences. The coding region is the region that identifies the encoded compound. Typically, a coding region comprises a number of codons specifying a number of chemical reactions. E.g. each codon may specify addition of an amino acid as outlined by Lerner and Brenner in the original work on encoded libraries. In principle, a codon may specify any chemical reaction, building blocks or even particular conditions, e.g. the temperature at which a reaction is performed.

A codon that is of particular interest is a codon which does not code for anything. E.g. the codon may specify that no amino acid (aa) has been added or that no chemical reaction has taken place. Such a codon may serve as an internal control in a library of encoded compound. Consider e.g. an encoded library of hexameric peptides, where each amino acid is encoded by a codon of 5 nucleotides. Due to inefficient coupling, a particular encoded compound may only comprise 5 amino acids, but have a coding region, which identifies 6 aa. If the 5 aa compound has a high affinity for a target, the result may be a false positive, since the 6 aa does not bind. If a codon that codes for no amino acid is used, the same 5 aa compound will exist in the library, with an identifier sequence that actually identifies the 5 aa compound. Thus, this compound will also be identified and it can be deduced that the 6 aa compound may be a false positive. In addition, to the possibility of serving as an internal control, the use of a codon coding for nothing will obviously also increase library size as all truncations of hexameric peptides are included in the library.

Therefore, another aspect of the invention is a codon specifying the omission of a synthesis step in a sequel of synthesis steps.

And another aspect is a library of encoded compounds comprising a codon specifying the omission of a synthesis step in a sequel of synthesis steps.

The use of a codon specifying the omission of a synthesis step can be used for descriptor-encoded libraries and instructor-encoded libraries. Thus, in one embodiment, the library is a descriptor-encoded library and in another embodiment, the library is an instructor-encoded library. When the library is a instructor encoded library, a anticodon carrying no reactive group may be used.

A Method of Improving the Affinity of a Pre-Determined Binder by Generation of Multivalent Binders Comprising the Steps In another aspect, the invention provides an encoded library, intended improve the affinity of a pre-determined binder. Thus, a predetermined binder is linked to a library of compounds. Optimally, a variety of linkers are used to link the predetermined binder to a library compound, wherefore particular combinations of predetermined compound, library compound and linkers that have high-affinity can be identified. If the predetermined binder alone has a $k_d$ of e.g. $10^{-7}$ M, selection conditions may be adjusted such as to select bivalent compounds with a $k_d$ smaller than $10^{-9}$ M. This can e.g. be done by using a smaller concentration of target molecule or by increasing the binding volume.

Consequently, another aspect is a method of identifying bivalent binders comprising the steps of
 a. Providing a library of encoded molecules wherein the encoded molecules are characterized in comprising an identifier sequence, a pre-determined binder, and a linker of variable length linking the predetermined binder to a variable entity
 b. Fractionating said library against a molecular target
 c. Identifying binders by sequencing the identifier sequence, thereby revealing the combination of linker and variable entity that increases the affinity of the pre-determined binder for the target.

Another aspect of the invention is a method in which a plurality of binders are first identified, where after the identified binders are combined in a new encoded library.

Thus, the method is a method of identifying high-affinity multivalent molecules comprising the steps:
 a. Providing a library of encoded molecules
 b. Fractionating said library against a molecular target
 c. Identifying binders
 d. Providing a library of encoded molecules, wherein the encoded molecules are characterized in comprising an identifier sequence, a linker of variable length and molecular characteristics, linking the a first binder identified in step c with a second binder identified in step c.
 e. Fractionating the library of step d against a molecular target
 f. Identifying binders by sequencing the identifier sequence, thereby revealing the combination of linker and first and second binder that binds with high affinity to the target.

In a preferred embodiment of this method, step c may comprise the generation of a reporter library and one or more hybridization rounds.

Using this methodology, the identification of ultra-high affinity compounds should be possible, as the free energi of binding ($\Delta G$) for each compound can be added, i.e. linking of two $10^{-7}$ M compounds can in theory give a high-affinity binder with a $k_d$ of $10^{-14}$ M. Such high-affinity compounds would be extremely useful in many contexts. They might e.g. be used for as viral entry inhibitors, by completely blocking a viral receptor necessary for entry into the host.

EXAMPLES

The examples are done with a model system using streptavidin as target molecule and a DNA oligonucleotide comprising a biotin group in a DNA oligonucleotide library as model library. Thus, the library comprising the biotin containing oligonucleotide represents a library of oligonucleotides comprising candidate compounds. This library is also termed the primary library in the examples. The corresponding reporter libraries are in the examples also termed secondary libraries. Moreover, oligonucleotides of the primary library are also termed primary molecules and primary oligonucleotides and likewise for oligonucleotides of the secondary library.

Note that the primary library could in principle have been a library of any of the libraries of oligonucleotides described in the specification (encoded libraries, aptamer libraries and subsets thereof).

Example 1

Screening of $10^7$, $10^8$ and $10^9$ libraries.

In this example, model libraries comprising $10^7$, $10^8$ and $10^9$ different DNA oligonucleotide species in equimolar amounts were screened for binding activity against streptavidin immobilized on sepharose. One particular oligonucleotide in the libraries contains a biotin-group at its 5' end and it is intended to demonstrate that the identity of this particular oligonucleotide can be found using the present invention. This particular oligonucleotide is also referred to as the "signal", as it is the oligonucleotide we would like to identify.

The model libraries were prepared by mixing a degenerate oligonucleotide (with a total diversity of $10^7$, $10^8$ or $10^9$) with the biotinylated oligonucleotide, such that the latter was present in equimolar amounts with individual sequences of the degenerate oligonucleotides. Thus, it is intended to demonstrate that the present invention can be used to find a signal within a huge excess of noise.

Strictly speaking, we do not know whether other oligonucleotides than the biotin containing oligonucleotide have affinity toward the target, since it is well known that oligonucleotides can take up tertiary structures that bind protein targets with high-affinity and selectivity. As mentioned in the specification, such oligonucleotides are often termed aptamers.

When evolving a reporter library by iterated hybridisations, a crucial point is that only hybridised oligonucleotides are amplified, and not oligonucleotides that may have been selected because of non-specific interactions with streptavidin beads, plastic tubes etc.

Therefore we implemented a setup in which only hybridised oligonucleotides can be amplified, because each provide a fixed region for PCR-amplification, i.e. non-hybridised oligonucleotides cannot are not amplified because they lack the 3'-fixed region. This principle is also described in the specification.

PCR Primers

All oligonucleotides were synthesised using standard DNA oligonucleotide synthesis such as described in (Oligonucleotide Synthesis: A Practical Approach, M. J Gait) and can consequently be purchased from commercial suppliers such as DNA technology A/S, Forskerparken/Science Park Aarhus, Gustaw Wieds Vej 10A, DK-8000 Aarhus C, Denmark, www.dna-technology.com

```
Primary PCR primer, PCR-11:
5' b GGGAGA CAAGAA TAACCT CAGC

Secondary PCR primer, PCR-12:
5' GCCTGT TGTGAG CCTCCT GTCGAA
```

"b" (5' biotin phosphoramidite catalogue-nr. 10-5950-95 from Glen Research) indicates a biotin group, which will be incorporated in the coding strand of the PCR-product.

The underlined sequence is the complementary of "5'G CT GAGG" which is recognised by the ss DNA restriction enzyme N.BbvC IA (NEB, R0631L, 10 U/μl) and cleaved between the nucleotides in bold. This restriction site is used to cleave off the 3'-fixed region of anticoding oligonucleotides.

Step a) Providing the primary libraries

Three model libraries were prepared using redundant positions during synthesis. The same signal oligonucleotides was used in all three model libraries and the same secondary signal oligonucleotides was used in all three secondary libraries.

$10^7$ Primary Library

The primary libraries were prepared such as to contain about $10^7$, $10^8$ or $10^9$ different sequences (i.e. oligonucleotides). This was accomplished using redundant positions during DNA synthesis. To achieve a library with $10^7$ different sequences, 24 positions with a redundancy of 2 was used ($2^{24}=1.7\times10^7$), Redundancies are described using the ambiguity table from International Union of Biochemistry (http://www.chem.qmuL.ac.uk/iubmb/misc/naseq.html):

M=A or C; R=A or G; W=A or T; S=C or G; Y=C or T; K=G or T; V=A or C or G; H=A or C or T; D=A or G or T; B=G or C or T; N=A or G or C or T.

```
Primary signal oligo, PSO-NheI:
5' b GGGAGA CAAGAA TAACCT CAGC AAAGAC TCGAAG

CGAAAT ATGGGC GCCATG CTAGCG

Primary noise oligo, PNO-10e7:
5' GGGAGA CAAGAA TAACCT CAGC MRKKAA KYMRAA

YRYMAC MYYKGT RYRMTC MYKKCA
```

(actual diversity: $2^{24} = 1.7 \times 10^7$)

"GCTAGC" is the sequence recognised by the ds DNA restriction enzyme NheI (NEB, R0131L, 10 U/μl). This restriction site is used to monitor the evolution of the secondary library.

10e8 Primary Library

```
Primary signal oligo, PSO-NheI:
5' b GGGAGA CAAGAA TAACCT CAGC AAAGAC TCGAAG

CGAAAT ATGGGC GCCATG CTAGCG

Primary noise oilgo, PNO-10e8:
5' GGGAGA CAAGAA TAACCT CAGC MRKKAA KYMRMA

YRYMAT RRYKYT RYRMTC MYKKYA
```

(actual diversity: $2^{27} = 1.3 \times 10^8$)

10e9 Primary Library

```
Primary signal oligo, PSO-NheI:
5' b GGGAGA CAAGAA TAACCT CAGC AAAGAC TCGAAG

CGAAAT ATGGGC GCCATG CTAGCG

Primary noise oligo, PNO-10e9:
5' GGGAGA CAAGAA TAACCT CAGC MRKKMA KYMRMA

YRYMMT RRYKYT RYRMKC MYKKYA
```

(actual diversity $2^{30} = 1.1 \times 10^9$)

Step b) Providing the secondary libraries

10e7 Secondary Library

```
Secondary signal oligo, SSO-NheI:
5' GCCTGT TGTGAG CCTCCT GTCGAA CGCTAG CATGGC

GCCCAT ATTTCG CTTCGA GTCTTT

Secondary noise oligo, SNO-10e7:
5' GCCTGT TGTGAG CCTCCT GTCGAA TGMMRK GAKYRY

ACMRRK GTKRYR TTYKRM TTMMYK
```

10e8 Secondary Library

```
Secondary signal oligo, SSO-NheI:
5' GCCTGT TGTGAG CCTCCT GTCGAA CGCTAG CATGGC

GCCCAT ATTTCG CTTCGA GTCTTT

Secondary noise oligo, SNO-10e8:
5' GCCTGT TGTGAG CCTCCT GTCGAA TRMMRK GAKYRY

ARMRYY ATKRYR TKYKRM TTMMYK
```

10e9 Secondary Library

```
Secondary signal oligo, SSO-NheI:
5' GCCTGT TGTGAG CCTCCT GTCGAA CGCTAG CATGGC

GCCCAT ATTTCG CTTCGA GTCTTT
```

-continued

Secondary noise oligo, SNO-10e9:
5' GCCTGT TGTGAG CCTCCT GTCGAA TRMMRK GMKYRY

ARMRYY AKKRYR TKYKRM TKMMYK

Step c-1) Hybridising oligonucleotide species of the first generation secondary library with oligonucleotide species of the primary library DNA-oligonucleotides were mixed with hybridisation buffer (180 µl 20×SSC+60 µl 0.1% Triton X-100+76.8 µl H$_2$O) according to the scheme below to create both the primary and secondary libraries in a total volume of 100 µl. i.e. the primary library is hybridised to the secondary library before selection against the target.

A) 10e7 library:
52.8 µl hybridisation buffer
20 µl 200 µM PNO-10e7
20 µl 200 µM SNO-10e7
2.4 µl 100 pM PSO-NheI
2.4 µl 100 pM SSO-NheI
2.4 µl 0.01% Triton B) Negative control omitting signal in secondary library, otherwise as A:
52.8 µl hybridisation buffer
20 µl 200 µM PNO-10e7
20 µl 200 µM SNO-10e7
2.4 µl 100 µpM PSO-NheI
4.8 µl 0.01% Triton C) Negative control omitting signal in primary library, otherwise as A:
52.8 µl hybridisation buffer
20 µl 200 µM PNO-10e7
20 µl 200 µM SNO-10e7
2.4 µl 100 pM SSO-NheI
4.8 µl 0.01% Triton D) 10e8 library
52.8 µl hybridisation buffer
20 µl 200 µM PNO-10e8
20 µl 200 µM SNO-10e8
3.1 µl 10 pM PSO-NheI
3.1 µl 10 pM SSO-NheI
1 µl 0.01% Triton E) 10e9 library
52.8 µl hybridisation buffer
20 µl 200 µM PNO-10e9
20 µl 200 µM SNO-10e9
3.6 µl 1 pM PSO-NheI
3.6 µl 1 pM SSO-NheI Next, the libraries (tubes A to E) were heated to 94° C. for 5 minutes followed by incubation at 65° C. overnight (ON) with mixing in a table shaker for hybridisation.

Step d-1) Contacting the target molecule with at least a subset of the primary library hybridised to the secondary library.

120 µl solid phase bound target suspension (app. 30% Streptavidin Sepharose High Performance beads in 20% EtOH, Amersham, 17-5113-01) was centrifuged to pellet the solid phase (sepharose beads). The supernatant was disposed and 600 µl 6×SSC, 0.01% Triton X-100 added. After resuspension of the solid phase, it was again pelleted by centrifugation and the supernatant disposed. The solid phase was resuspended in 114 µl 6×SSC, 0.01% Triton X-100 to give a total volume of app. 150 µl.

25 µl equilibrated solid phase suspension was added to samples A-E and incubated at 65° C. for 20 minutes with mixing.

step e-1) Selecting the oligonucleotide species of the primary library that interact specifically with the target molecule, thereby also selecting oligonucleotide species of the secondary library hybridised to selected primary molecules ("primary molecules" are oligonucleotides species of the primary library, also termed primary species and likewise for oligonucleotides of the secondary library).

After incubation with the solid phase bound target, samples were centrifuged, the supernatant disposed, beads resuspended in 180 µl 10× wash buffer (1 M NaCl, 1.00 mM Tris-HCl pH 8) containing 0.01% Triton X-100 and re-incubated at 65° C. for 20 minutes with mixing. For a second wash, the samples were centrifuged, supernatant disposed and beads resuspended in 180 µl 10× wash buffer. This was followed by a third wash where the samples were centrifuged, supernatant disposed and beads resuspended in 180 µl 1× wash buffer. Next, the beads were pelleted by centrifugation and the supernatant disposed.

Step f-1) Amplifying the hybridised oligonucleotides

Residual biotin binding sides on the solid phase were blocked by addition of 1 µl 20 mM Biotin (Sigma, B-4501) and the total volume of the samples adjusted to 20 µl by addition of 1× wash buffer (app. 8 µl). This was followed by incubation at room-temperature (RT; 25° C.) for 5 minutes with mixing.

Samples A-E was then added 440 µl PCR mix containing:
350 µl H$_2$O
50 µl 10× buffer (Bioline, BIO-21050)
15 µl 50 mM MgCl$_2$ (Bioline, BIO-21050)
20 µl dNTPs, 5 mM each (Bioline, BIO-39025)
5 µl polymerase (BIO-X-ACT long, Bioline, BIO-21050)

As a negative PCR control, sample F, 2 µl 1× wash buffer was added 44 µl PCR mix (as above).

Samples A-F was incubated at 72° C. for 5 minutes, where after 20 µl 10 µM primer PCR-11 and 20 µl 10 µM primer PCR-12 were added to samples A-E and 2 µl of PCR-11 and PCR-12 to sample F. The samples were aliquoted into PCR tubes and amplification was performed using the following (standard PCR) program:

Initial denaturation: 94° C., 5 min.
30 cycles: 94° C., 30 sec
68° C., 60 sec
72° C., 10 sec
Final extension: 72° C., 5 min After amplification, beads were removed by spin-filtration (using Quantum Prep Mini Spin Columns, Bio-Rad, 732-6100).

Step j) Monitoring the evolution of the secondary library

5 µl of samples A-F were added 1 µl NheI+1 µl buffer 2 (NEB, B7002S) +3 µl H$_2$O and incubated at 37° C. for 3 hours. The samples were then added 3 µl 30% glycerol and together with a 25 bp DNA ladder (Promega, G4511) resolved on a 4% GTG (BioWhittaker (BMA), 50084) agarose gel using 1×TBE as running buffer, FIG. 1A.

As negative control for restriction, 5 µl of samples A-F were added 1 µl buffer 2+4 µl H$_2$O and incubated at 37° C. for 3 hours. The samples were then added 3 µl 30% glycerol and together with a 25 bp DNA ladder resolved on an agarose gel, FIG. 1B.

Since no restriction digestion/cleavage was detected after round 1, we moved on to cleavage and purification of the anti-coding DNA strands of the PCR products to generate the second-generation secondary libraries.

Step h): Preparing the second-generation secondary library for the next round

The 3'-fixed region of the anticoding strand of the secondary library was liberated using N. Bbv C IA, where after the truncated anticoding strand containing the 5-fixed region and the anticoding region was gel-purified as described next.

Cleavage of the Anti-Coding Strand with the Nicking Enzyme N, Bbv C IA

Samples A-E were concentrated with EtOH precipitation by adding 3M NaAc pH 4.5 (0.1 times the sample volume) and 95% EtOH (2 times the sample volume), incubation at −80° C. for 20 minutes, centrifugation at 20.000 g for 40 minutes, disposal of the supernatant and air drying of the pellet before dissolving the samples in 100 µl H$_2$O by incubation at RT for 20 minutes with mixing. Next, the samples were desalted by gel-filtration on P30 columns (RNase-Free Micro Bio-Spin, Bio-Rad, 732-6251), whereafter the PCR products were digested by adding 15 µl buffer 2 (NEB, B7002S)+5 µl N.BbvC IA+H$_2$O up till 150 µl, followed by incubation at 37° C. ON. After digestion, the samples were added 1 µl glycogen (20 mg/ml, Roche, 901 393), EtOH precipitated and pellets dissolved in 40 µl H$_2$O.

Purification of Nicked DNA Under Non-Denaturing Conditions

After addition of 20 µl formamide loading buffer (95% formamide, 20 mM EDTA, Bromophenol Blue) to samples A-E, nicked DNA was resolved from non-nicked DNA on a polyacrylamide gel (1×TBE, 8 M urea, 10% polyacrylamide, 0.25% bis-polyacrylamide, length: 15.5 cm, width: 14.5 cm and thickness: 0.1 cm) at low temperature. Appropriate size markers were included (25 pmol of an 80 nt. and an 60 nt. DNA oligonucleotide). After 5 hours at 300 volt, UV-shadowing was used to visualize DNA in the gel. The band (gel-piece) corresponding to nicked DNA was cut out of the gel, soaked in 800 µl 6×SSC, 0.01% Triton X-100 and incubated at room temperature over night in a table shaker for passive elution of the DNA. After elution, acryl amide pieces were removed by spin-filtration.

Binding of Coding Strands to Streptavidin and Elution of Anti-Coding Strands 25 µl equilibrated streptavidin sepharose prepared as described earlier (step d-1) was added to samples A-E, followed by incubation at RT for 45 minutes with mixing. To wash the beads, the samples were centrifuged, supernatant disposed, beads resuspended in 180 µl 1× wash buffer. Next, the samples were transferred to spin-filters and centrifuged 1 minute at 20,000 g. The beads were then resuspended in 40 µl 100 mM NaOH and incubated at RT for 5 minutes. To collect the anti-coding DNA strands, the filters were centrifuged at 20.000 g for 30 sec. 40 µl eluate was neutralized by adding 40 µl 100 mM HCl and 10 µl Tris-HCl pH 8, followed by addition of 1 µl glycogen, EtOH precipitation and dissolution in 5 µl H$_2$O.

Purification of Anti-Coding Strands Under Denaturing Conditions

After addition of 10 µl formamide loading buffer, samples A-E were incubated at 94° C. for 5 minutes, and placed on ice before being loaded onto a polyacrylamide gel (1×TBE, 8M urea, 10% polyacrylamide, 0.25% bis-polyacrylamide, length: 25 cm, width: 24 cm and thickness: 0.1 cm) and run at high temperature (app 55° C.). Appropriate size markers were included. After 4½ hours at 700 volt, the gel was soaked for 10 minutes in 400 ml 1×TBE+200 µl EtBr (2 mg/ml), which allowed visualization of DNA bands with UV-light. The bands corresponding to the anti-coding strands, devoid of the 3′ fixed region were cut out of the gel, soaked in 400 µl 10× wash buffer, 0.01% Triton X-100 and incubated at RT ON with mixing for passive elution of the DNA. After elution, polyacrylamide pieces were removed by spin-filtration. Next, the samples were EtOH precipitated, dissolved in 50 µl 0.01% Triton X-100 and desalted by gel-filtration. Finally, 6 µl of the purified anti-coding strands were analysed on a 4% GTG agarose gel using 1×TBE as running buffer together with 0.5, 1 and 2 pmol of SNO-10e7. From the gel, 6 µl of the purified samples A-E were estimated to contain app 0.75 pmol anti-coding strands, ready to be used as second-generation secondary libraries in the next round of screening.

Step i) Repetitions—Second round

Step c-1) Hybridising oligonucleotide species of the second generation secondary library with oligonucleotide species of the primary library Second-generation secondary libraries, primary libraries and hybridisation buffer (330 µl 20×SSC+110 µl 0.1% Triton X-100+312.4 µl H$_2$O) were aliquoted into tubes A1-E2 according to the scheme below.

A1) 10e7 library:
68.4 µl hybridisation buffer
20 µl 200 µM PNO-10e7
2.4 µl 100 pM PSO-NheI
8 µl sample A from previous round (app. 1 pmol)
1.2 µl 0.1% Triton X-100

A2) 10e7 library, 10× diluted secondary library:
68.4 µl hybridisation buffer
20 µl 200 µM PNO-10e7
2.4 µl 100 pM PSO-NheI
8 µl sample A from previous round 10× diluted in 0.01% Triton (app. 0.1 pmol)
1.2 µl 0.1% Triton X-100

B1) Negative control omitting signal in secondary library, otherwise as A1:
68.4 µl hybridisation buffer
20 µl 200 µM PNO-10e7
2.4 µl 100 pM PSO-NheI
8 µl sample B from previous round
1.2 µl 0.1% Triton X-100

B2) Negative control omitting signal in secondary library, otherwise as A2:
68.4 µl hybridisation buffer
20 µl 200 µM PNO-10e7
2.4 µl 100 pM PSO-NheI
8 µl sample B from previous round 10× diluted in 0.01% Triton
1.2 µl 0.1% Triton X-100

C1) Negative control omitting signal in primary library, otherwise as A1:
68.4 µl hybridisation buffer
20 µl 200 µM PNO-10e7
8 µl sample C from previous round
3.6 µl 0.1% Triton X-100

C2) Negative control omitting signal in primary library, otherwise as A2:
68.4 µl hybridisation buffer
20 µl 200 µM PNO-10e7
8 µl sample C from previous round 10× diluted in 0.01% Triton
3.6 µl 0.1% Triton X-100

D1) 10e8 library:
68.4 µl hybridisation buffer
20 µl 200 µM PNO-10e8

3.1 µl 10 pM PSO-NheI
8 µl sample D from previous round
0.5 µl 0.1% Triton X-100
D2) 10e8 library, 10× diluted secondary library:
68.4 µl hybridisation buffer
20 µl 200 µM PNO-10e8
3.1 µl 10 pM PSO-NheI
8 µl sample D from previous round 10× diluted in 0.01% Triton
0.5 µl 0.1% Triton X-100
E1) 10e9 library:
68.4 µl hybridisation buffer
20 µl 200 µM PNO-10e9
3.6 µl 1 pM PSO-NheI
8 µl sample E from previous round
E2) 10e9 library, 10× diluted:
68.4 µl hybridisation buffer
20 µl 200 µM PNO-10e9
3.6 µl 1 pM PSO-NheI
8 µl sample E from previous round 10× diluted in 0.01% Triton As in round 1, the libraries (samples A1 to E2) were heated to 94° C. for 5 minutes followed by incubation at 65° C. ON with mixing in a table shaker for hybridisation.

Step d-1) Contacting the target molecule with at least a subset of the primary library hybridised to the secondary library 240 µl solid phase bound target suspension was centrifuged to pellet the solid phase (sepharose beads). The supernatant was disposed and 1200 µl 6×SSC, 0.01% Triton X-100 added. After resuspension of the solid phase, it was again pelleted by centrifugation and the supernatant disposed. The equilibrated solid phase bound target was then resuspended in 228 µl 6×SSC, 0.01% Triton X-100 to give a total volume of app. 300 µl.

25 µl equilibrated solid phase suspension was added to samples A1-E2 from and incubated at 65° C. for 20 minutes with mixing.

Step e-1) Selecting the primary oligonucleotides of the primary library that interact specifically with the target molecule, thereby also secondary oligonucleotides hybridised to selected primary oligonucleotides.

After incubation with the solid phase, samples were centrifuged, the supernatant disposed, beads resuspended in 180 µl 10× wash buffer (1 M NaCl, 100 mM Tris-HCl pH 8) containing 0.01% Triton X-100 and at 65° C. for 20 minutes with mixing. For second wash, the samples were centrifuged, supernatant disposed: and beads resuspended in 180 µl 10× wash buffer. This was followed by a third wash where the samples were centrifuged, supernatant disposed and beads resuspended in 180 µl 1× wash buffer. Next, the beads were pelleted by centrifugation and supernatant disposed.

Step f-1) Amplifying the hybridised oligonucleotides

Residual biotin binding sides on the solid phase were blocked by addition of 1 µl 20 mM Biotin (Sigma, B-4501) and the total volume of the samples adjusted to 20 µl by addition of 1× wash buffer (app. 8 µl). This was followed by incubation at room-temperature (RT; 25° C.) for 5 minutes with mixing.

PCR Amplification

2 µl of samples A1-E2 were added 44 µl PCR mix containing:
35 µl $H_2O$
5 µl 10× buffer
1.5 µl 50 mM $MgCl_2$
2 µl dNTPs, 5 mM each
0.5 µl polymerase As a negative PCR control, sample F, 2 µl 1× wash buffer was added 44 µl PCR mix (as above).

Samples A-F was incubated at 72° C. for 5 minutes, where after 2 µl 10 µM primer PCR-11 and 2 µl 10 µM primer PCR-12 were added to samples A-F.

A positive restriction control, PCR marker, was prepared: 1 µl 10 nM PSO-NheI +1 µl 10 nM SSO-NheI was added 44 µl PCR mix (as above)+2 µl 10 µM primer PCR-11 and 2 µl 10 µM primer PCR-12 in a PCR tube.

Amplification of samples A1-F and PCR marker was performed using the same program (standard PCR) as in the previous round, step f-1.

After amplification, beads were removed by spin-filtration (using Quantum Prep Mini Spin Columns, Bio-Rad, 732-6100).

Step j) Monitoring the evolution of the secondary library

Figure 2:
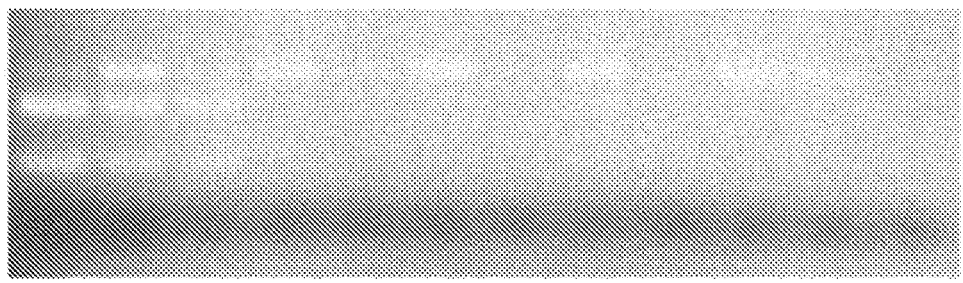
Figure 2:
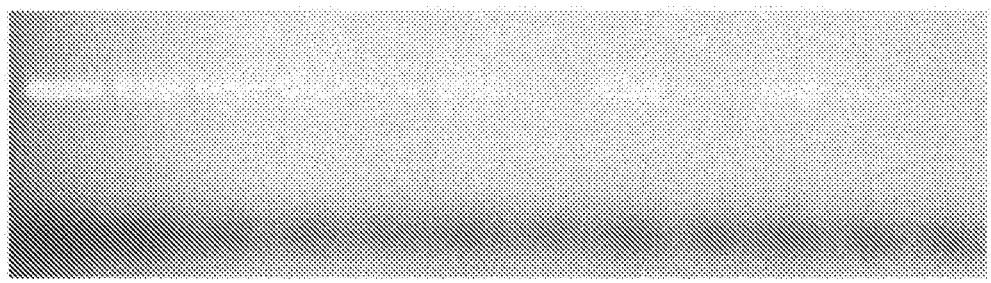

5 µl PCR marker and samples A1-F were added 1 µl NheI+1 µl buffer 2+3 µl $H_2O$ and incubated at 37° C. for 2 hours. The samples were then added 3 µl 30% glycerol and together with a 25 bp DNA ladder resolved on a 4% GTG (BioWhittaker (BMA), 50084) agarose gel using 1×TBE as running buffer, FIG. 2A.

As negative control for restriction, 5 µl PCR marker and samples A1-F were added 1 µl buffer 2+4 µl $H_2O$ and incubated at 37° C. for 2 hours. The samples were then added 3 µl 30% glycerol and together with a 25 bp DNA ladder resolved on an agarose gel, FIG. 2B.

Samples A1, B1, C1, D1 and E1 resulted in a clearly visible PCR product whereas samples A2, B2, C2, D2 and E2 resulted in a lesser visible or non-visible PCR product, in accordance with the lower concentrations of second-generation secondary library used. The restriction analysis indicates that after round 2, A1 has evolved as to contain about 50% (½) signal oligonucleotide from the original $1/1.7 \times 10^7$. D1 has evolved to contain about 5% (1/20) signal oligonucleotide from the original $1/1.3 \times 10^8$, which corresponds respectively to enrichments of approximately $8.5 \times 10^6$ and $6.5 \times 10^6$ after two rounds.

Step h) Preparing the second-generation secondary library for the next round

The process was continued with a third round, wherefore large scale PCR amplifications of selected (non-amplified) oligonucleotides from step f-1) was done, before purifying truncated anti-coding strands Large Scale PCR Amplification Samples A1, B1, C1, D1 and E1 (18 µl) were each added 442 µl PCR mix containing:
352 µl $H_2O$
50 µl 10× buffer
15 µl 50 mM $MgCl_2$
20 µl dNTPs, 5 mM each
5 µl polymerase The samples were incubated at 72° C. for 5 minutes. Hereafter, 20 µl 10 µM primer PCR-11 and 20 µl 10 µM primer PCR-12 were added and the samples were aliquoted into PCR tubes.

Amplification was performed using the standard PCR program, as in round 1, step f-1.

After amplification, beads were removed by spin-filtration.

Cleavage of the Anti-Coding Strand with the Nicking Enzyme N. Bbv C IA

Sample A1-E1 were concentrated, desalted and digested as in step h, round 1, followed by EtOH precipitation and dissolution in 20 µl H$_2$O.

Purification of Nicked DNA Under Non-Denaturing Conditions

After addition of 10 µl formamide loading buffer to samples A1-E1, nicked DNA was purified as in step h, round 1.

Binding of Coding Strands to Streptavidin and Elution of Anti-Coding Strand

As in step h, round 1.

Purification of Anti-Coding Strands Under Denaturing Conditions

As in step h, round 1.

10 µl of the purified A1-E1 samples (total vol. 50 µl) were analysed on a 4% GTG agarose gel, using 1×TBE as running buffer, together with 0, 1 and 2 pmol of SNO-10e7. From the gel, 10 µl of A1 was estimated to contain app 0.2 pmol truncated anticoding strands whereas 10 µl of B1, C1, D1 or E1 contained app 2 pmol truncated anti-coding strands ready to be used as third-generation secondary libraries in the next round of screening.

Step i) Repetitions—third round

Step c-1) Hybridising oligonucleotide species of the third generation secondary library with oligonucleotide species of the primary library Third-generation secondary A1-E1 libraries, primary libraries and hybridisation buffer (330 µl 20×SSC+110 µl 0.1% Triton X-100+345.4 µl H$_2$O) were aliquoted into tubes A1-E2 according to the scheme below.

A1) 10e7 library, 100× diluted secondary library:
71.4 µl hybridisation buffer
20 µl 200 µM PNO-10e7
2.4 µl 100 pM PSO-NheI
5 µl sample A1 from previous round 100× diluted in 0.01% Triton (app 1 fmol)
1.2 µl 0.1% Triton X-100

A2) 10e7, 1000× diluted secondary library:
71.4 µl hybridisation buffer
20 µl 200 µM PNO-10e7
2.4 µl 100 pM PSO-NheI
5 µl sample A1 from previous round 1.000× diluted in 0.01% Triton (app 0.1 fmol)
1.2 µl 0.1% Triton X-100

B1) Negative control omitting signal in secondary library, otherwise as A1:
71.4 µl hybridisation buffer
20 µl 200 µM PNO-10e7
2.4 µl 100 pM PSO-NheI
5 µl sample B1 from previous round 1.000× diluted in 0.01% Triton
1.2 µl 0.1% Triton X-100

B2) Negative control omitting signal in secondary library, otherwise as A2:
71.4 µl hybridisation buffer
20 µl 200 µM PNO-10e7
2.4 µl 100 pM PSO-NheI
5 µl sample B1 from previous round 10.000× diluted in 0.01% Triton
1.2 µl 0.1% Triton X-100

C1) Negative control omitting signal in primary library, otherwise as A1:
71.4 µl hybridisation buffer
20 µl 200 µM PNO-10e7
5 µl sample C1 from previous round 1.000× diluted in 0.01% Triton
3.6 µl 0.1% Triton X-100

C2) Negative control omitting signal in primary library, otherwise as A2:
71.4 µl hybridisation buffer
20 µl 200 µM PNO-10e7
5 µl sample C1 from previous round 10.000× diluted in 0.01% Triton
3.6 µl 0.1% Triton X-100

D1) 10e8, 1000× diluted secondary library:
71.4 µl hybridisation buffer
20 µl 200 µM PNO-10e8
3.1 µl 10 pM PSO-NheI
5 µl sample D1 from previous round 1.000× diluted in 0.01% Triton
0.5 µl 0.1% Triton X-100

D2) 10e8 10000× diluted secondary library:
71.4 µl hybridisation buffer
20 µl 200 µM PNO-10e8
3.1 µl 10 pM PSO-NheI
5 µl sample D1 from previous round 10.000× diluted in 0.01% Triton
0.5 µl 0.1% Triton X-100

E1) 10e9, 1000× diluted secondary library:
71.4 µl hybridisation buffer
20 µl 200 µM PNO-10e9
3.6 µl 1 pM PSO-NheI
5 µl sample E1 from previous round 1.000× diluted in 0.01% Triton E2) 10e9, 10000× diluted secondary library:
71.4 µl hybridisation buffer
20 µl 200 µM PNO-10e9
3.6 µl 1 pM PSO-NheI
5 µl sample E1 from previous round 10.000× diluted in 0.01% Triton As in round 1 and 2, the libraries (samples A1 to E2) were heated to 94° C. for 5 minutes followed by incubation at 65° C. ON with mixing in a table shaker for hybridisation.

Step d-1) Contacting the target molecule with at least a subset of the primary library hybridised to the secondary library As in the previous round, step d-1

Step e-1) Selecting the primary oligonucleotides of the primary library that interact specifically with the target molecule, thereby also secondary oligonucleotides hybridised to selected primary oligonucleotides.

As in the previous round, step e-1

Step f-1) Amplifying the hybridised oligonucleotides

As in the previous round, step f-1

Step j) Monitoring the evolution of the secondary library

Figure 3:
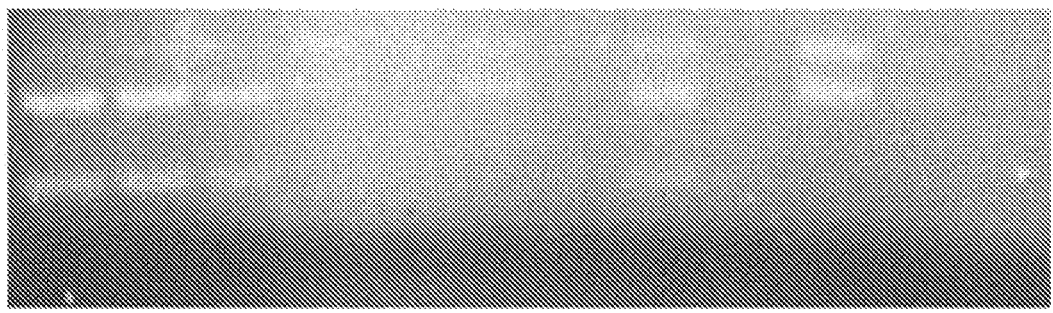
Figure 3:
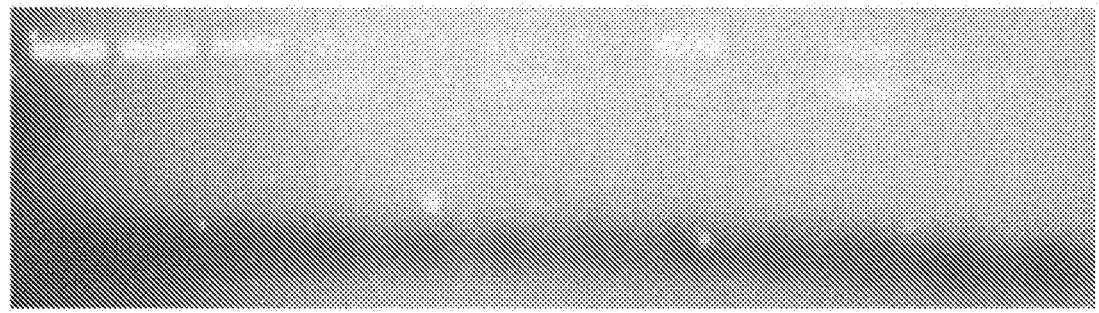

5 µl PCR marker and samples A1-F were added 1 µl NheI+1 µl buffer 2+3 µl H$_2$O and incubated at 37° C. for 3 hours. The samples were then added 3 µl 30% glycerol and together with a 25 bp DNA ladder resolved on an 4% GTG agarose gel, FIG. 3A.

As negative control for restriction, 5 µl of PCR marker and sample A1-F were added 1 µl buffer 2+4 µl H$_2$O and incubated at 37° C. for 3 hours. The samples were then added 3 µl 30% glycerol and together with a 25 bp DNA ladder resolved on an agarose gel, FIG. 3B.

Samples A1 and A2 had evolved to contain app. 90% signal (approximately 1,5×10$^7$ fold enrichment) and D1 to contain about 50% signal (approximately 6,5×10$^7$ fold enrichment). E1 or E2 had not yet evolved to a detectable level where digestion was visible. The experiment might have been continued with another round to see whether samples E (10e9 library) would eventually give a signal (visible digestion), but instead a new experiment was initiated.

Example 2

Various questions may be asked to infer the generality of the use of a reporter library by hybridisation to detect e.g. the presence of a ligand such as an encoded molecule or an aptamer in a library of such molecules. First, is the system dependent on the very strong interaction displayed by the model system (biotin-streptavidin interaction) used? According to example 1, it does not appear so, as only mild washing conditions were used. However, in the present example also a weaker interaction is tested.

Another question, is whether evolution of a reporter library is dependent on perfect or nearly perfect hybridisation for information transfer from the primary to the secondary library? These questions will be sought answered in the present example 2.

In example 2, three different libraries were used and two variants of solid phase bound target was used; SoftLink™ Soft Release Avidin Resin (in short: SoftLink) and Tetralink™ Tetrameric Avidin Resin (in short: TetraLink). Tetralink has a very strong interaction with biotin with a dissociation constant ($k_d$) of app 10$^{-14}$ M, whereas Softlink base relatively weak interaction reflected in a high dissociation constant of 10$^{-7}$ M. Comparing the results of using the two targets should indicate whether the method is dependent on the extremely strong interaction typical for biotin and avidin/streptavidin. Moreover, the results may be compared to those in example 1 where streptavidin immobilized on sepharose is used as target.

Two answer whether perfect hybridisation is a requirement for the method, we designed a library where sequences have a maximum of sequence identity. Thus, in the information transfer (hybridisation), the signal (and obviously also the noise oligonucleotides) may basepair to its perfect match (36/36 basepairs) or to secondary oligonucleotides containing 35 out of 36 correct positions, 34 out of 36 etc. At the given hybridisation conditions, we anticipate that many faulty hybridisations will be occurring, although with a bias against perfect hybridisation.

PCR Primers

```
Primary PCR primer, PCR-11:
5' b GGGAGA CAAGAA TAACCT CAGC

Secondary PCR primer, PCR-12:
5' GCCTGT TGTGAG CCTCCT GTCGAA
```

"b" indicates a biotin group, which will be incorporated in the coding strand of the PCR-product.

The underlined sequence is the complementary of "5' G CT GAGG" which is recognised by the ss DNA restriction enzyme N.BbvC IA (NEB, R0631L, 10 U/µl) and cleaved between the nucleotides in bold. This restriction site is used to cleave of the 3'-fixed region of anticoding Oligonucleotides.

```
Primary PCR product extending primer, Ext1-PCR11:
cacgac gttgta aaacga ca GGGAG ACAAG AATAA CCTCA Secondary PCR product extending primer,
Ext2-PCR12:
ggataa caattt cacaca ga GCCT GTTGT GAGCC TCCTG T
```

Primary sequencing primer, Ext1:
cacgac gttgta aaacga ca
Secondary sequencing primer, Ext2:
ggataa caattt cacaca ga
Step a) Providing the primary libraries
As in example 1, redundant positions during DNA-oligonucleotide synthesis are used to build the libraries.

10e6 Library, SoftLink and TetraLink, BamHI Marker

```
Primary signal ago, PSO-BamHI:
5' b GGGAGA CAAGAA TAACCT CAGC AGAGAT TTGAAC

CAAAAG ACGGGG ATCCTG CTATCT

Primary noise oligo, PNO-10e6:
5' GGGAGA CAAGAA TAACCT CAGC MRDTAA KYVGAG

YRHCAC YMBTGT RYVCTC MYDGCA (actual diversity: 2^12 x 3^6 = 3 x 10^6)
```

"GG ATCC" is the sequence recognised by the ds DNA restriction enzyme BamHI (NEB, R0136L, 20 U/µl) which cleaves between the two nucleotides marked in bold type.

10e7 Library, TetraLink, Max. Identity, PacI Marker

```
Primary signal oligo, PSO-PacI:
5' b GGGAGA CAAGAA TAACCT CAGC CGTTAA TTAAAA

CGCCAC CCTTGT ATGCTC ATGGCA

Primary noise oligo, PNO-10e7:
5' GGGAGA CAAGAA TAACCT CAGC MRKKAA KYMRAA

YRYMAC MYYKGT RYRMTC MYKKCA (actual diversity: 2^24 = 1.7 x 10^7)
```

TTAATTAA" is the sequence recognised by the ds DNA restriction enzyme PacI (NEB, R0547L, 10 U/µl) which cleaves between the two nucleotides marked in bold type. This restriction site is used to monitor the evolution of the secondary library.

10e8 Library, TetraLink, BamHI Marker

```
Primary signal oligo, PSO-BamHI:
5' b GGGAGA CAAGAA TAACCT CAGC AGAGAT TTGAAC

CAAAAG ACGGGG ATCCTG CTATCT

Primary noise oligo, PNO-10e8:
5' GGGAGA CAAGAA TAACCT CAGC MRKKAA KYMRMA

YRYMAT RRYKYT RYRMTC MYKKYA (actual diversity: 2^27 = 1.3 x 10^8)
```

Step b) Providing the secondary libraries

10e6 Library, SoftLink and TetraLink, BamHI Marker

```
Secondary signal oligo, SSO-BamHI:
5' GCCTGT TGTGAG CCTCCT GTCGAA AGATAG CAGGAT

CCCCGT CTTTTG GTTCAA ATCTCT

Secondary noise oligo, SNO-10e6:
5' GCCTGT TGTGAG CCTCGT GTCGAA TGCHRK GAGBRY

ACAVKR GTGDYR CTCBRM TTAHYK
```

10e7 Library, TetraLink, Max. Identity, PacI Marker

```
Secondary signal oligo, SSO-PacI:
5' GCCTGT TGTGAG CCTCCT GTCGAA TGCCAT GAGCAT

ACAAGG GTGGCG TTTTAA TTAACG

Secondary noise oligo, SNO-10e7:
5' GCCTGT TGTGAG CCTCCT GTCGAA TGMMRK GAKYRY

ACMRRK GTKRYR TTYKRM TTMM
```

10e8 Library, TetraLink, BamHI Marker

```
Secondary signal oligo, SSO-BamHI:
5' GCCTGT TGTGAG CCTCCT GTCGAA AGATAG CAGGAT

CCCCGT CTTTTG GTTCAA ATCTCT

Secondary noise oligo, SNO-10e8:
5' GCCTGT TGTGAG CCTCCT GTCGAA TRMMRK GAKYRY

ARMRYY ATKRYR TKYKRM TTMMYK
```

Step c-1) Hybridising secondary oligonucleotides of the first generation secondary library with primary oligonucleotides of the primary library DNA-oligonucleotides and hybridisation buffer (300 µl 20×SSC+100 µl 0.1% Triton X-100+138 µl H$_2$O) were aliquoted into tubes A-H according to the scheme below.

A) 10e6, SoftLink
53.8 µl hybridisation buffer
20 µl 200 µM PNO-10e6
20 µl 200 µM SNO-10e6
2.6 µl 0.5 nM PSO-BamHI
2.6 µl 0.5 nM SSO-BamHI
1 µl 0.01% Triton B) Negative control omitting signal in secondary library, otherwise as A:
53.8 µl hybridisation buffer
20 µl 200 µM PNO-10e6
20 µl 200 µM SNO-10e6
2.6 µl 0.5 nM PSO-BamHI
3.6 µl 0.01% Triton C) 10e6, TetraLink:
53.8 µl hybridisation buffer
20 µl 200 µM PNO-10e6
20 µl 200 µM SNO-10e6
2.6 µl 0.5 nM PSO-BamHI
2.6 µl 0.5 nM SSO-BamHI
1 µl 0.01% Triton D) Negative control omitting signal in secondary library, otherwise as C:
53.8 µl hybridisation buffer
20 µl 200 µM PNO-10e6
20 µl 200 µM SNO-10e6
2.6 µl 0.5 nM PSO-BamHI
3.6 µl 0.01% Triton E) 10e7, max identity
53.8 µl hybridisation buffer
20 µl 200 µM PNO-10e7
20 µl 200 µM SNO-10e7
2.4 µl 100 pM PSO-PacI
3.8 µl 0.01% Triton F) Negative control omitting signal in primary library, otherwise as E:
53.8 µl hybridisation buffer
20 µl 200 µM PNO-10e7
20 µl 200 µM SNO-10e7
6.2 µl 0.01% Triton G) 10e8, TetraLink:
53.8 µl hybridisation buffer
20 µl 200 µM PNO-10e8
20 µl 200 µM SNO-10e8
3.1 µl 10 pM PSO-BamHI
3.1 µl 10 pM SSO-BamHI H) Negative control omitting signal in secondary library, otherwise as G:
53.8 µl hybridisation buffer
20 µl 200 µM PNO-10e8
20 µl 200 µM SNO-10e8
3.1 µl 10 pM PSO BamHI
3.1 µl 0.01% Triton Next, the libraries (tubes A to H) were heated to 94° C. for 5 minutes followed by incubation at 65° C. overnight (ON) with mixing in a table shaker for hybridisation.

Step d-1) Contacting the target molecule with at least a subset of the primary library hybridised to the secondary library.

60 µl solid phase bound target (app. 50% SoftLink Soft Release Avidin Resin in 20% EtOH, Promega, V2011) was centrifuged to pellet the solid phase. The supernatant was disposed and 600 µl 6×SSC, 0.01% Triton X-100 added. After resuspension of the solid phase, it was again pelleted by centrifugation and the supernatant disposed. The solid phase was resuspended in 45 µl 6×SSC, 0.01% Triton X-100 to give a total volume of app. 75 µl.

140 µl solid phase bound target (app. 50% TetraLink Tetrameric Avidin Resin in 20% EtOH, Promega, V2591) was centrifuged to pellet the solid phase. The supernatant was disposed and 1400 µl 6×SSC, 0.01% Triton X-100 added. After resuspension of the solid phase, it was again pelleted by centrifugation and the supernatant disposed. The solid phase was resuspended in 105 µl 6×SSC, 0.01% Triton X-100 to give a total volume of app. 175 µl.

25 µl equilibrated solid phase was added to the samples (SoftLink to A and B, and TetraLink to samples C-H) followed by incubation at 65° C. for 60 minutes with mixing.

step e-1) Selecting the primary oligonucleotides of the primary library that interact specifically with the target molecule, thereby also selecting secondary oligonucleotides hybridised to selected primary oligonucleotides After incubation with the solid phase bound target, samples were centrifuged, supernatant disposed, beads resuspended in 180 µl 10× wash buffer (1 M NaCl, 100 mM Tris-HCl pH 8) containing 0.01% Triton X-100 and re-incubated at 65° C. for 45 minutes with mixing. For the second wash, samples were centrifuged, supernatant disposed and beads resuspended in 180 μl 10× wash buffer. This was followed by a third wash where the samples were centrifuged, supernatant disposed and beads resuspended in 180 μl 1× wash buffer. Next, the beads were pelleted by centrifugation and the supernatant disposed.

Step f-1) Amplifying the hybridised oligonucleotides

Residual biotin binding sides on the solid phase were blocked by addition of 1 μl 20 mM Biotin (Sigma, B-4501) and the total volume of the samples adjusted to 20 μl by addition of 1× wash buffer (app. 8 μl). This was followed by incubation at room-temperature (RT; 25° C.) for 5 minutes with mixing.

Samples A-H was added 440 μl PCR mix containing:
350 μl $H_2O$
50 μl 10× buffer (Bioline, BIO-21050)
15 μl 50 mM $MgCl_2$ (Bioline, BIO-21050)
20 μl dNTPs, 5 mM each (Bioline, B-39025)
5 μl polymerase (BIO-X-ACT long, Bioline, BIO-21050)

As a negative PCR control, sample I, 2 μl 1× wash buffer was added 44 μl PCR mix (as above).

Samples A-I were incubated at 72° C. for 5 minutes. Hereafter, 20 μl 10 μM primer PCR11 and 20 μl to 10 μM primer PCR12 were added to samples A-H and 2 μl of each primer to sample I. The samples were aliquoted into PCR tubes and amplification was performed using the following (standard PCR) program:

Initial denaturation 94° C., 5 min
30 cycles: 94° C., 30 sec
68° C., 60 sec
72° C., 10 sec
Final extension: 72° C., 5 min After amplification, the beads were removed by spin-filtration (Microporous 0.22 micron ultrafree-MC centrifugal filter units, Millipore, UFC3 0GV MB).

Step j) Monitoring the evolution of the secondary library

Figure 4:
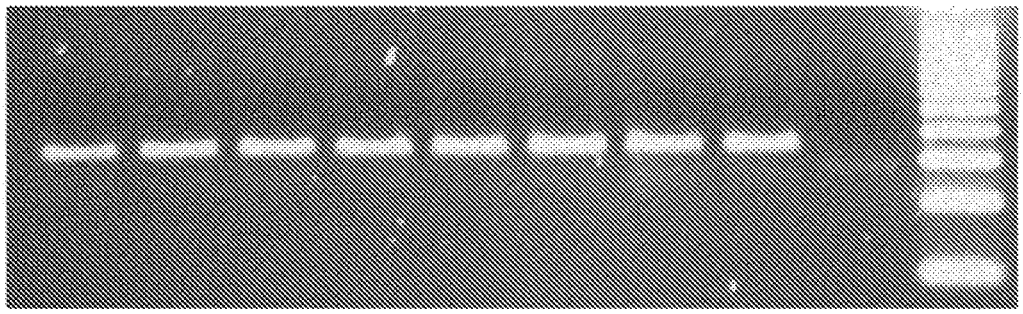
Figure 4:
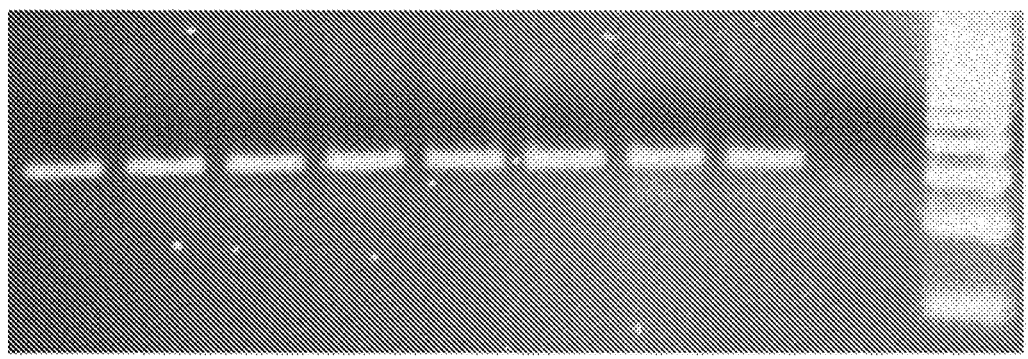

5 μl of samples A-D, G-I and PCR marker 1 were each added 1 μl BamHI +1 μl buffer H (Roche, 1417991)+3 μl $H_2O$. 5 μl of samples E and F were each added 1 μl PacI+1 μl buffer 1 (New England Biolabs)+3 μl $H_2O$ The samples were then added 3 μl 30% glycerol and together with a 25 bp DNA ladder (Promega, G4511) resolved on a 4% GTG (BioWhittaker (BMA), 50084) agarose gel using 1×TBE as running buffer, FIG. 4A.

As negative restriction controls, 5 μl of sample A-I were added 1 μl buffer H+4 μl $H_2O$ and incubated at 37° C. for 1 hour. The samples were then added 3 μl 30% glycerol and together with a 25 bp DNA ladder resolved on an GTG agarose gel, FIG. 4B No restriction was detected after round 1. Hence we moved on to cleavage and purification of the anti-coding DNA strands of the PCR products to generate the second-generation secondary libraries for the next round of screening.

Step h) Preparing the second-generation secondary library for the next round

The 3' fixed region of the anticoding strand of the secondary library was cleaved off using N. Bbv C IA, where after the truncated anticoding strand containing the 5-fixed region and the anticoding region was gel-purified.

Samples A-H were concentrated with an EtOH precipitation by adding 3M NaAc pH 4.5 (0.1 times the sample volume) and 95% EtOH (2 times the sample volume), incubation at −80° C. for 20 minutes, centrifugation at 20.000 g for 40 minutes, disposal of the supernatant, air drying of the pellet before dissolution in 100 μl $H_2O$ by incubation at RT for 20 minutes with mixing. Next, the samples were desalted by gel-filtration on G25 columns (MicroSpin G-25 Columns, Amersham, 27-5325-01), where after the PCR products were digested by adding 15 μl buffer 2 (NEB, B7002S)+5 μl N.BbvC IA+$H_2O$ up till 150 μl, followed by incubation at 37° C. ON. After digestion, the samples were added 1 μl glycogen (20 mg/ml, Roche, 901 393), EtOH precipitated and pellets dissolved in 15 μl $H_2O$.

Purification of Nicked DNA Under Non-Denaturing Conditions

After addition of 7.5 μl formamide loading buffer (95% formamide, 20 mM EDTA, Bromophenol Blue) to samples A-H, nicked DNA was resolved from non-nicked DNA on a polyacrylamide gel (1×TBE, 6 M urea, 10% polyacrylamide, 0.25% bis-polyacrylamide, length: 15.5 cm, width: 14.5 cm and thickness: 0.1 cm) by running the gel at low temperature. Appropriate size markers were included. After 4.5 hours at 300 volt, the gel was soaked for 10 minutes in 400 ml 1×TBE+200 μl EtBr (2 mg/ml), which allowed visualization of DNA bands with UV-light. The band (gel-piece) corresponding to nicked DNA was cut out of the gel, soaked in 400 μl 6×SSC, 0.01% Triton X-100 and incubated at room temperature over night with mixing for passive elution of the DNA. After elution, acryl amide pieces were removed by spin-filtration.

Binding of Coding Strands to Streptavidin and Elution of Anti-Coding Strand

180 μl solid phase suspension (app. 30% Streptavidin Sepharose High Performance beads in 20% EtOH, Amersham, 17-5113-01) was centrifuged to pellet the solid phase. The supernatant was disposed and 900 μl 6×SSC, 0.01% Triton X-100 added. After resuspension of the solid phase, it was again pelleted by centrifugation and the supernatant disposed. The solid phase was resuspended in 171 μl 6×SSC, 0.01% Triton X-100 to give a total volume of app. 225 μl.

25 μl equilibrated solid phase suspension was added to samples A-H, followed by incubation at RT for 30 minutes with mixing. To wash the beads, the samples were centrifuged, supernatant disposed, beads resuspended in 180 μl 1× wash buffer. Next, the samples were transferred to spin-filters and centrifuged for 30 seconds at 1000 g. The beads were then resuspended in 40 μl 100 mM NaOH and incubated at RT for 5 minutes. To collect the anti-coding DNA strands, the filters were centrifuged at 20.000 g for 30 seconds. 40 μl eluate was neutralized by adding 40 μl 100 mM HCl and immediately followed by addition of 1 μl glycogen, EtOH precipitation and redissolution in 7.5 μl $H_2O$.

Purification of Anti-Coding Strands Under Denaturing Conditions

After addition of 15 μl formamide loading buffer, samples A-H were incubated at 94° C. for 6 minutes with mixing, and placed on ice before loading on a polyacrylamide gel (1×TBE, 8M urea, 10% polyacrylamide, 0.25% bis-polyacrylamide, length: 25 cm, width: 24 cm and thickness: 0.1 cm) and run at high temperature (app 55° C.). Appropriate size markers were included. After 4½ hours at 700 volt, the gel was soaked for 10 minutes in 400 ml 1×TBE+200 μl EtBr (2 mg/ml), which allowed visualization of DNA bands with UV-light. The bands corresponding to the anti-coding strands, devoid of the 3' fixed region were cut out of the gel, soaked in 400 µl 10× wash buffer, 0.01% Triton X-100 and incubated at RT ON with mixing for passive elution of the DNA. After elution, polyacrylamide pieces were removed by spin-filtration. Next, the samples were EtOH precipitated, dissolved in 50 µl 0.01% Triton X-100 and desalted by gel-filtration. Finally, 10 µl of the purified anti-coding A-E strands together with 0.5, 1 and 2 pmol of SNO-10e7 were analysed on a 4% GTG agarose gel using 1×TBE as running buffer.

10 µl of the purified samples A, B and D-H were estimated to contain app 0.8 pmol and C app 0.4 pmol anti-coding strands, ready to be used as second-generation secondary libraries in the next round of screening.

Step i) Repetitions—Second round

Step c-1) Hybridising secondary oligonucleotides of the second generation secondary library with primary oligonucleotides of the primary library Second-generation secondary A-H libraries, primary libraries and hybridisation buffer (300 µl 20×SSC+100 µl 0.1% Triton X-100+119 µl H$_2$O) were aliquoted into tubes A-H according to the scheme below.

A) 10e6, SoftLink:
51.9 µl hybridisation buffer
20 µl 200 µM PNO-10e6
25 µl sample A from previous round (app. 2 pmol)
2.6 µl 0.5 nM PSO-BamHI
0.5 µl 0.01% Triton B) Negative control omitting signal in secondary library, otherwise as A:
51.9 µl hybridisation buffer
20 µl 200 µM PNO-10e6
25 µl sample B from previous round (app. 2 pmol)
2.6 µl 0.5 nM PSO-BamHI
0.5 µl 0.01% Triton C) 10e6, TetraLink:
51.9 µl hybridisation buffer
20 µl 200 µM PNO-10e6
25 µl sample C from previous round (app. 1 pmol)
2.6 µl 0.5 nM PSO-BamHI
0.5 µl 0.01% Triton D) Negative control omitting signal in secondary library, otherwise as C:
51.9 µl hybridisation buffer
20 µl 200 µM PNO-10e6
12.5 µl sample D from previous round (app. 1 pmol)
12.5 µl H$_2$O
2.6 µl 0.5 nM PSO-BamHI
0.5 µl 0.01% Triton E) 10e7, max identity:
51.9 µl hybridisation buffer
20 µl 200 µM PNO-10e7
12.5 µl sample E from previous round (app. 1 pmol)
12.5 µl H$_2$O
2.4 µl 100 pM PSO-PacI
0.7 µl 0.01% Triton F) Negative control omitting signal in primary library, otherwise as E:
51.9 µl hybridisation buffer
20 µl 200 µM PNO-10e7
12.5 µl sample F from previous round (app. 1 pmol)
12.5 µl H$_2$O
3.1 µl 0.01% Triton G) 10e8, TetraLink:
51.9 µl hybridisation buffer
20 µl 200 µM PNO-10e8
12.5 µl sample G from previous round (app. 1 pmol)
12.5 µl H$_2$O
3.1 µl 10 pM PSO-BamHI H) Negative control omitting signal in secondary library, otherwise as G:
51.9 µl hybridisation buffer
20 µl 200 µM PNO-10e8
12.5 µl sample H from previous (app. 1 pmol)
12.5 µl H$_2$O
3.1 µl 10 pM PSO-BamHI As in round 1, the libraries (tubes A to H) were heated to 94° C. for 5 minutes followed by incubation at 65° C. ON with mixing in a table shaker for hybridisation.

Step d-1) Contacting the target molecule with at least a subset of the primary library hybridised to the secondary library The solid phase bound targets were equilibrated as described in the previous round to give a total of 75 µl SoftLink and 175 µl TetraLink.

25 µl equilibrated solid phase was added to the samples (SoftLink to A and B, and TetraLink to samples C-H) followed by incubation at 65° C. for 30 minutes with mixing.

step e-1) Selecting the primary oligonucleotides of the primary library that interact specifically with the target molecule, thereby also selecting secondary oligonucleotides hybridised to selected primary oligonucleotides.

Selection was done as described in the previous round, step e-1

Step f-1) Amplifying the oligonucleotides

Residual biotin binding sides on the solid phase were blocked by addition of 1 µl 20 mM Biotin (Sigma, B-4501) and the total volume of the samples adjusted to 20 µl by addition of 1× wash buffer (app. 8 µl). This was followed by incubation at room-temperature (RT; 25° C.) for 5 minutes with mixing.

Samples A-H and as a negative control, I, was PCR amplified as in the previous round (step f-1) in 500 µl and 50 µl reactions, respectively.

After amplification, the beads were removed by spin-filtration (Microporous 0.22 micron ultrafree-MC centrifugal filter units, Millipore, UFC3 0GV NB).

As positive restriction controls, 2 µl 10 nM PSO-BamHI+2 µl 10 nM SSO-BamHI, termed PCR marker 1 and 2 µl 10 nM PSO-PacI+2 µl 10 nM SSO-PacI, termed PCR marker 2 were each added to a PCR mix containing:
70 µl H$_2$O
10 µl 10× buffer
3 µl 50 mM MgCl$_2$
4 µl dNTPs, 5 mM each
4 µl 10 µM primer PCR11
4 µl 10 µM primer PCR12
1 µl polymerase And subsequently amplified as samples A-I.

Step j) Monitoring the evolution of the secondary library

5 µl of samples A-D, G-I and PCR marker 1 were each added 1 µl BamHI +1 µl buffer H+3 µl H$_2$O. 5 µl of samples E, F and PCR marker 2 were each added 1 µl PacI+1 µl buffer I+3 µl H$_2$O. The samples were incubated at 37° C. for 1 hour, then added 3 µl 30% glycerol and analysed on an 4% GTG agarose, FIG. 5A. Samples were loaded in the following order: samples A-I, PCR marker 1, PCR marker 2 and a 25 bp DNA ladder.

Figure 5:
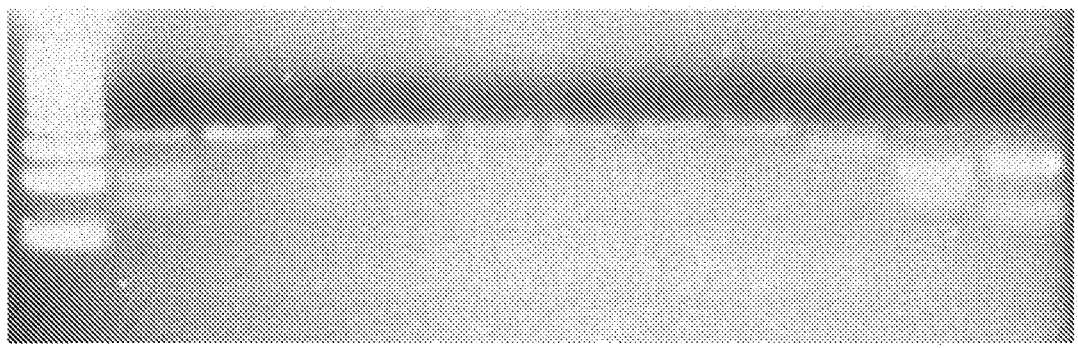
Figure 5:
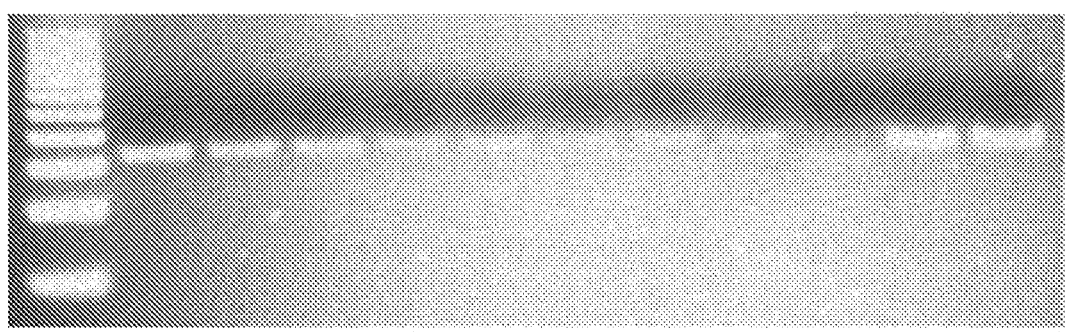

As in the previous round, negative restriction controls was also prepared, FIG. 5B.

The restriction analysis indicates that after round 2, A and C have evolved as to contain about 50% signal from the original 1/3×10e6, which corresponds to an enrichment of approximately 1,5×10⁶.

Step h) Preparing the third-generation secondary library for the next round

To increase the amount of PCR-product before purification of anticoding strands, a second PCR was performed using the samples from the previous step f-1 as templates.

10 µl of 10,000 fold diluted samples A-H were added 490 µl PCR mix that contained:

360 µl H$_2$O
50 µl 10× buffer
15 µl 50 mM MgCl$_2$
20 µl dNTPs, 5 mM each
20 µl 10 µM primer PCR11
20 µl 10 µM primer PCR12
5 µl polymerase (Bio-XACT)

And subsequently amplified as in step f-1.

After amplification, anticoding strands without the 3'-fixed region of the resulting PCR product was purified as described in the previous round.

After elution of the anticoding strand from the denaturing gel, samples were ethanol precipitated and finally dissolved in 25 µl 0.01% Triton X-100 and desalted by gel-filtration. Here after 10 µl of the purified A-H samples together with 0.5, 1 and 2 pmol of SNO-10e7 were analysed on an agarose gel.

10 µl of samples A-G were estimated to contain app 1.5 pmol anticoding strands, whereas 10 µl of sample H contained app 0.5 pmol anti-coding strands, ready to be used as third-generation secondary libraries in the next round of screening.

Step i) Repetitions—Third round

Step c-1) Hybridising secondary oligonucleotides of the third generation secondary library with primary oligonucleotides of the primary library Third-generation secondary libraries (samples A-H), primary libraries and hybridisation buffer (300 µl 20×SSC+100 µl 0.1% Triton X-100+119 µl H$_2$O) were aliquoted into tubes A-H according to the scheme below.

A) 10e6, SoftLink:
51.9 µl hybridisation buffer
20 µl 200 µM PNO-10e6
25 µl sample A from the previous round diluted to app 0.16 nM (app. 4 fmol)
2.6 µl 0.5 nM PSO-BamHI
0.5 µl 0.01% Triton B) Negative control omitting signal in secondary library, otherwise as A:
51.9 µl hybridisation buffer
20 µl 200 µM PNO-10e6
25 µl sample B from the previous round diluted to app 0.16 nM (app. 4 fmol)
2.6 µl 0.5 nM PSO-BamHI
0.5 µl 0.01% Triton C) 10e6, TetraLink:
51.9 µl hybridisation buffer
20 µl 200 µM PNO-10e6
25 µl sample C from the previous round diluted to app 0.16 nM (app. 4 fmol)
2.6 µl 0.5 nM PSO-BamHI
0.5 µl 0.01% Triton D) Negative control omitting signal in secondary library, otherwise as C:
51.9 µl hybridisation buffer
20 µl 200 µM PNO-10e6
25 µl sample D from the previous round diluted to app 0.16 nM (app. 4 fmol)
2.6 µl 0.5 nM PSO-BamHI
0.5 µl 0.01% Triton E) 10e7, max identity:
51.9 µl hybridisation buffer
20 µl 200 µM PNO-10e7
25 µl sample E from the previous round diluted to app 0.04 nM (app. 1 fmol)
2.4 µl 100 pM PSO-PacI
0.7 µl 0.01% Triton F) Negative control omitting signal in primary library, otherwise as E:
51.9 µl hybridisation buffer
20 µl 200 µM PNO-10e7
25 µl sample F from the previous round diluted to app 0.04 nM (app. 1 fmol)
3.1 µl 0.01% Triton G) 10e8, TetraLink:
51.9 µl hybridisation buffer
20 µl 200 µM PNO-10e8
25 µl sample G from the previous round diluted to app 0.04 nM (app. 1 fmol)
3.1 µl 10 pM PSO-BamHI H) Negative control omitting signal in secondary library, otherwise as G:
51.9 µl hybridisation buffer
20 µl 200 µM PNO-10e8
25 µl sample H from the previous round diluted to app 0.04 nM (app. 1 fmol)
3.1 µl 10 pM PSO-BamHI As in round 1 and 2, the libraries (tubes A to H) were heated to 94° C. for 5 minutes followed by incubation at 65° C. ON with mixing for hybridisation.

Step d-1) Contacting the target molecule with at least a subset of the primary library hybridised to the secondary library The solid phase bound targets were equilibrated as described in the previous rounds to give a total of 75 µl SoftLink and 175 µl TetraLink.

2.5 µl equilibrated solid phase was added to the samples (SoftLink to A and B, and TetraLink to samples C-H) followed by incubation at 65° C. for 30 minutes with mixing.

step e-1) Selecting the primary oligonucleotides of the primary library that interact specifically with the target molecule, thereby also selecting secondary-oligonucleotides, hybridised to selected primary oligonucleotides.

Selection was done as described in the previous rounds with three washing steps

Step f-1) Selecting the primary oligonucleotides of the primary library that interact specifically with the target molecule, thereby also selecting secondary oligonucleotides hybridised to selected primary oligonucleotides.

As described in the previous rounds, residual binding sites on the solid phase was blocked, where after 20 µl of samples A-H and a negative control, I (2 µl 1× wash buffer), was amplified in 500 µl and 50 µl reactions, respectively.

Because samples A-H all resulted in relatively little PCR product, a second PCR was performed as described in step h) of the previous round, where after the samples were gelfiltrated with buffer exchange into 0.01% triton X-100.

Step j) Monitoring evolution of the secondary libraries by restriction analysis

5 µl samples A-D, G-I and PCR marker 1 were each added 1 µl BamHI+1 µl buffer H+3 µl H$_2$O; 5 µl samples E, F and PCR marker 2 were each added 1 µl PacI+1 µl buffer 1+3 µl H₂O. The samples were incubated at 3° C. for 1 hour, then added 3 µl 30% glycerol and resolved on an 4% GTG agarose gel, FIG. 6A. Samples were loaded in the following order: samples A-I, PCR marker 1, PCR marker 2 and a 25 bp DNA ladder.

Figure 6:
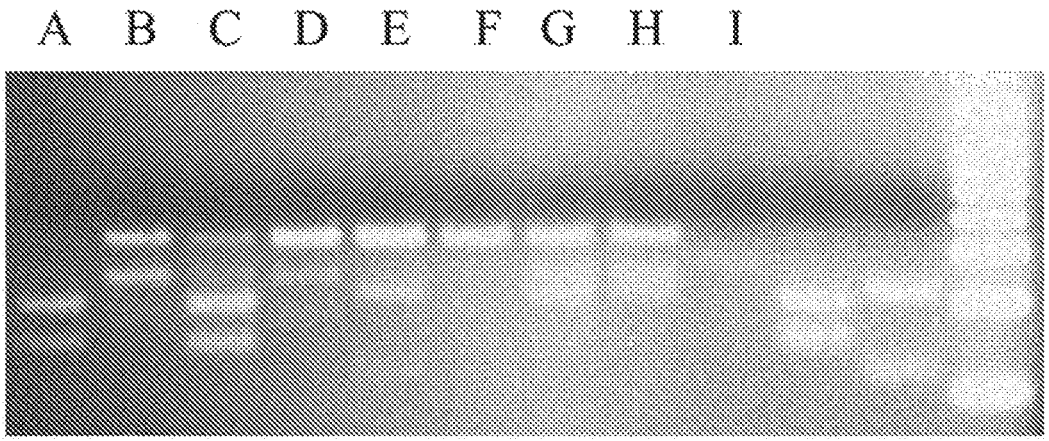
Figure 6:
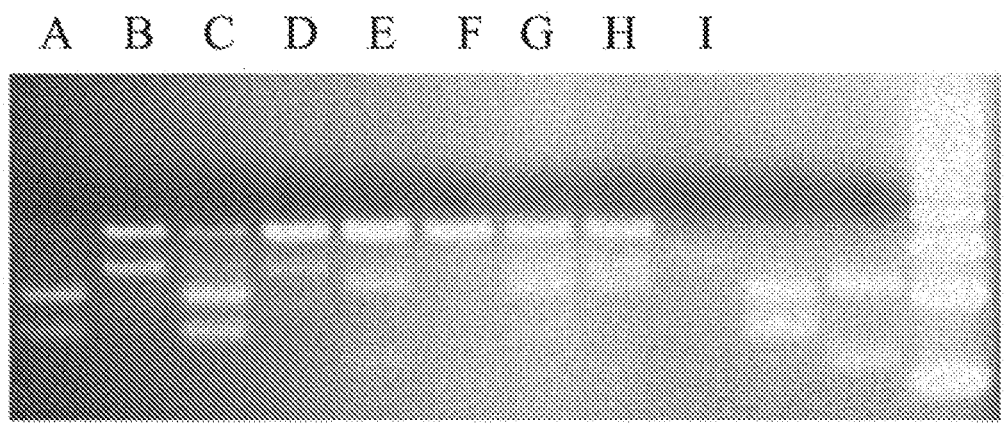

A negative restriction control was also prepared as in the previous rounds, FIG. 6B.

PCR-products of smaller size had appeared in some samples, but nonetheless it could be verified that A and C had evolved to contain approximately 90% signal and E and G to contain about 20% and 5%, respectively. The corresponding enrichment factors are approximately $2,7\times10^6$ (A and C), $3,4\times10^6$ (E) and $6,5\times10^6$ (G).

A fourth round was performed with samples E-H.

Step h) Preparing the second-generation secondary library for the next round

The anticoding strands of samples E-H without the 3'-fixed region was purified as described in the previous rounds. After elution of the anticoding strand from the denaturing gel, samples were ethanol precipitated and finally dissolved in 25 µl 0.01% Triton X-100 and desalted by gel-filtration. Here after 10 µl of the purified E-H samples together with 0.5, 1 and 2 pmol of SNO-10e7 were analysed on a 4% GTG agarose gel.

10 µl of E-H were estimated to respectively contain app 2, 1, 0.5 and 0.25 pmol anti-coding strands ready to be used as fourth-generation secondary libraries in the next round of screening.

Step i) Repetitions—Fourth round

Step c-1) Hybridising secondary oligonucleotides of the fourth-generation secondary library with primary oligonucleotides or the primary library Fourth-generation secondary DNA-oligonucleotides (samples E-H), primary DNA-oligonucleotides and hybridisation buffer (300 µl 20×SS+100 µl 0.1% Triton X-100+ 119 µl H₂O) were aliquoted into tubes E-H according to the scheme below.

E) 10e7, max identity:
51.9 µl hybridisation buffer
20 µl 200 µM PNO-10e7
25 µl sample E from previous round diluted to app 0.05 nM (app. 1.25 fmol)
2.4 µl 100 pM PSO-PacI
0.7 µl 0.01% Triton F) Negative control omitting signal in primary library, otherwise as E:
51.9 µl hybridisation buffer
20 µl 200 µM PNO-10e7
25 µl sample F from previous round diluted to app 0.05 nM (app. 1.25 fmol)
3.1 µl 0.01% Triton G) 10e8, TetraLink:
51.9 µl hybridisation buffer
20 µl 200 µM PNO-10e7
25 µl sample G from previous round diluted to app 0.06 nM (app. 1.5 fmol)
3.1 µl 10 pM PSO-BamHI H) Negative control omitting signal in secondary library, otherwise as G:
51.9 µl hybridisation buffer
20 µl 200 µM PNO-10e8
25 µl sample H from previous round diluted to app 0.06 nM (app. 1.5 fmol)
3.1 µl 10 pM PSO-BamHI As in round 1, 2 and 3, the libraries (tubes E to H) were heated to 94° C. for 5 minutes followed by incubation at 65° C. ON with mixing for hybridisation.

Step d-1) Contacting the target molecule with at least a subset of the primary library hybridised to the secondary library 175 µl TetraLink was equilibrated as described in the previous rounds and 25 µl was added to samples E-H followed by incubation at 65° C. for 30 minutes with mixing.

step e-1) Selecting the primary oligonucleotides of the primary library that interact specifically with the target molecule, thereby also selecting secondary oligonucleotides hybridised to selected primary oligonucleotides Selection was done as described in the previous rounds with three washing steps Step f-1) Amplifying the oligonucleotides As described in the previous rounds; residual binding sites on the solid phase was blocked, where after 20 µl samples E-H and as a negative control, I (2 µl 1× wash buffer), was amplified in 500 µl and 50 µl reactions, respectively.

Step J. Monitoring evolution of the libraries by restriction analysis

5 µl of samples G, H and I were each added 1 µl BamHI+1 µl buffer H+3 µl H₂O; 5 µl samples E and F were each added 1 µl PacI+1 µl buffer 1+3 µl H₂O. The samples were incubated at 37° C. for 1 hour, then added 3 µl 30% glycerol and resolved on a 4% GTG agarose gel, FIG. 7A. Samples were loaded in the following order: samples E-I and a 25 bp DNA ladder.

Figure 7:
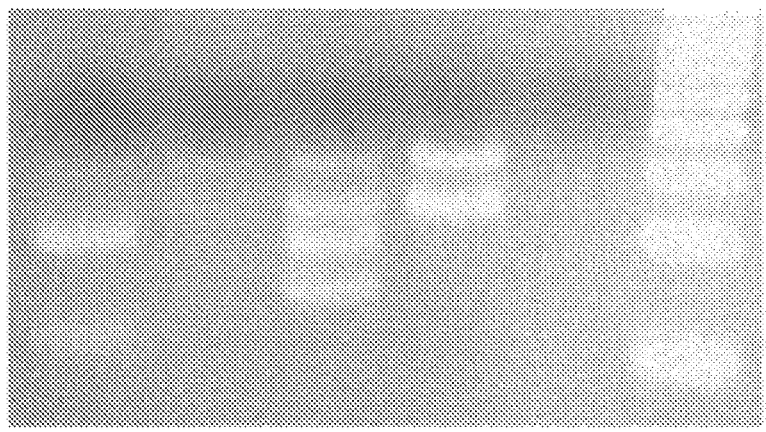
Figure 7:
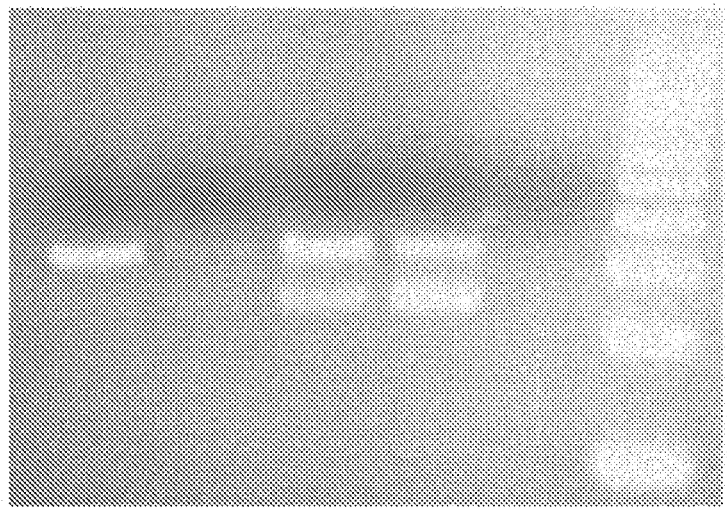

As in the previous rounds, a negative restriction control was also prepared, FIG. 7B.

PCR by-products had again appeared. Nonetheless it can be seen that E and G had evolved to contain app. 90% and 80% signal, corresponding to enrichment factors of $1,5\times10^7$ and $10^8$.

DNA-Sequencing of Secondary Libraries

Evolution of the $10^7$ and $10^8$ libraries were further analysed by DNA-sequencing of the libraries To generate templates for sequencing, 48 µl PCR mix (560 µl H₂O+80 µl 10× Buf+32 µl 5 mM dNTPs+24 µl 50 mM MgCl₂+32 µl 10 µM primer Ext1-PCR11+32 µl 10 µM primer Ext2-PCR12+8 µl XACT) was added to each of the following samples:

1: Fourth round sample F, i.e. negative control without signal in primary $10^7$ library:
2 µl 100× diluted PCR-product F from round 4
2: Reference sequence of the noise oligos in the 10e7 library
1 µl 1 µM PNO-10e7+1 µl 1 µM SNO-10e7
3: Sequence after 1' round selection of 10e7 library
2 µl 10,000× diluted PCR E from round 1
4: Sequence after 2' round selection of 10e7 library
2 µl 10,000× diluted PCR E from round 2
5: Sequence after 3' round selection of 10e7 library
2 µl 100× diluted PCR E from round 3
6: Sequence after 4' round selection of 10e7 library
2 µl 100× diluted PCR E from round 4
7: Reference sequence of the signal oligo in the 10e7 library
1 µl 10 nM SSO-PacI+1 µl 10 nM PSO-PacI
8: Fourth round sample H, i.e. negative control without signal in primary $10^8$ library:
2 µl 100× diluted PCR H from round 4
9: Reference sequence of the noise oligos in the 10e8 library
1 µl 1 µM PNO-10e8+1 µl 1 µM SNO-10e8
10: Sequence after 1' round selection of 10e8 library
2 µl 10,000× diluted PCR G from round 1

11: Sequence after 2' round selection of 10e8 library
2 µl 10,000× diluted PCR G from round 2
12: Sequence after 3' round selection of 10e8 library
2 µl 100× diluted PCR G from round 3
13: Sequence after 4' round selection of 10e8 library
2 µl 100× diluted PCR G from round 4
14: Reference sequence of the signal oligo in the 10e8 library
1 µl 10 nM SSO-BamHI+1 µl 10 nM PSO-BamHI Amplification was performed using the standard PCR program (see step f-1, round 1), except that the hybridisation temperature was 52° C. instead of 68° C.

15 µl of each of the above PCR samples, 1-14, was added to 4 µl 30% glycerol and together with the 25 bp DNA ladder resolved on a 4% GTG agarose gel using 1×TBE as running buffer. The PCR products (122 bp long) were cut out of the gel and purified with QIAEX II (QIAGEN, 20051) according to the manufacture's protocol.

A 5'-labelled sequencing primer was prepared by incubating 7.5 µl 2 µM primer Ext2+7.5 µl γ $^{32}$P-ATP (10 mCi/ml, 5000 Ci/mmol; Amersham)+19 µl H$_2$O+4 µl T4 polynucleotide kinase buffer+2 µl T4 polynucleotide kinase (NEB, M0201L) at 37° C. for 30 minutes, followed by heat-inactivation of the enzyme by incubation at 70° C. for 10 minutes and finally purification of the primer by gel-filtration on G25 columns.

For each of PCR-samples 1-14, a sequencing pre-mix was prepared that contained: 3 µl purified PCR-sample (app 0.1 pmol)+3 µl G25 purified 5'-labelled primer (app 1 pmol)+20.5 µl H$_2$O+3 µl cycling mix (500 mM Tris pH 8.9, 100 mM KCl, 25 mM MgCl$_2$, 0.25% Tween 20)+0.5 µl Taq polymerase. From each pre-mix, 6 µl was added to four PCR tubes containing 2 µl G, A, T or C termination-mix (G: 10 µM each of dGTP, dATP, dTTP and dCTP+80 µM ddGTP; A: 10 µM each of dGTP, dATP, dTTP and dCTP+600 µM ddATP; T: 10 µM each of dGTP, dATP, dTTP and dCTP+900 µM ddTTP; C: 10 µM each of dGTP, dATP, dTTP and dCTP+300 µM ddCTP).

The resulting 14×4 sequence samples were thermocycled in a PCR-machine using the following program:
Initial denaturation: 94° C., 2 min
25 cycles: 94° C., 30 sec
52° C., 30 sec
72° C., 30 sec
Final extension: 72° C., 2 min After thermocycling, 6 µl formamide loading buffer was added to each tube, where after the samples (sequencing reactions) where resolved on denaturing PAGE:

2 µl of the sequence reactions were loaded on a polyacrylamide (1×TBE, 7M urea, 8% polyacrylamide, 0.3% bis-polyacrylamide) gel and run at high temperature. After 1.5 hours with 50 watt, the gel was transferred to Whatman paper and dried. The $^{32}$P labelled DNA was visualized with a phosphor imager scanner and the result is shown in FIGS. 8A (samples 1-7) and 8B (samples 8-14). As clearly seen and in agreement with the restriction analyses performed, the signal oligonucleotide is not visible until after the third round of selection and after the fourth round the library primarily contains the signal oligonucleotide.

Conclusion

Example 2 demonstrates that the method is not dependent on strong interactions, but can also be used for identification of relatively week interactions, as the interaction between biotin and SoftLink ($k_d$ 10$^{-7}$ M). This is not entirely unexpected, as the strong interaction ($k_d$ 10$^{-14}$ M) used in the other experiments is not used exploited in extensive washing procedures to give a high enrichment (strong selection). Thus, three relatively mild washes were employed, where one could have used a larger volume of wash buffer, more harsh buffer such as e.g. 100 mM NaOH and a larger number of washing steps. In conclusion, identification of both high and low-affinity compounds from libraries of encoded compounds and aptamer libraries should be possible using the method.

Moreover, example 2 demonstrated that even when significant faulty hybridisation occurs, the method still works. This is a significant result, because it indicates that a plethora of tag-designs and hybridisation conditions may be used. The sequence content of tags may not necessarily be optimised to reduce faulty hybridisation (tag need not be orthogonal), the tag-length is relatively flexible, as should also hybridisation conditions be. Thus the method might be used advantageously for e.g. libraries not originally intended to be screened by Dosevo such as those prepared by e.g mRNA display, DNA-templated synthesis.'

Finally, note that sequences had not been amplified before PCR. This is important if kinetics of hybridisation may in some way be limiting for the upper library size that can be screened using the method. Thus, if the same experiment had been performed with amplifiable oligonucleotides before hybridisation and selection, the libraries could in theory have been significantly larger. In other words, if PCR had been used to increase the copunumber of each individual library member e.g. 10$^5$ fold, the library could have been 10$^5$ larger.

Example 3

Screening of a 10$^8$ library with only one selection round against the target.

In this experiment, two primary libraries were independently selected against the target, where after selected oligonucleotides were PCR-amplified. Amplified oligonucleotides of one primary library were then hybridised to amplified oligonucleotides of the other primary library. Hybridised oligonucleotides were then amplified to create the first generation secondary library.

For the next round, a new primary selection might have been performed using either one of the primary libraries. However, in the present example only one "real" selection round of the primary library is done, where after the resulting reporter library is cross-hybridised several times, i.e. the anticoding strands of secondary library 1 are hybridised to coding strands of secondary library 2 and coding strands of secondary library 1 are hybridised to anticoding strands of secondary library 2 (or vice versa). This creates two new (and next generation) secondary libraries in which the fixed regions have been exchanged. Exchange of fixed sequences is done to facilitate amplification of only hybridised oligonucleotides. The process can now be repeated by hybridising coding strands of the first secondary library to anticoding strands of the second secondary library and anticoding strands of the first secondary library to coding strands of the second secondary library (or vice versa). The effect is signal amplification by cross-hybridisation. If desired, secondary libraries can at any time be hybridised to a primary library, which may be desirable to keep a selection pressure corresponding to good binders in the primary library.

In principal, only one secondary library could have been employed (instead of two parallel secondary libraries), but in that case strands that had not been freed of their 3'-fixed region would interfere with information transfer, because they would be amplified regardless of whether they had hybridised.

PCR-Primers

Four different fixed (two sets) regions for PCR-amplification was used. After each cross-hybridisation, the fixed regions was swapped to create two new sets of fixed regions. This was done to ensure efficient information transfer, as mentioned above.

Set 1:

```
Primary PCR primer 1, PCR-BamHI-1
5' GGGATA TAGCAA TCCTAC GG

Primary PCR primer biotin 1, PCR-BamHI-1-bt:
5' b GGGATA TAGCAA TCCTAC GG

Secondary PCR primer 1, PCR-EcoRI-1:
5' GGAGTA GCAAAG TAGCGT GA

Secondary PCR primer biotin 1, PCR-EcoRI-1-bt:
5' b GGAGTA GCAAAG TAGCGT GA
```

Set 2:

```
Primary PCR primer 2, PCR-BamHI-2:
5' GGCGTT TCTAAC AACGAA GG

Primary PCR primer biotin 2, PCR-BamHI-2-bt:
5' b GGCGTT TCTAAC AACGAA GG

Secondary PCR primer 2, PCR-EcoRI-2:
5' GGCGTG GACACC ATTTAT GA

Secondary PCR primer biotin 2, PCR-EcoRI-2-bt:
5' b GGCGTG GACACC ATTTAT GA
```

Step a) Providing the primary libraries

As in example 1, redundant positions during DNA-oligonucleotide synthesis were used to build the libraries.

Primary Library 1

```
Signal oligo 1, target-AvrII-1:
5' b GGGATA TAGCAA TCCTAC GGATCC AGCCAT

TCGACC TGACAA ACGTCC ATCCTA GGAGCT GAATTC ACGCTA

CTTTGC TACTCC ("GGATCC", "CCTAGG" and "GAATTC" are the
sequences recognised by the ds DNA restriction
enzymes BamHI (NEB, R0136L, 100 U/µl), AvrII
(NEB, R0174L, 4 U/µl) and EcoRI (NEB, R0101OL,
100 U/µl), respectively.

Noise oligo 1, library-e8-1:
5' GGGATA TAGCAA TCCTAC GCATCC MRKYAA KYMRMA

YRYMAT RMYKYT RYRMTC KRKKYA GAATTC ACGCTA CTTTGC

TACTCC
```

Primary Library 2

```
Signal oligo 2, target-AvII-2:
5' b GGCGTT TCTAAC AACGAA GGATCC AGCCAT TCGACC

TGACAA ACGTCC ATCCTA GGAGCT GAATTC ATAAAT GGTGTC

CACGCC

Nose oligo 2, library-e8-2:
5' GGCGTT TCTAAC AACGAA GGATCC MRKYAA KYMRMA

YRYMAT RMYKYT RYRMTC KRKKYA GAATTC ATAAAT GGTGTC

CACGCC (Actual redundancy: 2^27 = 1.3 x 10^8)
```

First Round

Step b) Contacting the target molecule with at least a subset of the primary library Primary libraries and hybridisation buffer (150 µl 20×SSC+50 µl 0.1% Triton X-100+84.5 µl H₂O) were aliquoted into tubes A-D according to the scheme below to give a total volume of 100 µl (6×SSC, 0.01% Triton X-100).

A) Library-1:
  56.9 µl hybridisation buffer
  40 µl 100 µM library-e8-1
  3.1 µl 10 pM target-AvrII-1
B) Negative control omitting signal in primary library, otherwise as A:
  58.9 µl hybridisation buffer
  40 µl 100 µM library-e8-1
  3.1 µl 0.01% Triton X100
C) Library-2:
  56.9 µl hybridisation buffer
  40 µl 100 µM library-e8-2
  3.1 µl 10 pM target-AvrII-2
D) Negative control omitting signal in primary library, otherwise as C:
  56.9 µl hybridisation buffer
  40 µl 100 µM library-e8-2
  3.1 µl 0.01% Triton X100

Next, the libraries (sample A to D) were heated to 94° C. for 5 minutes followed by incubation at 65° C. for 10 minutes.

As solid phase bound targets, streptavidin and avidin immobilised to two different solid supports were used. The use of two different solid phases (resins) could be favourable, because they may have a different background of non-specific binders. Streptavidin and avidin are very similar and both have a strong interaction with biotin. For this experiment, the idea is to mimic a situation where the same or similar targets have been immobilised on two different solid supports.

Equilibration of the solid phase bound target:

Solid phase I) 30% Streptavidin Sepharose High Performance beads in 20% EtOH, Amersham, 17-5113-01:

60 µl solid phase suspension was centrifuged to pellet the solid phase. The supernatant was disposed and 360 µl 6×SSC, 0.01% Triton X-100 added. After resuspension of the solid phase, it was again pelleted by centrifugation and the supernatant disposed. The solid phase was resuspended in 42 µl 6×SSC, 0.01% Triton X-100 to give a total volume of app. 60 µl.

Solid phase II) 50% Tetrameric Avidin Resin in 20% EtOH, Promega, V2591:

36 µl solid phase suspension was centrifuged to pellet the solid phase, otherwise as I.

20 µl equilibrated solid phase I was added to samples A and B and 20 µl equilibrated solid phase II was added to samples C and D. Next, samples A-D were incubated at 65° C. for 30 minutes with mixing in a table shaker.

Step c) Selecting the oligonucleotide species of the primary library that interact specifically with the target molecule After incubation with the solid phase bound target, samples were centrifuged, supernatant disposed, beads resuspended in 300 µl 10× wash buffer (1 M NaCl, 100 mM Tris-HCl pH 8) containing 0.01% Triton X-100 and re-incubated at 65° C. for 30 minutes with mixing. Then the samples were centrifuged, the supernatant disposed and beads resuspended in 300 µl 10× wash buffer. This was followed by a third wash where the samples were centrifuged, the supernatant disposed and beads resuspended in 300 µl 1× wash buffer. Next, the beads were pelleted by centrifugation and the supernatant disposed. Residual biotin binding sides on the solid phase were blocked by addition of 1 µl 20 mM Biotin (Sigma, B-4501) and the total volume of the samples adjusted to 20 µl by addition of app. 14 µl 1× wash buffer. This was followed by incubation at room-temperature for 5 minutes with mixing.

Step d) Amplifying selected oligonucleotides to create $0^{th}$ generation second libraries:

10 µl of samples A-D were added to two PCR mixes (I and II) each containing:
360 µl H$_2$O
50 µl 10× buffer (Bioline, BIO-21050)
15 µl 50 mM MgCl$_2$ (Bioline, BIO-21050)
20 µl dNTPs, 5 mM each (Bioline, BIO-39025)
5 µl polymerase (BIO-X-ACT long, Bioline, BIO-21050)
Next, primers were added as follows:
AI and BI: 20 µl 10 µM PCR-BamHI-1-bt+20 µl 10 µM PCR-EcoRI-1
AII and BII: 20 µl 10 µM PCR-BamHI-1+20 µl 10 µM PCR-EcoRI-1-bt
CI and DI: 20 µl 10 µM PCR-BamHI-2-bt+20 µl 10 µM PCR-EcoRI-2
CII and DII: 20 µl 10 µM PCR-BamHI-2+20 µl 10 µM PCR-EcoRI-2-bt As negative PCR controls, samples EI and EII, 1 µl 1× wash buffer was added to two PCR mixes each containing:
36 µl H$_2$O
5 µl 10× buffer
1.5 µl 50 mM MgCl$_2$
2 µl dNTPs, 5 mM each
0.5 µl polymerase
And primers added as follow:
E-I: 2 µl 10 µM PCR-BamHI-1+2 µl 10 µM PCR-EcoRI-1
E-II: 2 µl 10 µM PCR-BamHI-2+2 µl 10 µM PCR-EcoRI-2

As positive PCR controls, samples FI and FII, 1 µl 10 µM target-AvrII-1 (FI) and 1 µl 10 pM target-AvrII-2 (FII), respectively, were each added to a PCR mix containing:
36 µl H$_2$O
5 µl 10× buffer
1.5 µl 50 mM MgCl$_2$
2 µl dNTPs, 5 mM each
0.5 µl polymerase
And primers added as follow:
F-I: 2 µl 10 µM PCR-BamHI-1+2 µl 10 µM PCR-EcoRI-1
F-II: 2 µl 10 µM PCR-BamHI-2+2 µl 10 µM PCR-EcoRI-2

All samples were then aliquoted into PCR tubes and amplified using the following program:
Initial denaturation: 94° C., 5 min.
30 cycles: 94° C., 3 sec
61° C., 60 sec
72° C., 10 sec.
Final extension: 72° C., 5 min
After amplification, beads were removed from samples AI-DII by spin-filtration (Ultrafree-MC filter microporous 0.22 micron, Millipore, UFC3 0GV NB).

Step e) Monitoring the evolution of the secondary libraries

The $0^{th}$ generation secondary libraries represent an amplification of the information output (both noise and signal) from the primary selections.

Using cross-hybridisation, the signal will be preferentially amplified to create later generation secondary libraries.

5 µl of samples AI, AII, BI, BII, CI, CII, DI, DII, EI, EII, FI and FII were added 2 µl AvrII+1.6 µl buffer 2 (NEB, B7002S)+7.4 µl H$_2$O and incubated at 37° C. for 2 hours.

As negative restriction controls, identical samples but with 2 µl H$_2$O instead of AvrII were incubated at 37° C. for 2 hours.

The samples were then added 4 µl 30% glycerol and resolved on a 4% GTG (BioWhittaker (BMA), 50084) agarose gel using 1×TBE as running buffer.

Figure 9:
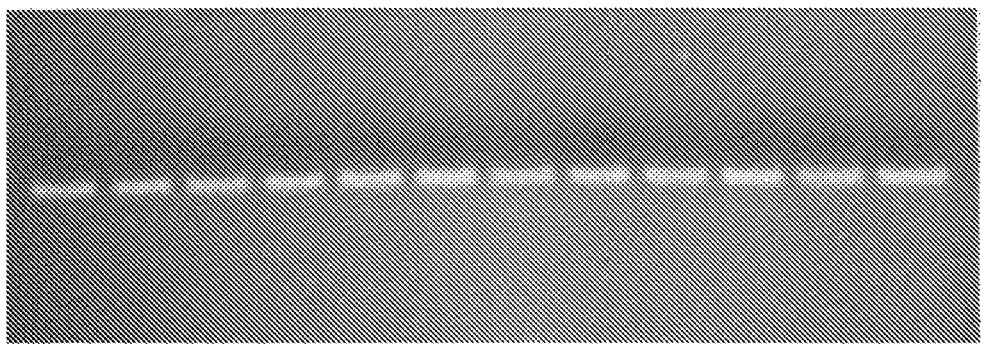
Figure 9:
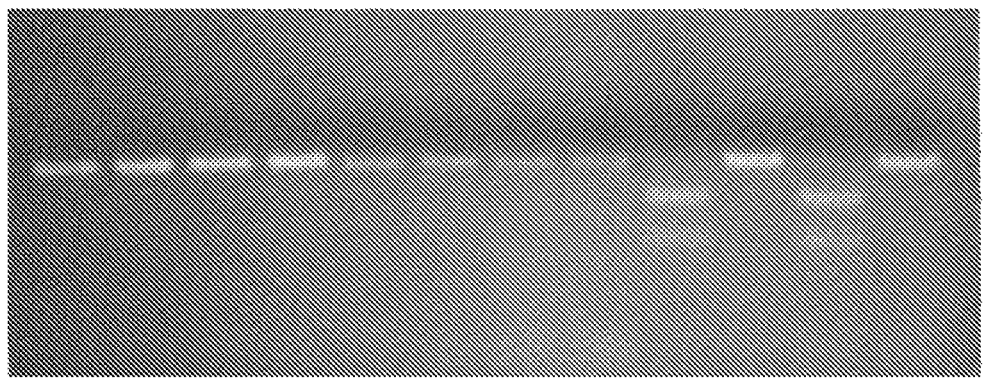

FIG. 9A:+/− AvrII of samples AI, AII, BI, BII, CI and CII.
FIG. 9B:+/− AvrII of sample DI, DII, EI, EII, FI and FII.

Restriction was only seen for the positive controls, FI and FII, wherefore the signal was amplified by cross-hybridisation of the $0^{th}$ generation secondary libraries.

Step f) Preparing secondary libraries for cross-hybridisation

Secondary libraries was immobilised on streptavidin beads, digested with either EcoRI or BamHI to release truncated oligonucleotides, devoid of 3'-fixed regions.

Immobilisation of $0^{th}$ Generation Secondary Libraries

200 µl 30% Streptavidin Sepharose High Performance beads in 20% EtOH were centrifuged to pellet the solid phase. The supernatant was disposed and 1200 µl 6×SSC, 0.01% Triton X-100 added. After resuspension of the solid phase, it was again pelleted by centrifugation and the supernatant disposed. The solid phase was resuspended in 140 µl 6×SSC, 0.01% Triton X-100 to give a total volume of app. 200 µl.

Samples AI-DII (495 µl PCR-product) were added 200 µl 20×SSC-+20 µl equilibrated streptavidin beads. Next, samples AI-DII were incubated at RT for 30 minutes with mixing. In the first wash, samples were centrifuged, supernatant disposed, beads resuspended in 300 µl 10× wash buffer, 0.01% Triton X-100 and re-incubated at RT for 30 minutes with mixing. For second wash, the samples were centrifuged, supernatant disposed and beads resuspended in 300 µl buffer R (50 mM Tris-HCl pH 8, 10 mM MgCl$_2$, 100 mM NaCl).

Release of truncated oligonucleotides from streptavidin beads by restriction:

Next, the beads were pelleted by centrifugation and supernatant disposed. The beads of samples AI, BI, CI and DI were resuspended in 96 µl of 1× BamHI-buffer containing 1×BSA, while beads of AII, BII, CII and DII were resuspended in 96 µl of 1×EcoRI-buffer. Next, 4 µl of BamHI (100 U/µl) was added to samples AI, BI, CI and DI, and 4 µl of EcoRI (100 U/µl) to sample AII, BII, CII and DII, and samples incubated at 37° C. for 2 hours with gentle mixing.

The supernatant containing truncated oligonucleotides of the restricted samples AI-DII were collected by spin-filtration; 1 min centrifugation at 1000 g followed by a second elution with 100 µl buffer R and 30 sec. centrifugation at 20,000 g and pooling of the two eluates. The samples were then extracted with 200 µl phenol, extracted with 200 µl chloroform and added 1 µl glycogen and ethanol precipitated by adding 20 µl 3M NaAc pH 4.5 and 400 µl 95% EtOH and, incubation at −80° C. 20 minutes, centrifugation at 0° C., 20,000 g for 40 minutes, disposal of the supernatant, and air drying of the pellet before dissolution in 50 µl 0.01% Triton X-100 by incubation at RT for 30 minutes with mixing. Next, the samples were desalted by gel-filtration on G25 columns (MicroSpin G-25 columns, Amersham, 27-5325-01). Finally, 5 µl of samples AI, AII, BI, BII, CI, CII, DI, DII, together with 2.5 and 5 µl of a 25 bp DNA ladder, were analysed on a 4% GTG agarose gel using 1×TBE as running buffer (not shown).

15 µl of the purified samples AII, AII, DI, DII and 10 µl of the purified samples BI, BII, CI, CII were estimated to contain app 1 pmol.

Step-g) Cross-hybridisation

Cross-Hybridisation of Truncated ($0^{th}$-Generation) Oligonucleotides

Cross-hybridisation was performed by adding truncated oligonucleotides to 25 µl hybridisation buffer (300 µl 5 M NaCl+15 µl 1 M Tris pH 8+15 µl 1% Triton X-100+420 µl H$_2$O) according to the scheme below.

25 µl Hybridisation Buffer+

AI+CII:
a-1: 15 µl 10× diluted AI (app 0.1 pmol; PCR-EcoRI-1-N)+15 µl 10× diluted CII (app 0.1 pmol; PCR-BamHI-2-NS)
a-2: 15 µl 100× diluted AI+10 µl 100× diluted CII
a-3: 15 µl 1,000× diluted AI+10 µl 1,000× diluted CII
BI+DII:
b-1: 10 µl 10× diluted BI (app 0.1 pmol; PCR-EcoRI-1-N)+15 µl 10× diluted DII (app 0.1 pmol; PCR-BamHI-2-N)
b-2: 10 µl 100× diluted BI+15 µl 100× diluted DII
b-3: 10 µl 1,000× diluted BI+15 µl 1,000× diluted DII
CI+AII:
c-1: 10 µl 10× diluted CI (app 0.1 pmol; PCR-EcoRI-2-NS)+15 µl 10× diluted AII (app 0.1 pmol; PCR-BamHI-1-NS)
c-2: 10 µl 100× diluted CI+15 µl 100× diluted AII
c-3: 10 µl 1,000× diluted CI+15 µl 1,000× diluted AII
DI+BII:
d-1: 15 µl 10× diluted DI (app 0.1 pmol; PCR-EcoRI-2-N)+10 µl 10× diluted BII (app 0.1 pmol; PCR-BamHI-1-N)
d-2: 15 µl 100× diluted DI+10 µl 100× diluted BII
d-3: 15 µl 1,000× diluted DI+10 µl 1,000× diluted BII
Controls:
e: 15 µl 10× diluted AI+10 µl 0.01% Triton X-100
f: 10 µl 10× diluted BI+15 µl 0.01% Triton X-100
g: 10 µl 10× diluted CII+15 µl 0.01% Triton X-100
h: 15 µl 10× diluted DII+10 µl 0.01% Triton X-100
i: 25 µl 0.01% Triton X-100
j: 10 µl 10× diluted CI+15 µl 0.01% Triton X-100
k: 15 µl 10× diluted DI+10 µl 0.01% Triton X-100
l: 15 µl 10× diluted AII+10 µl 0.01% Triton X-100
m: 10 µl 10× diluted BII+15 µl 0.01% Triton X-100
n: 25 µl 0.01% Triton X-100

EcoRI-1, EcoRI-2, BamHI-1 and BamHI-2 indicate the different fixed sequences, N indicates negative controls without signal-oligo, NS indicates libraries with signal (noise+signal), i.e. PCR-EcoRI-1-NS contains fixed region EcoRI-1 and both signal and noise oligos Next, the libraries (tubes a-1 to n) were heated to 94° C. for 5 minutes followed by incubation at 65° C. for 1 h for cross-hybridisation.

PCR-Amplification

Two PCR mixes (I and II) were prepared each containing 432 µl H$_2$O+60 µl 10× buffer+18 µl 50 mM MgCl$_2$+24 µl dNTPs, 5 mM each+6 µl polymerase.

24 µl 10 µM PCR-EcoRI-1+24 µl 10 µM PCR-BamHI-2 were added to mix I

24 µl 10 µM PCR-EcoRI-2+24 µl 10 µM PCR-BamHI-1 were added to mix II.

Each mix was then transferred to PCR tubes (11×49 µl), where after 1 µl of hybridisation, mix a-1, a-2, a-3, b-1, b-2, b-3, e, f, g, h, i was added to PCR mix I (11×1 µl) and 1 µl of hybridisation mix c-1, c-2, c-3, d-1, d-2, d-3, j, k, l, m, n was added to PCR mix II (11×1 µl).

Amplification was performed using the following program:
Extension 72° C., 5 min
Initial denaturation: 94° C., 5 min
30 cycles: 94° C., 30 sec
61° C., 60 sec
72° C., 10 sec
Final extension: 72° C., 5 min After amplification, 5 µl of the PCR samples was added 2.5 µl H$_2$O+2.5 µl 30% glycerol and resolved together with a 25 bp DNA ladder on 4% GTG agarose gels using 1×TBE as running buffer.

Using 0.1 and 0.01 pmol truncated Oligonucleotide for cross-hybridisation and subsequent amplification gave strong bands, while using 0.001 pmol gave only weak bands.

Step h) Monitoring evolution of the secondary libraries by restriction analysis

The following PCR samples were desalted with a G25 column: a-2, a-3, b-2, b-3, c-2, c-3, d-2 and d-3 and F-I and F-II (positive controls).

6 µl of the desalted samples were each added 6.4 µl H$_2$O+2 µl AvrII, 1.6 µl buffer 2 and incubated at 37° C. for 2 hours.

As restriction controls, samples with 2 µl H$_2$O instead of AvrII were incubated at 37° C. for 2 hours.

The samples were then added 4 µl 30% glycerol and resolved on a 4% GTG agarose gel.

Figure 10:
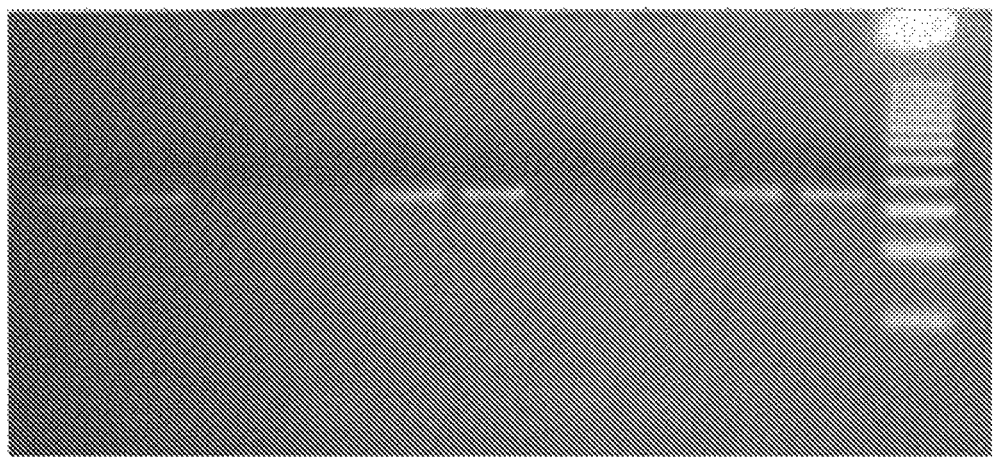
Figure 10:
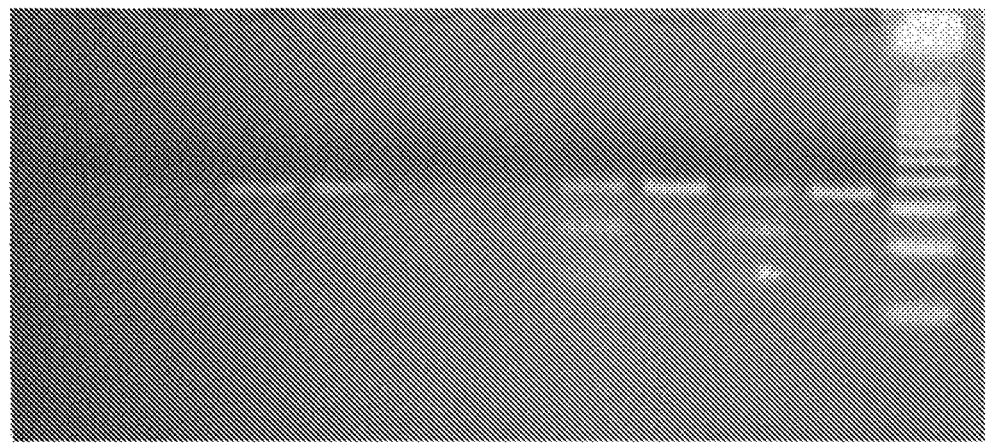

FIG. 10A: +/− AvrII of a-2, a-3, b-2, b-3, c-2 and 3 µl of a 25 bp DNA ladder.

FIG. 10B: +/− AvrII of c-3, d-2, d-3, F-I and F-II and 3 µl of a 25 bp DNA ladder.

Some of the bands were very faint. However, no restriction was seen for the samples, except for the controls. Therefore, the experiment was continued with another round.

Step i) Repetitions—Second round

Step f) Preparing Oligonucleotides for cross-hybridisation

A second PCR-amplification on $1^{th}$ generation secondary libraries from the previous step f was first performed to add capture groups (biotin) to the secondary libraries and to increase their amount.

Eight PCR mixes (AI to DII) was prepared, each containing 350 µl H$_2$O+50 µl 10× buffer+15 µl 50 mM MgCl$_2$+ 20 µl dNTPs, 5 mM each+5 µl Bio-XACT polymerase.

Then G25 desalted samples (PCR-products) from step f was added:
AI and AII: 20 µl 10e4× diluted a-2
BI and BII: 20 µl 10e4× diluted b-2
CI and CII: 20 µl 10e4× diluted c-2
DI and DII: 20 µl 10e4× diluted d-2
Then primers:
AI and BI: 20 µl 10 µM PCR-EcoRI-1+20 µl 10 µM PCR-BamHI-2-bt
AII and BII: 20 µl 10 µM PCR-EcoRI-1-bt+20 µl 10 µM PCR-BamHI-2
CI and DI: 20 µl 10 µM PCR-EcoRI-2+20 µl 10 µM PCR-BamHI-1-bt
CII and DII: 20 µl 10 µM PCR-EcoRI-2-bt+20 µl 10 µM PCR-BamHI-1

And amplification was performed using the following program:
Initial denaturation: 94° C., 5 min
30 cycles: 94° C., 30 sec
61° C., 60 sec
72° C., 10 sec
Final extension: 72° C., 5 min 5 µl PCR (AI, AII, BI, BII, CI, CII, DI and DII) was added 2.5 µl H₂O and 2.5 µl of the 25 bp DNA ladder (app 1.2 pmol) was added 5 µl H₂O, these were then added 2.5 µl 30% glycerol and resolved on a 4% GTG agarose gel to verify that PCR-products of the correct length had been generated. (data not shown).

Immobilisation of Amplified Oligonucleotides

Amplified Oligonucleotides was immobilised on equilibrated Streptavidin Sepharose as described in the previous round, step f Release of truncated Oligonucleotides from Streptavidin Sepharose by restriction:
As described in the previous round, step f.
5 µl of the purified samples AI, AI, BI, BII, CI, CII, DI, DII together with 2.5 and 5 µl of the 25 bp DNA ladder were analysed on a 4% GTG agarose gel using 1×TBE as running buffer (data not shown).
4 µl of the purified samples AI to DII were estimated to contain app 2 pmol.

Step g) Cross-hybridisation
Truncated 1st generation secondary libraries (samples AI-DII) and hybridisation buffer (300 µl 5 M NaCl+15 µl 1 M Tris pH 8+15 µl 1% Triton X-100+570 µl H₂O) were aliquoted according to the scheme below.

30 µl Hybridisation Buffer+

AI+CII:
a-1: 20 µl of 100× diluted AI (app 0.1 pmol; PCR-EcoRI-1-S)+100× diluted CII (app 0.1 pmol; PCR-BamHI-1-S)
a-2: 20 µl of 1000× diluted AI+1000× diluted CII
a-3: 20 µl of 10,000× diluted AI+10,000× diluted CII
a-4: 20 µl of 100,000× diluted AI+100,000× diluted CII
BI+DII:
b-1: 20 µl of 100× diluted BI (PCR-EcoRI-1-N)+100× diluted DII (PCR-BamHI-1-N)
b-2: 20 µl of 1000× diluted BI+1000× diluted DII
b-3: 20 µl of 10,000× diluted BI+10,000× diluted DII
b-4: 20 µl of 100,000× diluted BI+100,000× diluted DII
CI+AII:
c-1: 20 µl of 100× diluted CI (PCR-EcoRI-2-S)+100× diluted AII (PCR-BamHI-2-S)
c-2: 20 µl of 1000× diluted CI+1000× diluted AII
c-3: 20 µl of 10,000× diluted CI+10,000× diluted AII
c-4: 20 µl of 100,000× diluted CI+100,000× diluted AII
DI+BII:
d-1: 20 µl of 100× diluted DI (PCR-EcoRI-2-N)+100× diluted BII (PCR-BamHI-2-N)
d-2: 20 µl of 1000× diluted DI+1000× diluted BII
d-3: 20 µl of 10,000× diluted DI+10,000× diluted BII
d-4: 20 µl of 100,000× diluted DI+100,000× diluted BII
Controls:
e: 20 µl 100× diluted AI
f: 20 µl 100× diluted CII
g: 20 µl 100× diluted BI
h: 20 µl 100× diluted DII
i: 20 µl 0.01% Triton X-100
j: 20 µl 100× diluted CI
k: 20 µl 100× diluted AII
i: 20 µl 100× diluted DI
m: 20 µl 100× diluted BII
n: 20 µl 0.01% Triton X-100

Next, the libraries (tubes a-1 to n) were heated to 94° C. for 5 minutes followed by incubation at 65° C. for 1 h.

PCR-Amplification

Two PCR mixes (I and II) were prepared each containing 504 µl H₂O+70 µl 10× buffer+21 µl 50 mM MgCl₂+28 µl dNTPs, 5 mM each+7 µl polymerase.
28 µl 10 µM PCR-EcoRI-1+28 µl 10 µM PCR-BamHI were added to mix I
28 µl 10 µM PCR-EcoRI-2+28 µl 10 µM PCR-BamHI-2 were added to mix II
Each mix was then transferred to PCR tubes (13×49 µl), where after 1 µl of hybridised samples a-1, a-2, a-3, a-4, b-1, b-2, b-3, b-4, e, f, g, h, i was added to PCR mix I and 1 µl of samples c-1, c-2, c-3, c-4, d-1, d-2, d-3, d-4, j, k, l, m, n was added to PCR mix II.
Amplification was performed using the following program:
Extension 72° C., 5 min
Initial denaturation: 94° C., 5 min
30 cycles: 94° C., 30 sec
61° C., 60 sec
72° C., 10 sec
Final extension: 72° C., 5 min After amplification, 5 µl of the PCR samples was added 2.5 µl H₂O+2.5 µl 30% glycerol and resolved together with a 25 bp DNA ladder on 4% GTG agarose gels using 1×TBE as running buffer.
Samples a-1, a-2, a-3, b-1, b-2, b-3, c-1, c-2, c-3, d-1, d-2 and d-3 all resulted in significant amount of a PCR product of the same length as the original library (data not shown).

Figure 11:
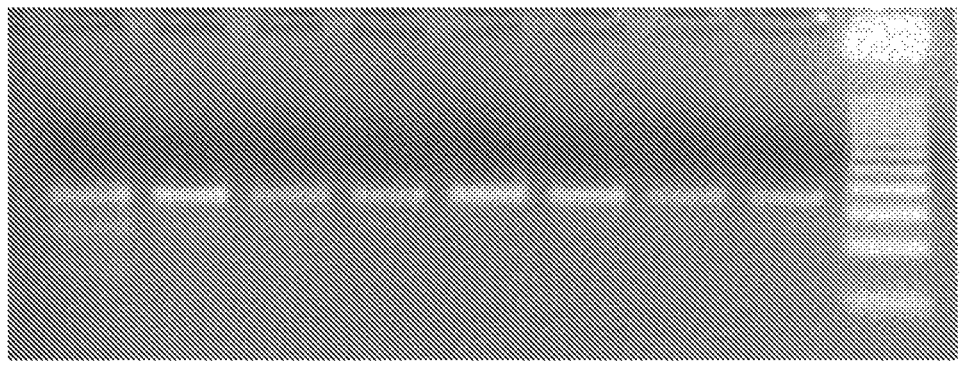
Figure 11:
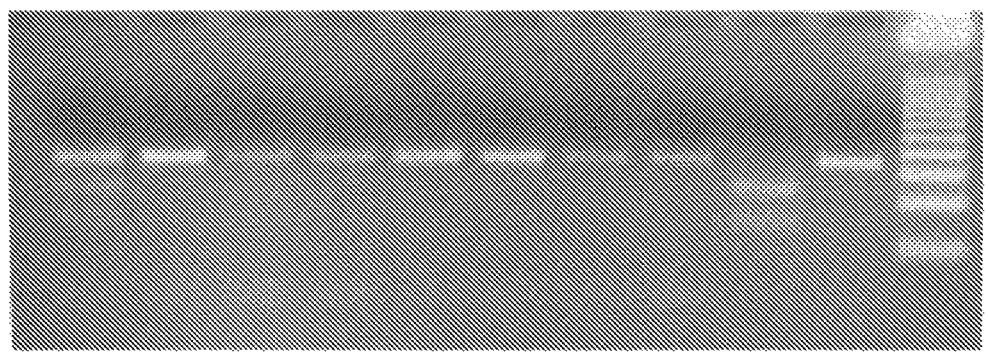

Step h) Monitoring evolution of the secondary libraries by restriction analysis
The following PCR samples ($2^{nd}$ generation secondary libraries) were desalted with a G25 column: a2, a3, b2, b3, c2, c3, d2 and d3.
6 µl of the desalted samples and of a positive control, FI from the first round, were each added 2 µl AvrII, 1.6 µl buffer 2 and 6.4 µl and incubated at 37° C. ON.
As restriction controls, samples with 2 µl H₂O instead of AvrII were incubated at 37° C. ON.
The samples were then added 4 µl 30% glycerol and resolved on a 4% GTG agarose gel.
FIG. 11A: +/− AvrII of a-2, a-3, b-2, b-3 and 3 µl of a 25 bp DNA ladder.
FIG. 11B: +/− AvrII of c-2, c-3, d-2, d-3, FI and 3 µl of a 25 bp DNA ladder.
ON incubation lead to more than 90% cleavage of the positive control, FI, and approximately 20% of a-2 and c-2 was cleaved. Thus, the signal oligonucleotide had (after two cross-hybridisations) evolved to constitute around 20% of the two $2^{nd}$ generation secondary libraries compared to 1 in $1,3×10^8$ in the original primary libraries, which corresponds to enrichments of app. $2,6×10^7$ (data not shown).

Step i) Repetitions—Third round
Step f) Preparing oligonucleotides for cross-hybridisation
A second PCR-amplification on $2^{nd}$ generation secondary libraries from the previous step f) was first performed to add capture groups (biotin) to the secondary libraries and to increase their amount.

Eight PCR mixes (AI to DII) was prepared, each containing 350 µl H$_2$O+50 µl 10× buffer+15 µl 50 mM MgCl$_2$+ 20 µl dNTPs, 5 mM each+5 µl polymerase.

Then G25 desalted samples (PCR-products) from the previous step f was added:

AI and AII: 20 µl 10e4× diluted a-2
BI and BII: 20 µl 10e4× diluted b-2
CI and CII: 20 µl 10e4× diluted c-2
DI and DII: 20 µl 10e4+ diluted d-2

Then primers:

AI and BI: 20 µl 10 µM PCR-EcoRI-1+20 µl 10 µM PCR-BamHI-1-bt
AII and BII: 20 µl 10 µM PCR-EcoRI-1-bt+20 µl 10 µM PCR-BamHI-1
CI and DI: 20 µl 10 µM PCR-EcoRI-2+20 µl 10 µM PCR-BamHI-2-bt
CII and DII: 20 µl 10 µM PCR-EcoRI-2-bt+20 µl 10 µM PCR-BamHI-2

And amplification was performed using the following program:

Initial denaturation: 94° C., 5 min
30 cycles: 94° C., 30 sec
61° C., 60 sec
72° C., 10 sec
Final extension: 72° C., 5 min 5 µl PCR (AI, AII, BI, BII, CI, CII, DI and DII) was added 2.5 µl H$_2$O and 2.5 µl of the 25 bp DNA ladder (app 1.2 pmol) was added 5 µl H$_2$O, these were then added 2.5 µl 30% glycerol and resolved on a 4% GTG agarose gel gel to verify that PCR-products of the correct length had been generated, (data not shown).

Immobilisation of Amplified Oligonucleotides

Amplified Oligonucleotides was immobilised on equilibrated Streptavidin Sepharose as described in the first round, step f Release of truncated Oligonucleotides from Streptavidin Sepharose by restriction:

As described in the first round, step f.

5 µl of the purified samples AI, AI, BI, BII, CI, CII, DI, DII together with 2.5 and 5 µl of the 25 bp DNA ladder were analysed on a 4% GTG agarose gel using 1×TBE as running buffer (data not shown).

5 µl of the purified samples AI to DII were estimated to contain app 2 pmol.

Step g) Cross-hybridisation

Truncated 2$^{nd}$ generation secondary libraries (sample AI-DII) and hybridisation buffer (300 µl 5 M NaCl+15 µl 1 M Tris pH 8+15 µl 1% Triton X-100+570 µl H$_2$O) were aliquoted according to the scheme below.

25 µl Hybridisation Buffer+

AI+CII:

a-1: 25 µl of 1,000× diluted AI (app 0.01 pmol; PCR-EcoRI-1-S)+1,000× diluted CII (app 0.01 pmol; PCR-BamHI-2-S)
a-2: 25 µl of 10,000× diluted AI30 10,000× diluted CII
a-3: 25 µl of 100,000× diluted AI+100,000× diluted CII
a-4: 25 µl of 1,000,000× diluted AI+1,000,000× diluted CII

BI+CII:

b-1: 25 µl of 1,000× diluted BI PCR-EcoRI-1-N)+1,000× diluted DII (PCR-BamHI-2-N)
b-2: 25 µl of 10,000× diluted BI30 10,000× diluted DII
b-3: 25 µl of 100,000× diluted BI+100,000× diluted DII
b-4: 25 µl of 1,000,000+ diluted BI+1,000,000× diluted DII

CI+AII:

c-1: 25 µl of 1,000× diluted CI (PCR-EcoRI-2-S)+1,000× diluted AII (PCR-BamHI-1-S)
c-2: 25 µl of 10,000× diluted CI30 10,000× diluted AII
c-3: 25 µl of 100,000× diluted CI+100,000× diluted AII
c-4: 25 µl of 1,000,000× diluted CI+1,000,000× diluted AII

DI+BII:

d-1: 25 µl of 1,000× diluted DI (PCR-EcoRI-2-N)+1,000× diluted BII (PCR-BamHI-1-N)
d-2: 25 µl of 10,000× diluted DI30 10,000× diluted BII
d-3: 25 µl of 100,000× diluted DI+100,000× diluted BII
d-4: 25 µl of 1,000,000× diluted DI+1,000,000× diluted BII Controls:

e: 25 µl 1,000× diluted AI
f: 25 µl 1,000× diluted CII
g: 25 µl 1,000× diluted BI
h: 25 µl 1,000× diluted DII
i: 25 µl 0.01% Triton X-100
j: 25 µl 1,000× diluted CI
k: 25 µl 1,000× diluted AII
l: 25 µl 1,000× diluted DI
m: 25 µl 1,000× diluted BII
n: 25 µl 0.01% Triton X-100

Next, the libraries (tubes a-1 to n) were heated to 94° C. for 5 minutes followed by incubation at 65° C. for 1 h.

PCR-Amplification

Two PCR mixes (I and II) were prepared each containing 504 µl H$_2$O+70 µl 10× buffer+21 µl 50 mM MgCl$_2$+28 µl dNTPs, 5 mM each+7 µl polymerase.

28 µl 10 µM PCR-EcoRI-1+28 µl 10 µM PCR-BamHI-2 were added to mix I
28 µl 10 µM PCR-EcoRI-2+28 µl 10 µM PCR-BamHI-1 were added to mix II Each mix was then transferred to PCR tubes (13×49 µl), where after 1 µl of hybridised sample a-1, a-2, a-3, a-4, b-1, b-2, b-3, b-4, e, f, g, h, i was added to a PCR mix I and 1 µl of sample c-1, c-2, c-3, c-4, d-1, d-2, d-3, d-4, j, k, l, m, n was added to PCR mix II.

Amplification was performed using the following program:

Extension 72° C., 5 min
Initial denaturation: 94° C., 5 min
30 cycles: 94° C., 30 sec
61° C., 60 sec
72° C., 10 sec
Final extension: 72° C., 5 min After amplification, 5 µl of the PCR samples was added 2.5 µl H$_2$O+2.5 µl 30% glycerol and resolved together with a 25 bp DNA ladder on 4% GTG agarose gels using 1×TBE as running buffer (data not shown). Only a-1, a-2, a-3, b-1, b-2, c-1, c-2, c-3, d-1 and d-2 resulted in significant amounts of PCR product.

Step h) Monitoring evolution of the secondary libraries by restriction analysis

The following PCR samples (3$^{rd}$ generation secondary libraries) were desalted with a G25 column: a2, a3, b2, c2, c3 and d2.

6 µl of the desalted samples and 6 µl of a positive control, FI from the first round, were each added 2 µl AvrII, 1.6 µl buffer 2 and 6.4 µl H$_2$O and incubated at 37° C. for 4 h.

As restriction controls, samples with 2 µl H₂O instead of AvrII were incubated at 37° C. 4 hours.

The samples were then added 4 µl 30% glycerol and resolved on a 4% GTG agarose gel.

Figure 12:
Figure 12:
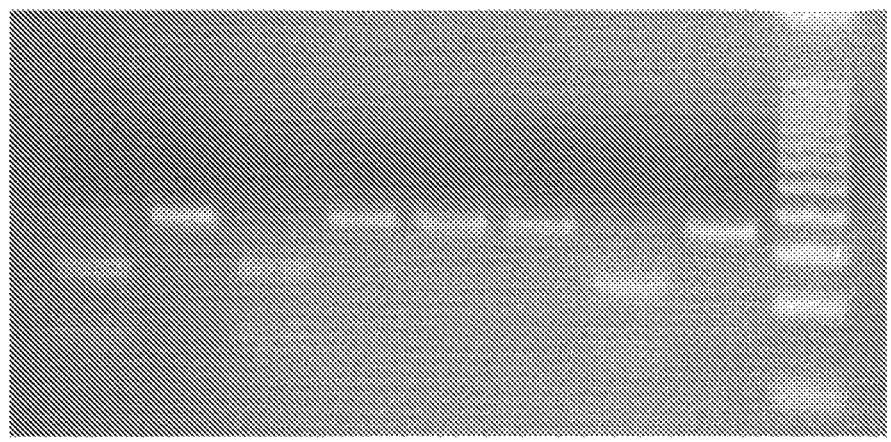

FIG. 12A: +/− AvrII of a-2, a-3, b-2 and 3 µl of a 25 bp DNA ladder.

FIG. 12B: +/− AvrII of c-2, c-3, d-2, FI and 3 µl of a 25 bp DNA ladder.

Approximately, 90% cleavage of the positive control, FI, was observed and also approximately 90% of a-2, a-3, c-2 and c-3 was cleaved. Thus, 3$^{rd}$ generation secondary libraries constituted almost solely of the signal oligonucleotide and consequently an enrichment of approximately 1,3×10⁸ fold was obtained.

Conclusion

The signal oligo was enriched from 1 in 10e8 to close to 1 in 1 (100%) by one selection against streptavidin followed by three successive rounds of PCR amplification, removal of one fixed region, hybridisation and extension. In other words, an oligonucleotide library was evolved from containing the signal sequence in a ratio of 1 in 10e8 to close to 1 in 1.

Importantly, the control library without a signal oligo did not evolved to contain any signal detectable restriction digestion.

Example 4

Screening a 10¹⁰ library with a predetermined fold of selection

In this, example, a true selection of the primary library was not done. Instead the primary library was prepared such as to mimic a primary library that has already been selected. More specifically, the signal oligonucleotide was diluted into a 10¹⁰ library, but such as to be in 10⁵ fold excess of the other species in the library, i.e. mimicking that a 10⁵ fold selection had been done. Otherwise, the process was similar to example 3.

DNA-oligonucleotides used for positive restriction control:

```
HD1-PCR-1;
5'GATGAT AGTAGT TCGTCG TCAC

HD1-PCR-2:
5'-biotin-GCAGCA ACTACT CATCAT GACT

StuI-template:
5'GATGAT AGTAGT TCGTCG TCAC CGAGGT TATAGC AGGCCT

CGTTTC GCTCCG ACTAGC T AGTC ATGATG AGTAGT TGCTGC
```

PCR-Primers

Set 1:

```
Primary PCR primer 1, PCR-BamHI-1:
5' GGGATA TAGCAA TCCTAC GG

Primary PCR primer biotin 1, PCR-BamHI-1-bt:
5' b GGGATA TAGCAA TCCTAC GG

Secondary PCR primer 1, PCR-EcoRI-1:
5' GGAGTA GCAAAG TAGCGT GA

Secondary PCR primer biotin 1, PCR-EcoRI-1-bt:
5' b GGAGTA GCAAAG TAGCGT GA
```

Set 2:

```
Primary PCR primer 2, PCR-BamHI-2:
5' GGCGTT TCTAAC AACGAA GG

Primary PCR primer biotin 2, PCR-BamHI-2-bt:
5' b GGCGTT TCTAAC AACGAA GG

Secondary PCR primer 2, PCR-EcoRI-2:
5' GGCGTG GACACC ATTTAT GA

Secondary PCR primer biotin 2, PCR-EcoRI-2-bt:
5' b GGCGTG GACACC ATTTAT GA
```

Step a) Providing the primary libraries

As in example 1, redundant positions during DNA-oligonucleotide synthesis are used to build the libraries.

Primary Library 1

```
Signal oligo 1, target-StuI-1:
5' b GGGATA TAGCAA TCCTAC GGATCC ACCTAG TTGGAG

CGAACA GGCCTT GCTATA ACCTTG GAATTC ACGCTA CTTTGC

TACTCC
```

"GGATCC", "AGGCCT" and "GAATTC" are the sequences recognised by the ds DNA restriction enzymes BamHI (NEB, R0136L, 100 U/µl), StuI (NEB, R0187L, 10 U/µl) and EcoRI (NEB, R01010L, 100 U/µl), respectively.)

```
Noise oligo 1, library-e10-1:
5' GGGATA TAGCAA TCCTAC GGATCC MYDKMC KYHRMA

YRBMMT RRDMYA RYVMKC MYDKYA GAATTC ACGCTA CTTTGC

TACTCC
```

Primary Library 2

```
Signal oligo 2, target-StuI-2:
5' b GGCGTT TCTAAC AACGAA GGATCC ACCTAG TTGGAG

CGAACA GGCCTT GCTATA ACCTTG GAATTC ATAAAT GGTGTC

CACGCC

Noise oligo 2, library-e10-2:
5' GGCGTT TCTAAC AACGAA GGATCC MYDKMC KYHRMA

YRBMMT RRDMYA RYVMKC MYDKYA GAATTC ATAAAT GGTGTC

CACGCC
```

(Actual redundancy: $2^{24} \times 3^6 = 1.2 \times 10^{10}$)

First Round

Step b+c) Contacting the target molecule with at least a subset of the primary library and selecting the oligonucleotides of the primary library that interact specifically with the target molecule As mentioned above, the primary libraries were not contacted with the target molecule. Instead primary libraries were prepared such as to mimic a primary library that had already been selected against the target to give a 10⁵-fold enrichment:

DNA oligonucleotides and 2× buffer (200 mM NaCl, 20 mM Tris pH 8, 0.01% Triton X-100) were aliquoted into tubes A-D according to the scheme below to give a total volume of 22 µl (100 mM NaCl, 10 mM Tris pH 8, 0.01% Triton X-100).

A) Library-1:
11 µl 2× buffer
6 µl 10 nM library-e10-1
5 µl 0.1 pM target-StuI-1

B) Negative control omitting signal in primary library, otherwise as A:
11 µl 2× buffer
6 µl 10 nM library-e10-1
5 µl 0.01% Triton X100

C) Library-2:
11 µl 2× buffer
6 µl 10 nM library-e10-2
5 µl 0.1 pM target-StuI-2

D) Negative control omitting signal in primary library, otherwise as C:
11 µl 2× buffer
6 µl 10 nM library-e10-2
5 µl 0.01% Triton X100

Step d) Amplifying hybridised oligonucleotides to create $0^{th}$ generation second libraries:

8 PCR mixes were prepared each containing:
396 µl H$_2$O
55 µl 10× buffer (Bioline, BIO-21050)
16.5 µl 50 mM MgCl$_2$ (Bioline, BIO-21050)
22 µl dNTPs, 5 mM each (Bioline, BIO-39025)
5.5 µl polymerase (BIO-X-ACT long, Bioline, BIO-21050)

Next, primers were added as follows:
A-I and B-I: 22 µl 10 µM PCR-BamHI-1-bt+22 µl 10 µM PCR-EcoRI-1
A-II and B-II: 22 µl 10 µM PCR-BamHI-1+22 µl 10 µM PCR-EcoRI-1-bt
C-I and D-I: 22 µl 10 µM PCR-BamHI-2-bt+22 µl 10 µM PCR-EcoRI-2
C-II and D-II: 22 µl 10 µM PCR-BamHI-2+22 µl 10 µM PCR-EcoRI-2-bt As negative PCR controls, 49 µl from each of the above PCR mixes was added 1 µl 1× wash buffer.

The remaining 490 µl was added 10 µl of the samples A-D representing selected primary libraries (A to A-I and A-II, B to B-I and B-II, C to C-I and C-II, D to D-I and D-II) and transferred to 5 PCR-tubes (5×100 µl).

As a positive PCR and restriction control, sample E, 6 µl 1 nM StuI-template was added to a PCR mix containing:
31 µl H$_2$O
5 µl 10× buffer
1.5 µl 50 mM MgCl$_2$
2 µl dNTPs, 5 mM each
2 µl 10 µM HD1-PCR-1
2 µl 10 µM HD-PCR-2
0.5 µl polymerase Amplification was done using the following program:
Initial denaturation: 94° C., 5 min.
30 cycles: 94° C., 30 sec
61° C., 60 sec
72° C., 10 sec.
Final extension: 72° C., 5 min
After amplification, the identical samples were pooled.

Step e) Monitoring the evolution of the secondary libraries

The $0^{th}$ generation secondary libraries represent an amplification of the information output (both noise and signal) from the primary selections. Thus, the signal oligonucleotide should still be enriched $10^5$ compared to noise oligonucleotides.

5 µl of negative PCR controls were added 2.5 µl H$_2$O and 2.5 µl of a 25 bp DNA ladder (Promega, #G4511) was added 5 µl H$_2$O. The samples were added 2.5 µl 30% glycerol and resolved on a 4% GTG (BioWhittaker (BMA), 50084) agarose gel using 1×TBE as running buffer. As expected, no PCR product was seen for any of the samples (data not shown).

5 µl of samples AI, AII, BI, BII, CI, CII, DI, DII, E were added 1 µl StuI+1 µl buffer 2 (NEB, B7002S)+3 µl H$_2$O and incubated at 37° C. for 3 hours.

As negative restriction controls, identical samples but with 1 µl H$_2$O instead of StuI were incubated at 37° C. for 3 hours.

The samples were then added 3 µl 30% glycerol and resolved on a 4% GTG agarose gel.

Figure 13:
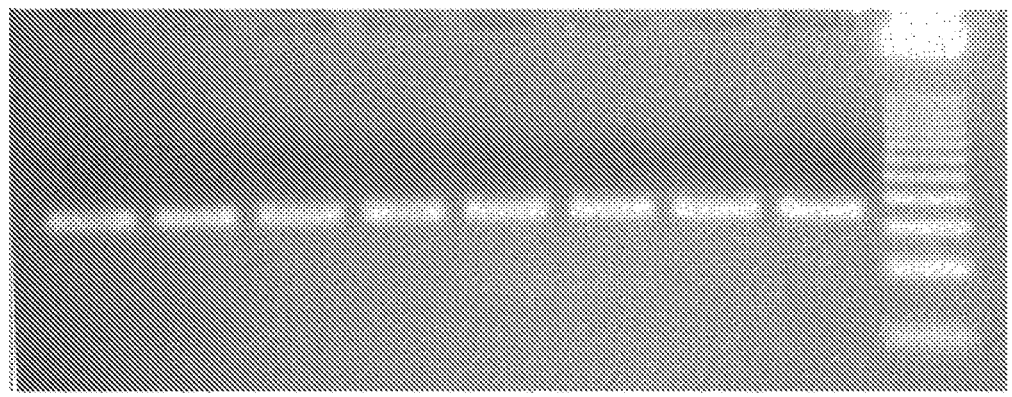
Figure 13:
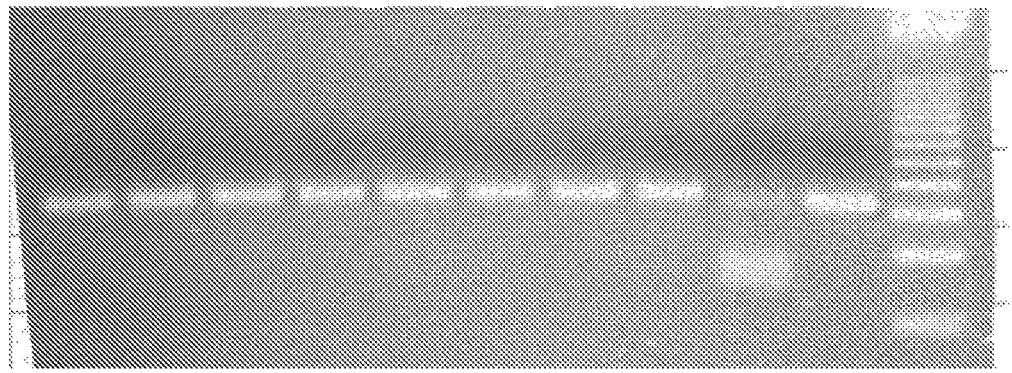

FIG. 13A: +/− StuI of samples AI, AII, BI, BII and 25 bp DNA ladder (2.5 µl).

FIG. 13B: +/− StuI of samples CI, CII, DI, DII, E and 25 bp DNA ladder (2.5 µl).

As expected, restriction was only seen for the positive control, E, wherefore the signal was amplified by across-hybridisation.

Step f) Preparing secondary libraries for cross-hybridisation

Secondary libraries was immobilised on streptavidin beads and digested with either EcoRI or BamHI to release truncated oligonucleotides, devoid of 3'-fixed regions.

Immobilisation of $0^{th}$ Generation Secondary Libraries

200 µl 30% Streptavidin Sepharose High Performance beads in 20% EtOH were centrifuged to pellet the solid phase. The supernatant was disposed and 1200 µl 6×SSC, 0.01% Triton X-100 added. After resuspension of the solid phase, it was again pelleted by centrifugation and the supernatant disposed. The solid phase was resuspended in 140 µl 6×SSC, 0.01% Triton X-100 to give a total volume of app. 200 µl.

Samples AI-DII (app. 490 µl PCR-product) were added 200 µl 20×SSC+20 µl equilibrated streptavidin beads. Next, samples AI-DII were incubated at RT for 30 minutes with mixing. Then the samples were transferred to spin-filters (2× 350 µl) and centrifuged at 2200 rpm for 3 minutes. In the first wash, samples were added 300 µl 10× wash buffer, 0.01% Triton X-100 and centrifuged at 2200 rpm for 3 minutes. For second wash, the samples were added 300 µl buffer R (50 mM Tris-HCl pH 8, 10 mM MgCl2, 100 mM NaCl) and centrifuged at 2200 rpm for 3 minutes.

Release of truncated oligonucleotides from streptavidin beads by restriction:

Next, the beads of sample AI, BI, CI and DI were added 100 µl of 1× buffer BamHI containing 1×BSA, while beads of AII, BIT, CII and DII were added 100 µl of 1× buffer EcoRI. Finally, 4 µl of BamHI (100 U/µl) was added to sample AI, BI, CI and DI, and 4 µl of EcoRI (100 U/µl) to sample AII, BII, CII and DII, followed by incubation at 37° C. cabinet for 2 hours.

The supernatant containing truncated Oligonucleotides of the restricted samples AI-DII were collected by centrifugation at 2200 rpm for 3 minutes, followed by a second elution with 100 µl buffer R and centrifugation at 13,000 rpm for 1 minute. The pooled eluates were then extracted with 100 µl phenol, extracted with 200 µl chloroform and added 1 µl glycogen and EtOH precipitated by adding 20 µl 3M NaAc pH 4.5 and 400 µl 95% EtOH and, incubation at −80° C. freezer for 20 minutes, centrifugation at 0° C., 20000 g for 40 minutes, disposal of the supernatant, air drying of the pellet before dissolution in 50 µl 0.01% Triton X-100 by incubation at RT for 30 minutes with mixing. Next, the samples were desalted by gel-filtration on G25 columns (MicroSpin G-25 columns, Amersham, 27-5325-01). Finally, 2.5 µl of the purified restricted samples AI, AI, BI, BII, CI, CII, DT, DII together with 2.5 and 5 µl of the 25 bp DNA ladder were analysed on a 4% GTG agarose gel.

2 µl of the purified samples AI-DII were estimated to contain app 1 pmol.

Step-g) Cross-hybridisation

Selection by cross-hybridisation of upstream and downstream fragments from library-1 and library-2

Truncated $0^{th}$ generation secondary libraries and hybridisation buffer (360 µl 5 M NaCl+18 µl 1 M Tris pH 8+18 µl 1% Triton X-100+204 µl H2O) were aliquoted according to the scheme below.

20 µl Hybridisation Buffer+

AI+CII:
a-1: 20 µl 10× diluted AI (app 1 pmol; PCR-EcoRI-1-NS)+20 µl 10× diluted CII (app 1 pmol; PCR-BamHI-2-NS)
 a-2: 20 µl 100× diluted AI+20 µl 100× diluted CII
 a-3: 20 µl 1000× diluted AI+20 µl 1000× diluted CII
 a-4: 20 µl 10,000× diluted AI+20 µl 10,000× diluted CII
BI+DII:
b-1: 20 µl 10× diluted BI (app 1 pmol; PCR-EcoRI-1-N)+20 µl 10× diluted DII (app 1 pmol; PCR-BamHI-2-N)
 b-2: 20 µl 100× diluted BI+20 µl 100× diluted DII
 b-3: 20 µl 1000× diluted BI+20 µl 1000× diluted DII
 b-4: 20 µl 10,000× diluted BI+20 µl 10,000× diluted DII
CI+AII:
c-1: 20 µl 10× diluted CI (app 1 pmol; PCR-EcoRI-2-S)+20 µl 10× diluted AII (app 1 pmol; PCR-BamHI-1-S)
 c-2: 20 µl 100× diluted CI+20 µl 100× diluted AII
 c-3: 20 µl 1000× diluted CI+20 µl 1000× diluted AII
 c-4: 20 µl 10,000× diluted CI+20 µl 10,000× diluted AII
DI+BII:
d-1: 20 µl 10× diluted DI (app 1 pmol; PCR-EcoRI-2-N)+20 µl 10× diluted BII (app 1 pmol; PCR-BamHI-1-N)
 d-2: 20 µl 100× diluted DI+20 µl 100× diluted BII
 d-3: 20 µl 1000× diluted DI+20 µl 1000× diluted BII
 d-4: 20 µl 10,000× diluted DI+20 µl 10,000× diluted BII
Controls:
e: 20 µl 10× diluted AI+20 µl 0.01% Triton X-100
f: 20 µl 10× diluted BI+20 µl 0.01% Triton X-100
g: 20 µl 10× diluted CII+20 µl 0.01% Triton X-100
h: 20 µl 10× diluted DII+20 µl 0.01% Triton X-100
i: 40 µl 0.01% Triton X-100
j: 20 µl 10× diluted CI+20 µl 0.01% Triton X-100
k: 20 µl 10× diluted DI+20 µl 0.01% Triton X-100
l: 20 µl 10× diluted AII+20 µl 0.01% Triton X-100
m: 20 µl 10× diluted BII+20 µl 0.01% Triton X-100
n: 40 µl 0.01% Triton X-100

EcoRI-1, EcoRI-2, BamHI-1 and BamHI-2 indicate the different fixed sequences, N indicates negative controls without signal-oligo, NS indicates libraries with signal (noise+signal), i.e. PCR-EcoRI-1-NS contains fixed region EcoRI-1 and both signal and noise oligos Next, the libraries (tubes a-1 to n) were heated to 94° C. for 5 minutes followed by incubation at 65° C. for 2 h.

PCR-Amplification

Two PCR mixes (I and II) were prepared each containing 540 µl H2O+75 µl 10× buffer+22.5 µl 50 mM MgCl2+30 µl dNTPs, 5 mM each+7.5 µl polymerase.

30 µl 10 µM PCR-EcoRI-1+30 µl 10 µM PCR-BamHI-2 were added to mix I

30 µl 10 µM PCR-EcoRI-2+30 µl 10 µM PCR-BamHI-1 were added to mix II

Each mix was then transferred to PCR tubes (11×49 µl), where after 1 µl of hybridisation mix a-1, a-2, a-3, a-4, b-1, b-2, b-3, b-4, e, f, g, h, i was added to PCR mix I (13×1 µl) and 1 µl of hybridisation mix c-1, c-2, c-3, c-4, d-1, d-2, d-3, d-4, j, k, l, m, n was added to one PCR mix II (13×1 µl).

Amplification was performed using the following program:
Extension 72° C., 5 min
Initial denaturation: 94° C., 5 min
30 cycles: 94° C., 30 sec
61° C., 60 sec
72° C., 10 sec
Final extension: 72° C., 5 min Monitoring PCR Amplification of the Libraries After amplification, 5 µl of the PCR samples was added 2.5 µl H2O+2.5 µl 30% glycerol and resolved together with a 25 bp DNA ladder on 4% GTG agarose gels using 1×TBE as running buffer.

Using 1 pmol, 0.1 pmol and 0.01 pmol truncated oligonucleotide for cross-hybridisation and subsequent PCR amplification gave strong bands, while 0.001 pmol only gave weak bands (data not shown).

Step h) Monitoring evolution of the secondary libraries by restriction analysis

The following PCR samples were desalted with a G25 column: a-3, a-4, b-3, b-4, c-3, c-4, d-3 and d-4 and E (positive control).

5 µl of the desalted samples were each added 3 µl H2O+1 µl StuI+1 µl buffer 2 and incubated at 37° C. for 2 hours.

As restriction controls, samples with 2 µl H2O instead of StuI were incubated at 37° C. for 2 hours.

Figure 14:
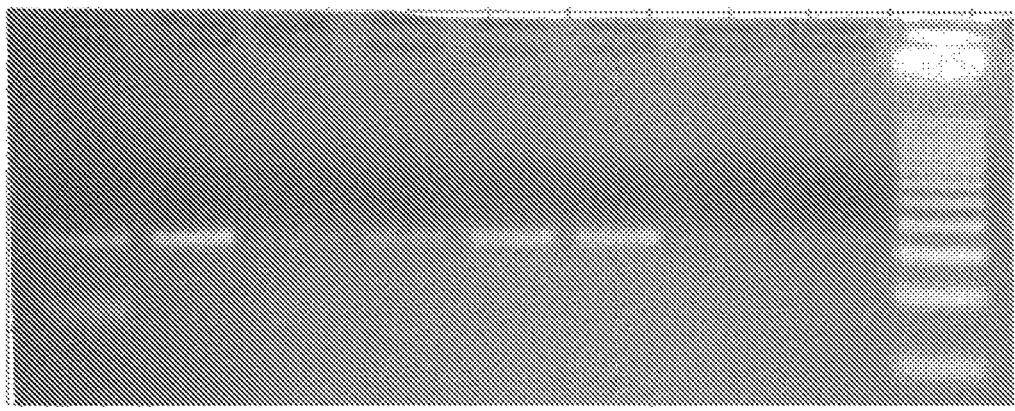
Figure 14:
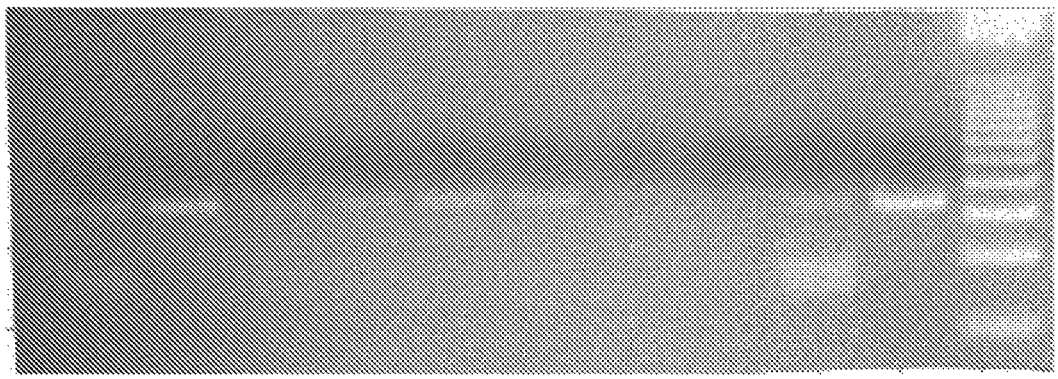

The samples were then added 3 µl 3.0% glycerol resolved on a 4% GTG agarose gel in the following order:

FIG. 14A: +/− StuI of a-3, a-4, b-3 and b-4 (and 2.5 µl of a 25 bp DNA ladder).

FIG. 14B: +/− StuI of c-3, c-4, d-3, d-4 and E (and 2.5 µl of a 25 bp DNA ladder).

Some of the bands were faint, but the following could be observed:

The positive control, E, was cleaved 60-70%, whereas samples a-3, a-4, c-3 and c-4 was cleaved app. 50%. Thus, we infer that $1^{st}$ generation secondary libraries constituted at least 1 signal oligonucleotide per 1 noise oligonucleotide, which corresponds to an enrichment of app. $6 \times 10^9$.

In other words, if a 10e5 fold selection can be done on a library of 10e10 molecules (encoded compounds or aptamers), one round of cross-hybridisation should suffice for identification of the best binders of the library.

Example 5

Example 5 is similar to example 3, except that larger libraries were used.

DNA-oligonucleotides used for positive restriction control:

```
HD1-PCR-1:
5'GATGAT AGTAGT TCGTCG TCAC

HD1-PCR-2:
5'-biotin-GCAGCA ACTACT CATCAT GACT

StuI-template:
5'GATGAT AGTAGT TCGTCG TCAC CGAGGT TATAGC AGGCCT
CGTTTC CCTCCG ACTAGC T AGTC ATGATG AGTAGT TGCTGC
```

PCR-Primers

Set 1:

```
Primary PCR primer 1, PCR-BamHI-1:
5' GGGATA TAGCAA TCCTAC GG

Primary PCR primer biotin 1, PCR-BamHI-1-bt:
5' b GGGATA TAGCAA TCCTAC GG

Secondary PCR primer 1, PCR-EcoRI-1:
5' GGAGTA GCAAAG TAGCGT GA

Secondary PCR primer biotin 1, PCR-EcoRI-1-bt:
5' b GGAGTA GCAAAG TAGCGT GA
```

Set 2:

```
Primary PCR primer 2, PCR-BamHI-2:
5' GGCGTT TCTAAC AACGAA GG

Primary PCR primer biotin 2, PCR-BamHI-2-bt:
5' b GGCGTT TCTAAC AACGAA GG

Secondary PCR primer 2, PCR-EcoRI-2:
5' GGCGTG GACACC ATTTAT GA

Secondary PCR primer biotin 2, PCR-EcoRI-2-bt:
5' b GGCGTG GACACC ATTTAT GA
```

Step a) Providing the primary libraries

As in example 1, redundant positions during DNA-oligonucleotide synthesis are used to build the libraries.

Primary Library 1

```
Signal oligo 1, target-StuI-1:
5' b GGGATA TAGCAA TCCTAC GGATCC ACCTAG TTGGAG
CGAACA GGCCTT GCTATA ACCTTG GAATTC ACGCTA CTTTGC
TACTCC
```

"GGATCC", "AGGCCT" and "GAATTC" are the sequences recognised by the ds DNA restriction enzymes BamHI (NEB, R0136L, 100 U/μl), StuI (NEB, R0187L, 10 U/μl) and EcoRI (NEB, R01010L, 100 U/μl, respectively)

```
Noise oligo 1, library-e10-1:
5' GGGATA TAGCAA TCCTAC GGATCC MYDKMC KYHRMA
YRBMMT RRDMYA RYVMKC MYDKYA
```

Primary Library 2

```
Signal oligo 2, target-StuI-2:
5' b GGCGTT TCTAAC AACGAA GGATCC ACCTAG TTGGAG
CGAACA GGCCTT GCTATA ACCTTG GAATTC ATAAAT GGTGTC
CACGCC Noise oligo 2, library-e10-2:
5' GGCGTT TCTAAC AACGAA GGATCC MYDKMC KYHRMA
YRBMMT RRDMYA RYVMKC MYDKYA GAATTC ATAAAT GGTGTC
CACGCC
```

(Actual redundancy: $2^{24} \times 3^6 = 1.2 \times 10^{10}$)

First Round

Step b) Contacting the target molecule with at least a subset of the primary library Primary libraries, 20×SSC and 0.2% Triton X-100 were aliquoted into tubes A-D according to the scheme below to give a total volume of 100 μl (6×SSC, 0.01% Triton X-100).

A) Library-1:
30 μl 20×SSC
5 μl 0.2% Triton X-100
60 μl 200 μM library-e10-1
5 μl 0.2 pM target-StuI-1

B) Negative control omitting signal in primary library, otherwise as A:
30 μl 20×SSC
5 μl 0.2% Triton X-100
60 μl 200 μM library-e10-1
5 μl 0.01% Triton X100

C) Library-2:
30 μl 20×SSC
5 μl 0.2% Triton X-100
60 μl 200 μM library-e10-2
5 μl 0.2 pM target-StuI-2

D) Negative control omitting signal in primary library, otherwise as C:
30 μl 20×SSC
5 μl 0.2% Triton X-100
60 μl 200 μM library-e10-2
5 μl 0.01% Triton X-100

Next, the libraries (sample A to D) were heated to 94° C. for 5 minutes followed by incubation at 65° C. for 10 minutes.

Equilibration of the solid phase bound target:

Solid phase I) 30% Streptavidin Sepharose High Performance beads in 20% EtOH, Amersham, 17-5113-01:

60 μl solid phase suspension was centrifuged to pellet the solid phase. The supernatant was disposed and 360 μl 6×SSC, 0.01% Triton x-100 added. After resuspension of the solid phase, it was again pelleted by centrifugation and the supernatant disposed. The solid phase was resuspended in 42 μl 6×SSC, 0.01% Triton X-100 to give a total volume of app. 60 μl.

Solid phase II) 50% Tetrameric Avidin Resin in 20% EtOH, Promega, V2591:

36 μl solid phase suspension was centrifuged to pellet the solid phase, otherwise as I.

20 μl equilibrated solid phase 1 was added to samples A and B and 20 μl equilibrated solid phase II was added to samples C and D. Next, samples A-D were incubated at 65° C. for 60 minutes with mixing in a table shaker.

Step c) Selecting the oligonucleotide species of the primary library that interact specifically with the target molecule After incubation with the solid phase bound target, samples were centrifuged, supernatant disposed, beads resuspended in 300 µl 10× wash buffer (1 N NaCl, 100 mM Tris-HCl pH 8) containing 0.01% Triton X-100 and re-incubated at 65° C. for 30 minutes with mixing. Then the samples were centrifuged, the supernatant disposed and beads resuspended in 300 µl 10× wash buffer. This was followed by a third wash where the samples were centrifuged, the supernatant disposed and beads resuspended in 300 µl 1× wash buffer. Next, the beads were pelleted by centrifugation and the supernatant disposed. Residual biotin binding sides on the solid phase were blocked by addition of 1 µl 20 mM Biotin (Sigma, B-4501) and the total volume of the samples adjusted to 22 µl by addition of app. 16 µl 1× wash buffer. This was followed by incubation at room-temperature for 5 minutes with mixing.

Step d) Amplifying selected oligonucleotides to create $0^{th}$ generation secondary libraries:

8 PCR mixes (AI to DII) were prepared each containing:
396 µl $H_2O$
55 µl 10× buffer (Bioline, BIO-21050)
16.5 µl 50 mM $MgCl_2$ (Bioline, BIO-21050)
22 µl dNTPs, 5 mM each (Bioline, BIO-39025)
5.5 µl polymerase (BIO-X-ACT long, Bioline, BIO-21050)

Next, primers were added as follows:
A-I and B-I: 22 µl 10 µM PCR-BamHI-1-bt+22 µl 10 µM PCR-EcoRI-1
A-II and B-II: 22 µl 10 µM PCR-BamHI-1+22 µl 10 µM PCR-EcoRI-1-bt
C-I and D-I: 22 µl 10 µM PCR-BamHI-2-bt+22 µl 10 µM PCR-EcoRI-2
C-II and D-II: 22 µl 10 µM PCR-BamHI-2+22 µl 10 µM PCR-EcoRI-2-bt As negative PCR controls, 49 µl was collected from each of the above PCR mix and each added 1 µl 1× wash buffer.

The remaining 490 µl of the PCR mixes was added 10 µl of selected primary libraries (A to A-I and A-II, B to B-I and B-II, C to C-I and c-II, D to D-I and D-II) and transferred to PCR tubes (5×100 µl).

As a positive PCR and restriction control, sample E, 5 µl 0.2 pM StuI-template was added to a PCR mix containing:
32 µl $H_2O$
5 µl 10× buffer
1.5 µl 50 mM $MgCl_2$
2 µl dNTPs, 5 mM each
2 µl 10 µM HD1-PCR-1
2 µl 10 µM HD-PCR-2
0.5 µl polymerase Amplification was done using the following program:
Initial denaturation: 94° C., 5 min.
30 cycles: 94° C., 30 sec
61° C., 60 sec
72° C., 10 sec.
Final extension: 72° C., 5 min After amplification, the beads were removed from sample AI-DII by spin-filtration (Ultrafree-MC filter microporous 0.22 micron, Millipore, UFC3 0GV NB) and 10 µl was kept as backup.

Step e) Monitoring the evolution of the secondary libraries

The $0^{th}$ generation secondary libraries represent an amplification of the information output (both noise and signal) from the primary selections.

5 µl negative PCR controls were added 5 µl $H_2O$ and 3 µl 30% glycerol and resolved on a 4% GTG (BioWhittaker (BMA), 50084) agarose gel. No PCR-products was observed for any of the samples (data not shown).

5 µl of samples AI, AII, BI, BII, CI, CII, DI, DII, E were added 1 µl StuI+1 µl buffer 2 (NEB, B7002S)+3 µl $H_2O$ and incubated at 37° C. for 2 hours.

As negative restriction controls, identical samples but with 1 µl $H_2O$ instead of StuI were incubated at 37° C. for 2 hours.

The samples were then added 3 µl 30% glycerol and resolved on a 4% GTG agarose gel using 1×TBE as running buffer.

Figure 15:
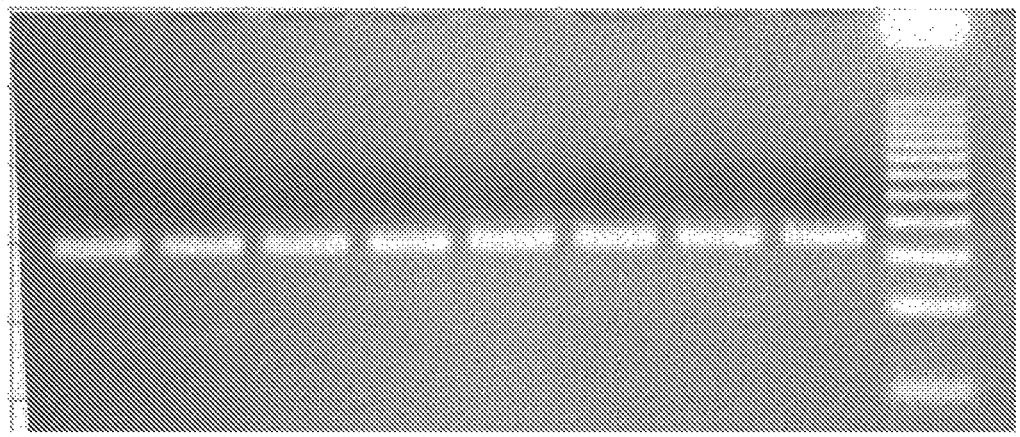
Figure 15:
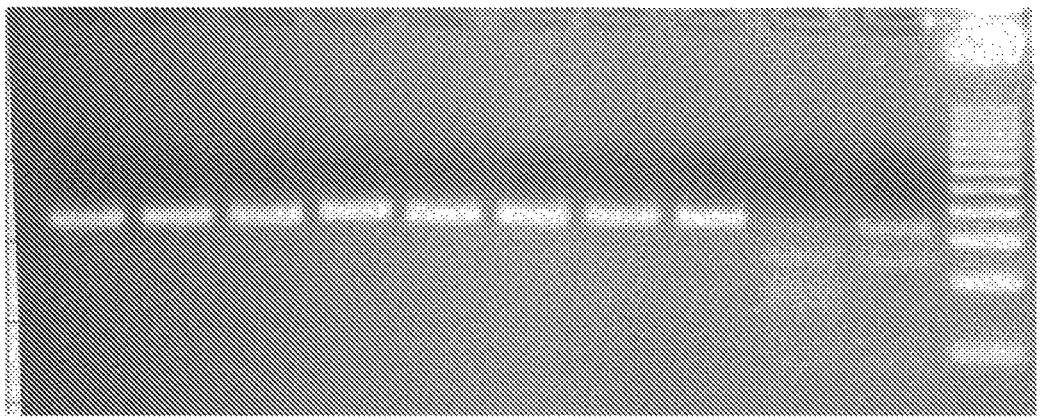

FIG. 15A: +/− StuI of sample AI, AII, BI, BII and 25 bp DNA ladder (2.5 µl).

FIG. 15B: +/− StuI of sample CI, CII, DI, DII, E and 25 bp DNA ladder (2.5 µl).

No restriction of samples AI-DII was detected after round 1, wherefore the signal was amplified by cross-hybridisation of $0^{th}$ generation secondary libraries Step f) Preparing secondary libraries for cross-hybridisation Secondary libraries was immobilised on streptavidin beads, digested with either EcoRI or BamHI to release truncated Oligonucleotides, devoid of 3'-fixed regions.

Immobilisation of $0^{th}$ Generation Secondary Libraries

200 µl 30% Streptavidin Sepharose High Performance beads in 20% EtOH were centrifuged to pellet the solid phase. The supernatant was disposed and 1200 µl 6×SSC, 0.01% Triton X-100 added. After resuspension of the solid phase, it was again pelleted by centrifugation and the supernatant disposed. The solid phase was resuspended in 140 µl 6×SSC, 0.0% Triton X-100 to give a total volume of app. 200 µl.

Samples AI-DII (495 µl PCR-product) were added 200 µl 20×SSC+20 µl equilibrated streptavidin beads. Next, samples AI-DII were incubated at RT for 30 minutes with mixing. In the first wash, samples were centrifuged, supernatant disposed, beads resuspended in 300 µl 1× wash buffer, 0.01% Triton X-100 and re-incubated at RT for 30 minutes with mixing. For second wash, the samples were centrifuged, supernatant disposed and beads resuspended in 300 µl buffer R (50 mM Tris-HCl pH 8, 10 mM $MgCl_2$, 100 mM NaCl).

Release of truncated Oligonucleotides from streptavidin beads by restriction:

Next, the beads were centrifuged at 2200 rpm for 3 minutes and the beads of sample AI, BI, CI and DI were added 100 µl of 1× buffer BamHI containing 1×BSA, while beads of AII, BII, CII and DII were added 100 µl of 1× buffer EcoRI. Finally, 4 µl of BamHI (100 U/µl) was added to sample AI, BI, CI and DI, and 4 µl of EcoRI (100 U/µl) to sample AII, BII, CII and DII, the samples and samples incubated at 37° C. for 2 hours.

The supernatant containing truncated oligonucleotides of the restricted samples AI-DII were collected by spin-filtration: 1 min centrifugation at 1000 g followed by a second elution with 100 µl buffer R and 30 sec. centrifugation at 13.000 g and pooling of the two eluates. The samples were then extracted with 200 µl phenol, extracted with 200 µl chloroform and added 1 µl glycogen and ethanol precipitated by adding 20 µl 3M NaAc pH 4.5 and 400 µl 95% EtOH and incubation at −80° C. 20 minutes, centrifugation at 0° C., 20000 g for 40 minutes, disposal of the supernatant, and air drying of the pellet before dissolution in 50 µl 0.01% Triton X-100 by incubation at RT for 30 minutes with mixing. Next, the samples were desalted by gel-filtration on G25 columns (MicroSpin G-25 columns, Amersham, 27-5325-01). Finally, 2.5 µl of samples AI, AII, BI, BII, CI, CII, DI, DII, together with 2.5 and 5 µl of a 25 bp DNA ladder, were analysed on a 4% GTG agarose gel using 1×TBE as running buffer (data not shown).

20 µl of the purified samples AI-DII were estimated to contain app 1 pmol truncated Oligonucleotides.

Step-g) Cross-hybridisation

Cross-hybridisation was done by adding truncated oligonucleotides to 20 µl hybridisation buffer (380 µl 5 M NaCl+18 µl 1 M Tris pH 8+18 µl 1% Triton X-100+204 µl $H_2O$) according to the scheme below.

20 µl Hybridisation Buffer+

AI-CII:
a-1: 20 µl AI (app 1 pmol; PCR-EcoRI-1-NS)+20 µl CII (app 1 pmol; PCR-BamHI-2-NS)
a-2: 20 µl 10× diluted AI+20 µl 10× diluted CII
a-3: 20 µl 100× diluted AI+20 µl 100× diluted CII
a-4: 20 µl 1000× diluted AI+20 µl 1000× diluted CII
BI+DII:
b-1: 20 µl BI (app 1 pmol; PCR-EcoRI-1-N)+20 µl DII (app 1 pmol; PCR-BamHI-2-N)
b-2: 20 µl 10× diluted BI+20 µl 10× diluted DII
b-3: 20 µl 100× diluted BI+20 µl 100× diluted DII
b-4: 20 µl 1000× diluted BI+20 µl 1000× diluted DII
CI+AII:
c-1: 20 µl CI (app 1 pmol; PCR-EcoRI-2-NS)+20 µl AII (app 1 pmol; PCR-BamHI-1-NS)
c-2: 20 µl 10× diluted CI+20 µl 10× diluted AII
c-3: 20 µl 100× diluted CI+20 µl 100× diluted AII
c-4: 20 µl 1000× diluted CI+20 µl 1000× diluted AII
DI+BII:
d-1: 20 µl DI (app 1 pmol; PCR-EcoRI-2-N)+20 µl BII (app 1 pmol; PCR-BamHI-1-N)
d-2: 20 µl 10× diluted DI+20 µl 10× diluted BII
d-3: 20 µl 100× diluted DI+20 µl 100× diluted BII
d-4: 20 µl 1000× diluted DI+20 µl 1000× diluted BII
Controls:
e: 20 µl AI+20 µl $H_2O$
f: 20 µl BI+20 µl $H_2O$
g: 20 µl CII+20 µl $H_2O$
h: 20 µl DII+20 µl $H_2O$
i: 20 µl 0.01% Triton X-100+20 µl $H_2O$
j: 20 µl CI+20 µl $H_2O$
k: 20 µl DI+20 µl $H_2O$
l: 20 µl AII+20 µl $H_2O$
m: 20 µl BII+20 µl $H_2O$
n: 20 µl 0.01% Triton X-100+20 µl $H_2O$
EcoRI-1, EcoRI-2, BamHI-1 and BamHI-2 indicate the different fixed sequences, N indicates negative controls without signal-oligo, NS indicates libraries with signal (noise+signal), i.e. PCR-EcoRI-1-NS contains fixed region EcoRI-1 and both signal and noise oligos Next, the libraries (tubes a-1 to n) were heated to 94° C. for 5 minutes followed by incubation at 65° C. for 1 h.

PCR-Amplification

Two PCR mixes (I and II) were prepared each containing 540 µl $H_2O$+75 µl 10× buffer+22.5 µl 50 mM $MgCl_2$+30 µl dNTPs, 5 mM each+7.5 µl polymerase.

30 µl 10 µM PCR-EcoRI-1+30 µl 10 µM PCR-BamHI-2 were added to mix I

30 µl 10 µM PCR-EcoRI-2+30 µl 10 µM PCR-BamHI-1 were added to mix II

Each mix was then transferred to PCR tubes (13×49 µl), where after 1 µl of hybridisation mix a-1, a-2, a-3, a-4, b-1, b-2, b-3, b-4, e, f, g, h, i was added to PCR mix I (13×1 µl) and 1 µl of hybridisation mix c-1, c-2, c-3, c-4, d-1, d-2, d-3, d-4, j, k, l, m, n was added to PCR mix II (13×1 µl).

Amplification was performed using the following program:
Extension 72° C., 5 min
Initial denaturation: 94° C., 5 min
30 cycles: 94° C., 30 sec
61° C., 60 sec
72° C., 10 sec
Final extension: 72° C., 5 min After amplification, 5 µl of the PCR samples was added 2.5 µl $H_2O$+2.5 µl 30% glycerol and resolved together with a 25 bp DNA ladder on 4% GTG agarose gels using 1×TBE as running buffer Using 1 and 0.1 pmol truncated Oligonucleotides for cross- and subsequent amplification gage strong bands on the gel, whereas using 0.01 pmol gave only weak bands (data not shown).

Step h) Monitoring evolution of the secondary libraries by restriction analysis

The following PCR samples were desalted with a G25 column: a-2, b-2, c-2 and d-2 and E (positive control).

5 µl of the desalted samples 1-5 were each added 3 µl $H_2O$+1 µl StuI+1 µl buffer 2 and incubated at 37° C. for 2 hours.

As restriction controls, identical samples except added 1 µl extra $H_2O$ instead of StuI were incubated at 37° C. for 2 hours.

The samples were then added 3 µl 30% glycerol resolved on a 4% GTG agarose gel.

Figure 16:
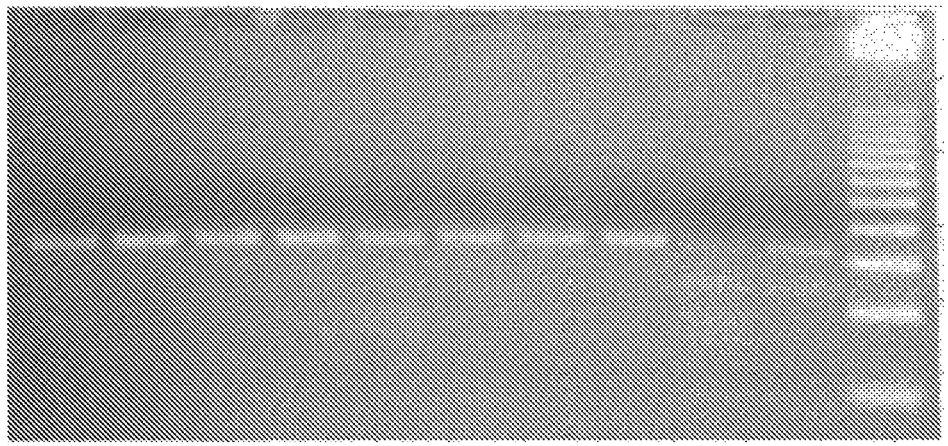

FIG. 16: +/− AvrII of a-2, b-2, c-2, d-2 and E and 2.5 µl of a 25 bp DNA ladder.

Digestion was only modest, but it could be seen that around 10-20% of a-2 and c-2 was cleaved by StuI. The positive control had been digested about 60-70% (note that the band contain a PCR by-product.). Thus, the signal had been enriched from 1 in $1{,}2\times10^{10}$ to 1 in 5, i.e. an enrichment of approximately $2{,}4\times10^9$.

The invention claimed is:

1. A method for identification of a most abundant oligonucleotide species in a library of oligonucleotides comprising more than $10^6$ oligonucleotide species, wherein the oligonucleotide species of the library of oligonucleotides are not inherently capable of exponential amplification by PCR and comprise a coding sequence, which is characteristic of one oligonucleotide specie of the library of oligonucleotides and only one fixed sequence, which is present in a plurality of the oligonucleotide species of the library of oligonucleotides, said fixed sequence being located on a 5' side of the coding sequence, and wherein the method comprises specifically amplifying a sequence of a hybridised oligonucleotide species using steps of:
  a. incubating the library of oligonucleotides under conditions of hybridization such as to allow complementary coding sequences to hybridize and form hybridized oligonucleotide species;
  b. extending a 3' end of one or more of the hybridised oligonudeotide species, having only one fixed sequence, to provide extended sequences having an extended region, such that the extended region generates a second fixed sequence thereby forming extended sequences having two fixed sequences; and
  c. amplifying the extended sequences comprising two fixed sequences using PCR to provide amplified sequences.

2. The method according to claim 1, wherein the method of specifically amplifying the sequence of a hybridized oligonucleotide species comprises a step of:
  d. identifying an identity of the amplified sequences thereby revealing an identity of the hybridised oligonucleotide species in step a.

3. The method according to claim 2, wherein the amplified sequences of step c, or oligonucleotide species derived thereof, is comprised in a library of oligonucleotides used in a next round of steps a-c, such that an iterative process is initiated wherein each repetition of steps a, b, and c is optionally followed by step d.

4. The method according to claim 1, wherein the library of oligonucleotides is selected from the group of a library of encoded molecules, a library of aptamers, a library of reporter sequences derived from a library of encoded molecules, and a library of reporter sequences derived from a library of aptamers.

* * * * *